US011839658B2

(12) United States Patent
Ho et al.

(10) Patent No.: US 11,839,658 B2
(45) Date of Patent: Dec. 12, 2023

(54) AMINOGLYCOSIDE DERIVATIVES AND NANO-ASSEMBLIES THEREOF, INCLUDING THOSE WITH QUORUM SENSING INHIBITORY FUNCTION

(71) Applicant: HELMHOLTZ-ZENTRUM FÜR INFEKTIONSFORSCHUNG GMBH, Braunschweig (DE)

(72) Inventors: Duy-Khiet Ho, Saarbrücken (DE); Brigitta Loretz, Saarbrücken (DE); Claus-Michael Lehr, Saarbrücken (DE)

(73) Assignee: HELMHOLTZ-ZENTRUM FÜR INFEKTIONSFORSCHUNG GMBH, Braunschweig (DE)

( * ) Notice: Subject to any disclaimer, the term of this patent is extended or adjusted under 35 U.S.C. 154(b) by 829 days.

(21) Appl. No.: 16/627,100

(22) PCT Filed: Jun. 8, 2018

(86) PCT No.: PCT/EP2018/065232
§ 371 (c)(1),
(2) Date: Dec. 27, 2019

(87) PCT Pub. No.: WO2019/001935
PCT Pub. Date: Jan. 3, 2019

(65) Prior Publication Data
US 2020/0360524 A1    Nov. 19, 2020

(30) Foreign Application Priority Data

Jun. 30, 2017  (EP) .................................... 17179011

(51) Int. Cl.
*A61K 47/55*  (2017.01)
*A61K 47/54*  (2017.01)
*C07H 15/232*  (2006.01)

(52) U.S. Cl.
CPC .......... *A61K 47/552* (2017.08); *A61K 47/543* (2017.08); *C07H 15/232* (2013.01)

(58) Field of Classification Search
CPC ... A61K 47/543; A61K 47/552; C07H 15/232
USPC ........................................... 424/1.69; 514/54
See application file for complete search history.

(56) References Cited

FOREIGN PATENT DOCUMENTS

| EP | 1 441 224 | 7/2004 |
|---|---|---|
| WO | 2010/004433 | 1/2010 |

OTHER PUBLICATIONS

Abed et al. (Scientific Reports | 5:13500 |, Published: Aug. 27, 2015, 1-14).*
Wallace et al. (Antimicrobial Agents and Chemotherapy, vol. 28, No. 2, Aug. 1985, p. 274-281).*
Bracchi et al. (Chem. Commun., 2015, 51, 11052-11055).*
Zhou, Molecules 2020, 25, 5649, p. 1-20. (Year: 2020).*
Mu, OpenNano 5(2021) 100331, p. 1-8. (Year: 2020).*
Pichavant, Marcromolecules 2011, 44, 7879-7887. (Year: 2011).*
International Search Report and Written Opinion of the International Searching Authority, dated Sep. 6, 2018 in corresponding International Patent Application No. PCT/EP2018/065232.
Lin, C.-K. et al.: Synthesis of 1-C-Glycoside-Linked Lipid II Analogues Toward Bacterial Transglycosylase Inhibition, Chemistry—A European Journal, vol. 21, No. 20, Mar. 26, 2015, pp. 7511-7519.
Ramírez, A.S. et al.: Characterization of the single-subunit oligosaccaryltransferase STT3A from *Trypanosoma brucei* using synthetic peptides and lipid-linked oligosaccharide analogs, Glycobiology, vol. 27, No. 6, Mar. 16, 2017, pp. 525-535.
Martinez Farias, M.A. et al.: Isoprenoid Phosphonophosphates as Glycosyltransferase Acceptor Substrates, Journal of the American Chemical Society, vol. 136, No. 24, Jun. 10, 2014, pp. 8492-8495.
Bera, S. et al.: Design, Synthesis, and Antibacterial Activities of Neomycin-Lipid Conjugates: Polycationic Lipids with Potent Gram-Positive Activity, Journal of Medicinal Chemistry, vol. 51, No. 19, Oct. 9, 2008, pp. 6160-6164.
Lewis, J.A.S. et al.: The toxic extractives from *Wedelia asperrima*-II: The structure of wedeloside, a novel diterpenoid aminoglycoside, Tetrahedron, vol. 37, No. 24, Jan. 1, 1981, pp. 4305-4311.
Jabra-Rizk, M. A. et al.: Effect of Franesol on *Staphylococcus aureus* Biofilm Formation and Antimicrobial Susceptibility, Antimicrobial Agents and Chemotherapy, vol. 50, No. 4, Apr. 1, 2006, pp. 1463-1469.

* cited by examiner

*Primary Examiner* — Layla D Berry
(74) *Attorney, Agent, or Firm* — Wenderoth, Lind & Ponack, L.L.P.

(57) ABSTRACT

The present invention relates to conjugates of aminoglycosides and terpenoids, in particular sesquiterpenoids. Furthermore, the present invention relates to nano-assemblies formed by the inventive conjugates and to a method for producing the conjugates and/or the nano-assemblies. The present invention also relates to the inventive conjugates and nano-assemblies for use in therapy, in particular for use in the treatment of infectious diseases. Particularly preferred embodiments of the present invention relate to farnesylated aminoglycosides and nano-assemblies thereof, in which farnesol and its derivatives do not only function as carrier for the aminoglycosides but do themselves have pharmaceutical activity upon cleavage of the conjugate, in particular quorum sensing inhibitory activity.

15 Claims, 12 Drawing Sheets

Farnesoic acid

Farnesyl hydrogen sulfate a-hydroxy Farnesyl Phosphonic Acid

Farnesyl monophosphate

Farnesyl diphosphate

Farnesyl triphosphate

AMINOGLYCOSIDE DERIVATIVES AND NANO-ASSEMBLIES THEREOF, INCLUDING THOSE WITH QUORUM SENSING INHIBITORY FUNCTION

The project leading to this application has received funding from the European Union's Horizon 2020 research and innovation programme under the Marie Sklodowska-Curie grant agreement No. 642028.

The present invention relates to conjugates of aminoglycosides and terpenoids, in particular sesquiterpenoids. Furthermore, the present invention relates to nano-assemblies formed by the inventive conjugates and to a method for producing the conjugates and/or the nano-assemblies. The present invention also relates to the inventive conjugates and nano-assemblies for use in therapy, in particular for use in the treatment of infectious diseases.

Aminoglycosides represent an important family of antibiotic drugs. Aminoglycosides are widely used clinically for treating many infectious diseases, especially for infections caused by various types of gram-negative bacteria, and in particular by biofilm-forming bacteria. The term "aminoglycoside" as used herein, refers to aminocyclitol-containing molecules, which are chemically consisting of two or more aminosugars attached to the aminocyclitol ring in glycosidic linkage, having an antibiotic function. The large class of aminoglycoside antibiotics contains structurally diverse members in several molecular families. A list of exemplary aminoglycosides is presented in the present specification further below.

Tobramycin, for instance, is widely applied for treatment of several infectious diseases in different formulations for delivery, and routes of administration. For example, TOBI® solution for inhalation (product of Novartis) is a Tobramycin solution for inhalation for treatment of lung infections, particularly in cystic fibrosis patients. This product is recommended to be used as 300 mg Tobramycin in 5 mL ampule for a single use for 28 days. TOBI® PODHALER™ (another product of Novartis) is a Tobramycin inhalation powder. This product is administrated as 28 mg capsules for inhalation twice-daily for 28 days. Tobramycin Ophthalmic Solution (product of Bausch and Lomb) is Tobramycin for treatment of ophthalmic infection. There are many other examples for aminoglycosides such as Gentamicin and Neomycin for treatment of infectious skin or Amikacin for treatment of infections caused by a wide range of multi-resistant bacteria.

Although there are tremendous developments of therapeutic approaches, particularly new drug class synthesis, formulation and administration, the clinical treatments by using aminoglycosides remain problematic for several reasons. Notably, aminoglycosides are highly charged molecules. This causes strong interaction with biological barriers, e.g. biofilm matrix or mucus, which leads to slow or incomplete penetration of drug and reach to targeting side. As the results, aminoglycosides dose could be below minimum inhibitory concentration (MIC) and cause severe resistances of bacteria, especially in complex infectious diseases. Furthermore, the drugs can only accomplish the termination of spreading bacteria, but biofilms and mucus-embedded biofilms persist, and cannot be completely eradicated. Moreover, the high dose of aminoglycosides, e.g. in case of TOBI® solution for inhalation, which is in particular required to treat cystic fibrosis related infections might cause side effects on patients due to the high toxicity of the free form of aminoglycoside molecules, in particular when the drug is released in a burst.

With mentioned reasons, the use of aminoglycosides is necessary, but there are huge limitations that need to be overcome. In summary, the free form of aminoglycosides is not sufficiently delivered locally to targeted sites of application. Hence, high doses of drugs are applied leading to side effects due to the high toxicity of aminoglycosides. For example, tobramycin and amikacin are harmful to kidney and streptomycin is harmful to the ears. Additionally, there is no controlled release kinetic of the free form of aminoglycosides. Thus, there is no prolonged therapeutic window. Furthermore, as described above the free forms of aminoglycosides have problems of crossing biological barriers such as biofilms or mucus.

The term "biological barriers", as used herein particularly refers to the restrictions in absorption and distribution of an active in the body by limitation of water solubility or permeability (for example across eukaryotic cell membranes, the cell envelope of Gram-negative bacteria, permeation across non-cellular barriers as mucus, biofilm matrix). Delivery of a therapeutic relevant amount of a drug to the target needs sufficient water-solubility as well as permeability.

A known strategy for overcoming biological barriers is encapsulating drugs in nano-sized carriers. Nanotechnology in pharmaceutical applications has been evaluated as technique in delivery of drugs, which aims to protect drugs from degradation and burst release, and to deliver sustainable amount of drugs to targeting sites. Although there are many intense studies on developing nanomedicines for severely infectious diseases, there is a variety of unsolved problems. Namely, the loading rate with respect to carrier materials is poor. Furthermore, there is a burst release of encapsulated drugs right after administration. The main reason for burst release in the prior art is that drugs are released based on the concentration gradient and carrier's stability, for example drug loaded liposomes. Another disadvantage of the prior art is that there are no well-balanced carrier materials which are biodegradable, biocompatible and allow design of carrier systems that could overcome biological barriers.

Aminoglycoside-lipid conjugates have been described in the prior art as well. For example, WO 2010/004433 A2 and Bera et al. ("Design, Synthesis, and Antibacterial Activities of Neomycin-Lipid Conjugates: Polycationic Lipids with Potent Gram-Positive Activity"; J. Med. Chem., 2008, 51, 6160-6164) describe that aminoglycoside-lipid conjugates may have improved antibacterial activities as compared to non-conjugated aminoglycosides. Bera et al. disclose that neomycin-lipid conjugates were made in an attempt to enhance the uptake of aminoglycosides into the bacterial cell and that the conjugates may be useful for prevention of biofilms.

The anti-bacterial effects of the conjugates were tested against various bacterial strains and clinical isolates. Optimal activity against gram-positive bacteria was achieved by conjugation to saturated $C_{16}$ or $C_{20}$-lipids (p. 6163, left col.). However, the conjugates of Bera et al. did not show strong improvement on efficacy against gram-negative bacteria in contrast to the conjugates of the present invention (see examples 7 and 9 below).

Moreover, the conjugates of Bera et al. have further disadvantages. The aminoglycoside antibiotics were modified with lipid via un-cleavable linkage. Therefore, the modified compounds are considered as new derivatives/class of antibiotic, not anymore the same aminoglycosides which are approved by FDA. The conjugates do not have quorum sensing inhibitory properties. The conjugates could not assemble into nanoparticles. The conjugates would have problems with water-solubility. The conjugates were synthesized via many steps, with low isolated yield, which would result in difficulty in scale-up process.

It is therefore an object of the present invention to overcome the disadvantages of the prior art. In particular, it is an object of the present invention to provide means for increasing the ability of aminoglycosides to overcome biological barriers. The present inventors found that this can be achieved by conjugates of aminoglycosides and terpenoids. A further advantage of the present invention is that terpenoids do not only increase the ability of aminoglycosides to overcome biological barriers but that terpenoids do themselves have pharmaceutical activity. In particular, terpenoids have wide range of anti-bacterial activity. Thus, the conjugate of the present invention represent excipient-free medicine because all of its constituents have pharmacological activity. Farnesol and derivatives thereof are particularly preferred terpenoids because they have quorum sensing inhibitory activity, which may be particularly advantageous for complementing the antibiotic activity of aminoglycosides.

The present inventors found that the problems of the prior art can be overcome by terpenylation, in particular by farnesylation of aminoglycoside molecules. Farnesol is a natural and biocompatible lipid ($C_{15}H_{26}O$) belonging to the sesquiterpene alcohols, which is widely employed in many medical products. The term "farnesylation" means the linkage of farnesyl or derivatives thereof to a target molecule. According to the present specification, the term "farnesylation" includes covalent chemical linkage, linkage by electrostatic interactions and combinations of both.

Preferably, the linkage between the aminoglycoside moiety and the farnesyl moiety of the conjugate of the present invention is pH-sensitive. The term "pH-sensitive" indicates that the linkage is not stable at certain pH-values, in particular at acidic conditions, thereby enabling pH-dependent release of aminoglycoside and farnesol or derivatives thereof from the conjugate. In other words, the conjugates of the present invention are preferably cleavable, in particular in a pH-dependent manner. More preferably, the conjugates are cleavable at acidic conditions. This is particularly advantageous because this supports pharmaceutical activity in the intracellular or infectious environment. An infectious environment may for example be a biofilm. Importantly, both the intracellular environment and the biofilm environment generally have an acidic pH, thus causing cleavage of the pH-sensitive linkage between the aminoglycoside moiety and the farnesyl moiety and thereby releasing the aminoglycoside and the farnesyl moiety.

The present inventors found that the farnesylated aminoglycosides of the present invention have another advantage. Namely, farnesol and its derivatives have pharmacological effects itself. Therefore, cleavage of the conjugates of the present invention preferably releases two moieties with distinct and complementary pharmacological properties. On the one hand, aminoglycosides have antibiotic effects. On the other hand, farnesol and its derivatives have in particular i) anti-biofilm activity and ii) bacteria and fungi quorum sensing inhibitory (QSI) properties. Conjugates comprising moieties with such distinct and complementary pharmacological properties have not been described in the prior art. Therefore, in particular such embodiments of the present invention represent a fundamentally improved class of antimicrobial molecules.

The present inventors found that farnesylation of aminoglycosides may be surprisingly achieved via a "single step" preparation. The present invention allows spontaneous formation of aminoglycoside-containing nanoparticles based on self-assembly with farnesol or farnesol derivatives, in particular without the need of any other supporting materials. In other words, the chemical synthesis can be carried out without catalysts. Furthermore, the respective conjugates and nano-assemblies are entirely composed active compounds as both aminoglycosides and farnesol or derivatives thereof have pharmaceutical activity. Finally, formation of nano-assemblies occurs spontaneously and without the need for any stabilizers like for example polyvinyl alcohol.

The present invention is associated with plenty of advantages, the most important of which can be summarized as follows.

The conjugates of the invention can be prepared in single step reaction.

The conjugates are excipient-free in case the terpenyl moiety is a farnesyl moiety because farnesol and derivatives do not only function as carrier for the aminoglycosides but do themselves have pharmaceutical activity, in particular quorum sensing activity. In other words, such conjugates have a drug loading rate of 100% considering aminoglycoside moiety and farnesyl moiety. The pharmaceutical activity of aminoglycosides on the one hand and farnesol or derivatives thereof on the other hand are distinct and complement each other.

Moreover, even in embodiments that use other terpenyl moieties that cannot be considered as pharmaceutically active substances, the drug loading rate is still 50% or more depending on the molecular weight of the terpenyl moiety and of the aminoglycoside. For example, a conjugate consisting of a tobramycin moiety and a geranyl moiety has a drug loading rate of about 75% calculated as molar mass of tobramycin divided by molar mass of the conjugate. Notably, polymeric nanocarriers reported in literature have typically a tobramycin loading rate of about 4%. Thus, the conjugates of the present invention are clearly advantageous.

The pharmacological activity of the conjugates of the present invention is higher as compared to aminoglycosides alone. It has been found by the present inventors that the minimum inhibitory concentration (MIC) of the conjugates is reduced dramatically as compared to aminoglycosides alone. In fact, the conjugates of the present invention achieve a reduction of the MIC by a factor of 50 as shown in the example section below.

The introduction terpenyl moieties can improve the penetration of the aminoglycosides through bacterial cell walls. Moreover, the presence of lipophilic moieties by covalent linkage or electrostatic interactions strongly decreases charge of aminoglycoside molecules. As the results, the conjugates and nano-assemblies of the present invention do not have strong interaction with biological barriers like mucus or biofilm and penetrate faster through such barriers.

In conjugates in which the aminoglycoside moiety and the terpenyl moiety are linked via a pH-sensitive covalent linkage, release is not based on a concentration gradient. Therefore, a burst release is avoided. The same holds true for conjugates in which the aminoglycoside moiety and the terpenyl moiety are linked via electrostatic interactions. In the latter case, the ionic strength is critical for release. In the first case, release is dependent on pH.

WO 2010/004433 A2 and Bera et al. ("Design, Synthesis, and Antibacterial Activities of Neomycin-Lipid Conjugates: Polycationic Lipids with Potent Gram-Positive Activity"; *J. Med. Chem.*, 2008, 51, 6160-6164) describe aminoglycoside-lipid conjugates. However, the conjugates are water-insoluble and thus less suitable for antibiotic treatment. In contrast, the present invention relates to conjugates that spontaneously form water-soluble nano-assemblies in aqueous media such as water.

Thus, the problems of the prior art are solved by the subject-matter of the patent claims. The problems are in particular solved by a conjugate comprising an aminoglycoside moiety and at least one terpenyl moiety, wherein the terpenyl moiety has at most 20 carbon atoms. Thus, the conjugates of the present invention do not comprise any terpenyl moiety having more than 20 carbon atoms. The problems are also solved by nano-assemblies of such conjugates and by methods of production of such conjugates and nano-assemblies.

Preferably, the conjugate of the present invention comprises exactly one aminoglycoside moiety and exactly one terpenyl moiety. In alternative embodiments, the conjugate may comprise more than one terpenyl moiety, in particular exactly two terpenyl moieties or exactly three terpenyl moieties. The number of terpenyl moieties per aminoglycoside can be adjusted by adjusting the molar ratio of aminoglycoside to terpenoid during conjugation. Generally, the lower the molar ratio of aminoglycoside to terpenoid during conjugation is, the higher is the average number of terpenyl moieties per aminoglycoside in the obtained conjugate. A high average number of terpenyl moieties per aminoglycoside is particularly preferred in embodiments in which the terpenyl moiety is a farnesyl moiety and in which a high QSI activity of the conjugate is desired.

The conjugate may comprise further moieties. However, preferably the conjugate of the invention consists of the aminoglycoside moiety and the at least one terpenyl moiety.

The present inventors found that conjugation of an aminoglycoside with a terpenoid has several advantages. Due to the conjugation, the ability of the aminoglycoside moiety to cross biological barriers such as mucus or biofilm is improved as compared to free aminoglycosides. Furthermore, in particular in embodiments of covalent linkage of the aminoglycoside moiety and the terpenyl moiety, cleavage of the linkage and release of aminoglycoside and terpenoid is triggered by acidic conditions, in particular by pH<6. Importantly, due to a change in metabolism of bacteria inside a biofilm, biofilms generally show a pH gradient with more and more acidic conditions towards the center of the biofilm (Flemming et al., Nature Reviews Microbiology (2016), vol. 14, p. 563-575). Therefore, release of active substances from the conjugate of the present invention is triggered inside biofilms and hence directly where it is needed. Moreover, preferably not only the aminoglycosides of the conjugate are pharmacologically active. Rather, also a huge number of terpenoids have advantageous pharmacological properties. Therefore, the conjugate of the present invention preferably represents an excipient-free medicine.

The terpenyl moiety has at most 20 carbon atoms. Preferably, the terpenyl moiety comprises at least 10 carbon atoms. Preferably, the terpenyl moiety comprises at most 15 carbon atoms. If the number of carbon atoms is very high, the ability of the conjugate to form nano-assemblies may be impaired. Preferably, the terpenyl moiety comprises from 10 to 15 carbon atoms. Particularly preferably, the terpenyl moiety comprises exactly 10 carbon atoms or exactly 15 carbon atoms. Preferably, the terpenyl moiety is selected from the group consisting of geranyl moiety and farnesyl moiety. Preferably, the terpenyl moiety is a sesquiterpenyl moiety. Particularly preferably, the terpenyl moiety is a farnesyl moiety. The farnesyl moiety is particularly advantageous because a conjugate comprising an aminoglycoside and a farnesyl moiety preferably give rise to two distinct pharmaceutically active compounds upon cleavage, namely to an aminoglycoside and to farnesol or a farnesol derivative. Aminoglycosides have antibiotic activity. Farnesol and derivatives thereof, such as farnesal or farnesoic acid, have quorum sensing inhibitory (QSI) activity. Thus, conjugates of an aminoglycoside moiety and a farnesyl moiety represent an excipient-free conjugate, all constituents of which have pharmaceutical activity.

Preferably, the aminoglycoside moiety is based on an aminoglycoside selected from the group consisting of aminoglycosides of kanamycin class, aminoglycosides of gentamicin class, aminoglycosides of neomycin class, aminoglycosides of streptomycin class and aminoglycosides of istamycin class. More preferably, the aminoglycoside moiety is based on an aminoglycoside selected from the group consisting of aminoglycosides of kanamycin class, aminoglycosides of gentamicin class and aminoglycosides of neomycin class. Particularly preferably, the aminoglycoside moiety is based on an aminoglycoside of kanamycin class. The different classes of aminoglycosides are described in more detail in the present specification. It is particularly referred to formulas (I) to (VII) below.

Preferably, the aminoglycoside moiety is based on an aminoglycoside selected from the group consisting of kanamycin A, kanamycin B, kanamycin C, 6'-OH-kanamycin A, dibekacin, tobramycin, amikacin, arbekacin, gentamicin C1, gentamicin C2, gentamicin C1A, geneticin (G418), netilmicin, sisomicin, verdamicin, plazomicin, isepamicin, neomycin B, neomycin C, paromomycin (neomycin E), lividomycin B, lividomycin A, butirosin B/A, ribostamycin, streptomycin, 5'-hydroxystreptomycin, bluensomycin, istamycin A (sannamycin), istamycin B, istamycin C, istamycin $A_0$, istamycin $B_0$, istamycin $C_0$, istamycin $A_1$, istamycin $B_1$, istamycin $C_1$, istamycin $A_2$, apramycin, fortimicin A and fortimicin B. More preferably, the aminoglycoside moiety is selected from the group consisting of tobramycin, amikacin, plazomicin, neomycin B, gentamicin, kanamycin, netilmicin, sisomicin and dibekacin. More preferably, the aminoglycoside moiety is based on an aminoglycoside selected from the group consisting of kanamycin and tobramycin. The term "gentamicin" is used as a collective term for gentamicin C1, gentamicin C2 and gentamicin C1A in the present specification. The term "kanamycin" is used as a collective term for kanamycin A, kanamycin B, kanamycin C and 6'-OH-kanamycin A in the present specification. More preferably, the aminoglycoside moiety is based on an aminoglycoside selected from the group consisting of kanamycin A and tobramycin.

In accordance with the present invention, the term " . . . aminoglycoside moiety is based on an aminoglycoside . . . " indicates that the conjugate of the present invention does not comprise the respective aminoglycoside as such but rather a modified form of the aminoglycoside due the linkage between aminoglycoside moiety and terpenyl moiety. In particular, within the conjugate an amine group of the aminoglycoside may be modified to form part of an imine group or an enamine group or may carry a positive charge in order to link the aminoglycoside moiety to the terpenyl moiety. Such modifications of the aminoglycoside occur during preparation of the conjugate according to the method of the present invention described below. Despite this modification within the conjugate, an unmodified and pharmaceutically active aminoglycoside molecule is released upon cleavage of the conjugate.

The aminoglycoside moiety and the terpenyl moiety may be linked via electrostatic interactions and/or via a covalent linkage. In embodiments, in which the conjugate comprises exactly one aminoglycoside moiety and exactly one terpenyl moiety, the aminoglycoside moiety and terpenyl moiety are either linked via electrostatic interactions or via a covalent linkage. In embodiments, in which the conjugate comprises exactly one aminoglycoside and more than one terpenyl moiety, for example exactly two terpenyl moieties, it may be that (i) all terpenyl moieties are linked to the aminoglycoside moiety via a covalent linkage or that (ii) all terpenyl moieties are linked to the aminoglycoside moiety via electrostatic interactions or that (iii) at least one terpenyl moiety is linked to the aminoglycoside moiety via electrostatic interactions and at least one terpenyl moiety is linked to the aminoglycoside moiety via a covalent linkage.

Preferably, the covalent linkage between aminoglycoside moiety and terpenyl moiety is pH-sensitive. The term "pH-sensitive" indicates that the linkage is not stable at certain pH-values, in particular at acidic conditions, particularly preferably at a pH<5.0, more preferably a pH<5.5, more preferably a pH<6.0, more preferably a pH<6.5. Preferably, the term "not stable" indicates that at least 80% of the aminoglycoside is released from the conjugate after incubation at the indicated pH for at most 8 hours, more preferably at most 6 hours, more preferably at most 4 hours, more preferably at most 2 hours at a temperature of 37° C.

Preferably, the aminoglycoside moiety and the terpenyl moiety are linked via an imine group or via an enamine group. Linkage via an imine group is more preferred. FIG. 1 exemplarily shows a conjugate of the present invention comprising a tobramycin moiety and a farnesyl moiety. The tobramycin moiety and the farnesyl moiety are linked via an imine group. Linkage via an imine group and linkage via an enamine group are pH-sensitive. In particular, they get cleaved at acidic conditions. Whether an imine group or an enamine group is formed depends on whether the terpenoid connects to a primary amine group on the aminoglycoside or to a secondary amine group on the aminoglycoside. This is schematically shown for the conjugation of farnesal to an aminoglycoside in FIG. 2. When farnesal is conjugated to a primary amine group on the aminoglycoside, the farnesyl moiety is linked to the aminoglycoside moiety via an imine group (top). When farnesal is conjugated to a secondary amine group on the aminoglycoside, the farnesyl moiety is linked to the aminoglycoside moiety via an enamine group (bottom).

Particularly preferred conjugates of the present invention are selected from the group consisting of kanamycin A-farnesyl conjugates, kanamycin B-farnesyl conjugates, kanamycin C-farnesyl conjugates, 6'-OH-kanamycin A-farnesyl conjugates, dibekacin-farnesyl conjugates, tobramycin-farnesyl conjugates, amikacin-farnesyl conjugates, arbekacin-farnesyl conjugates, gentamicin C1-farnesyl conjugates, gentamicin C2-farnesyl conjugates, gentamicin C1A-farnesyl conjugates, geneticin (G418)-farnesyl conjugates, netilmicin-farnesyl conjugates, sisomicin-farnesyl conjugates, verdamicin-farnesyl conjugates, plazomicin-farnesyl conjugates, isepamicin-farnesyl conjugates, neomycin B-farnesyl conjugates, neomycin C-farnesyl conjugates, paramomycin (neomycin E)-farnesyl conjugates, lividomycin B-farnesyl conjugates, lividomycin A-farnesyl conjugates, butirosin B/A-farnesyl conjugates, ribostamycin-farnesyl conjugates, streptomycin-farnesyl conjugates, 5'-hydroxystreptomycin-farnesyl conjugates, bluensomycin-farnesyl conjugates, istamycin A (sannamycin)-farnesyl conjugates, istamycin B-farnesyl conjugates, istamycin C-farnesyl conjugates, istamycin $A_0$-farnesyl conjugates, istamycin $B_0$-farnesyl conjugates, istamycin $C_0$-farnesyl conjugates, istamycin $A_1$-farnesyl conjugates, istamycin $B_1$-farnesyl conjugates, istamycin $C_1$-farnesyl conjugates, istamycin $A_2$-farnesyl conjugates, apramycin-farnesyl conjugates, fortimicin A-farnesyl conjugates and fortimicin B-farnesyl conjugates.

More preferably, the conjugates of the present invention are selected from the group consisting of tobramycin-farnesyl conjugates, amikacin-farnesyl conjugates, plazomicin-farnesyl conjugates, neomycin B-farnesyl conjugates, gentamicin-farnesyl conjugates, kanamycin-farnesyl conjugates, netilmicin-farnesyl conjugates, sisomicin-farnesyl conjugates and dibekacin-farnesyl conjugates. More preferably, the conjugates of the present invention are selected from the group consisting of kanamycin-farnesyl conjugates and tobramycin-farnesyl conjugates.

In the present specification, the terms "conjugate" and "derivative conjugation" are used interchangeably. For example, a "tobramycin-farnesyl conjugate" may also be termed "tobramycin-farnesyl derivative conjugation" and vice versa.

As described above, covalent linkage of aminoglycoside moiety and terpenyl moiety may include an imine conjugation or an enamine conjugation. The following schemes show the structure of a farnesyl moiety upon conjugation to an aminoglycoside via an imine conjugation or via an enamine conjugation, respectively:

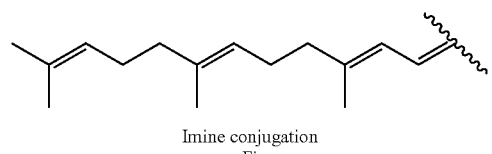

Imine conjugation
Fi

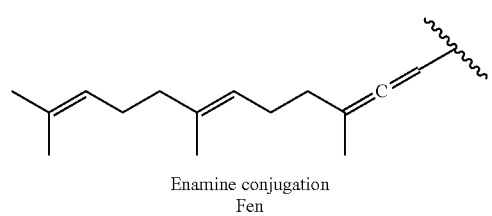

Enamine conjugation
Fen

The farnesyl moiety conjugated to an aminoglycoside via an imine conjugation is termed "Fi" in the present specification. The farnesyl moiety conjugated to an aminoglycoside via an enamine conjugation is termed "Fen" in the present specification.

Preferably, the conjugate of the present invention is selected from one or more of the group consisting of (i) tobramycin-farnesyl conjugates of the following formula

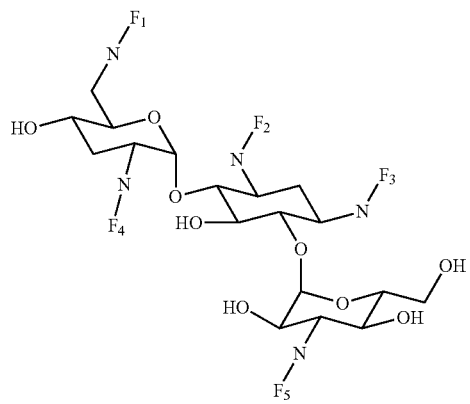

Tobramycin-FarnesylFormula wherein $F_1$, $F_2$, $F_3$, $F_4$, $F_5$ are —$H_2$ or Fi and wherein at least one of $F_1$, $F_2$, $F_3$, $F_4$, $F_5$ is Fi, for example the following tobramycin-farnesyl conjugate

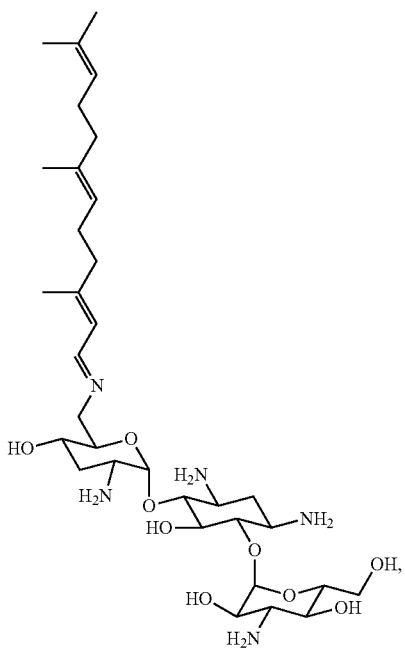

Tobramycin-Farnesylderivative conjugation (ii) kanamycin A-farnesyl conjugates of the following formula

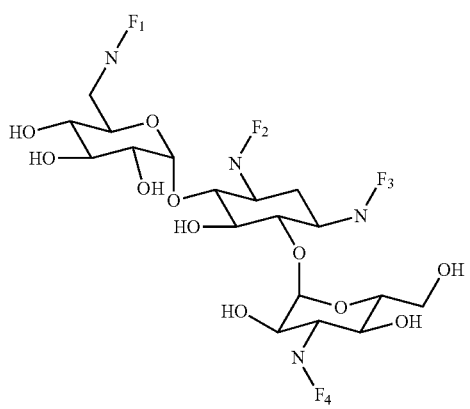

Kanamycin A-FarnesylFormula wherein $F_1$, $F_2$, $F_3$, $F_4$ are —$H_2$ or Fi and wherein at least one of $F_1$, $F_2$, $F_3$, $F_4$ is Fi, for example the following kanamycin A-farnesyl conjugate

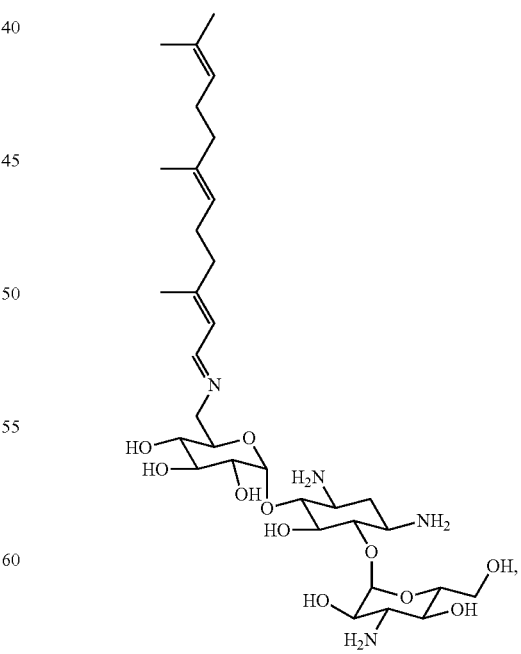

Kanamycin A-Farnesylderivative conjugation (iii) kanamycin B-farnesyl conjugates of the following formula

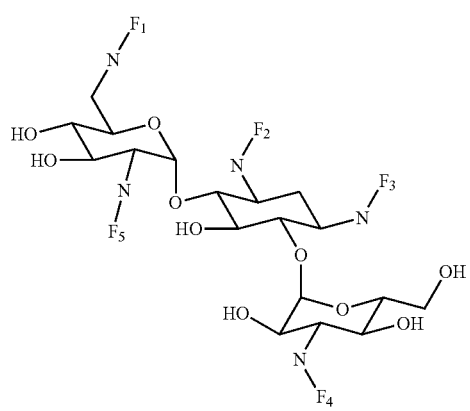

Kanamycin B-FarnesylFormula wherein $F_1$, $F_2$, $F_3$, $F_4$, $F_5$ are —$H_2$ or Fi and wherein at least one of $F_1$, $F_2$, $F_3$, $F_4$, $F_5$ is Fi, for example the following kanamycin B-farnesyl conjugate

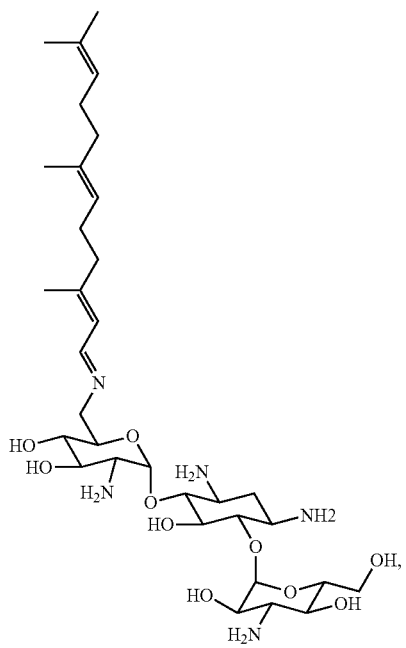

Kanamycin B-Farnesylderivative conjugation (iv) kanamycin C-farnesyl conjugates of the following formula

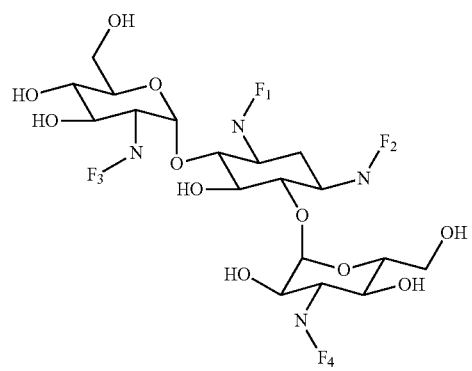

Kanamycin C-FarnesylFormula wherein $F_1$, $F_2$, $F_3$, $F_4$ are —$H_2$ or Fi and wherein at least one of $F_1$, $F_2$, $F_3$, $F_4$ is Fi, for example the following kanamycin C-farnesyl conjugate

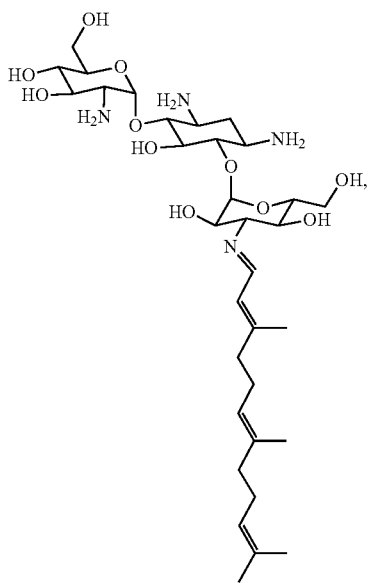

Kanamycin C-Farnesylderivative conjugation (v) 6'-OH kanamycin A-farnesyl conjugates of the following formula

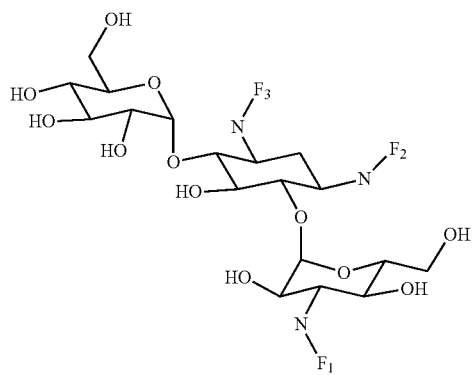

6'-OH-Kanamycin A-FarnesylFormula wherein $F_1$, $F_2$, $F_3$ are —$H_2$ or Fi and wherein at least one of $F_1$, $F_2$, $F_3$ is Fi, for example the following 6'-OH kanamycin A-farnesyl conjugate (vi) dibekacin-farnesyl conjugates of the following formula

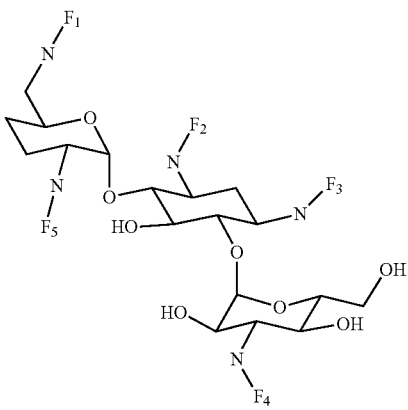

Dibekacin -FarnesylFormula wherein $F_1$, $F_2$, $F_3$, $F_4$, $F_5$ are —$H_2$ or Fi and wherein at least one of $F_1$, $F_2$, $F_3$, $F_4$, $F_5$ is Fi, for example the following dibekacin-farnesyl conjugate

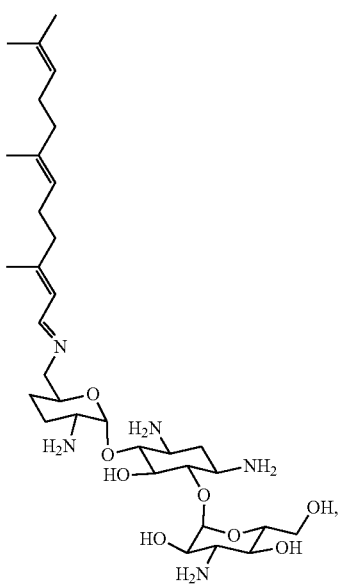

6'-OH-Kanamycin A-Farnesylderivative conjugation

Dibekacin-Farnesylderivative conjugation (vii) amikacin-farnesyl conjugates of the following formula
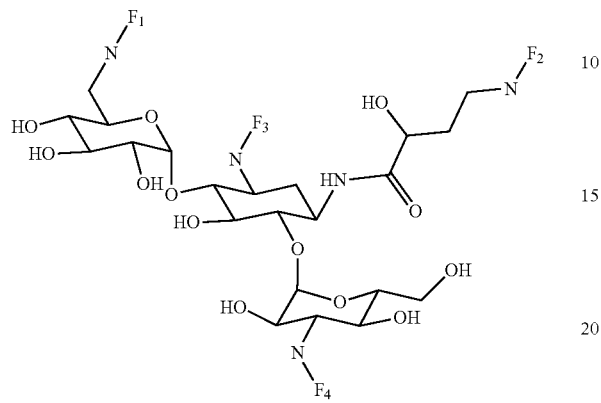
Amikacin-FarnesylFormula
wherein $F_1$, $F_2$, $F_3$, $F_4$ are —$H_2$ or Fi and wherein at least one of $F_1$, $F_2$, $F_3$, $F_4$ is Fi, for example the following amikacin-farnesyl conjugate
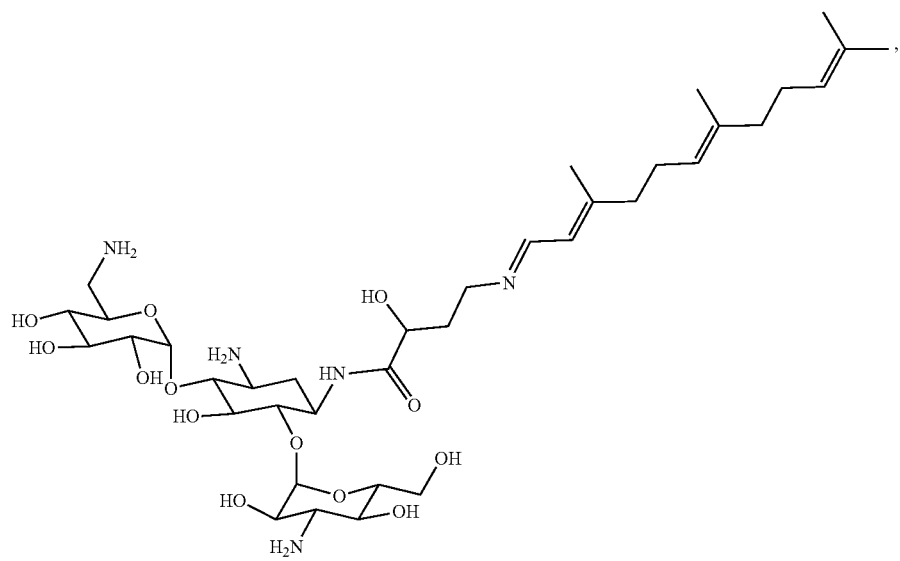
Amikacin-Farnesylderivative conjugation (viii) arbekacin-farnesyl conjugates of the following formula
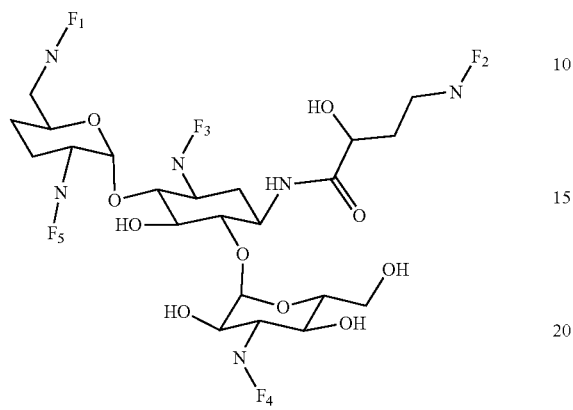
Arbekacin-FarnesylFormula
wherein $F_1$, $F_2$, $F_3$, $F_4$, $F_5$ are —$H_2$ or Fi and wherein at least one of $F_1$, $F_2$, $F_3$, $F_4$, $F_5$ is Fi, for example the following arbekacin-farnesyl conjugate
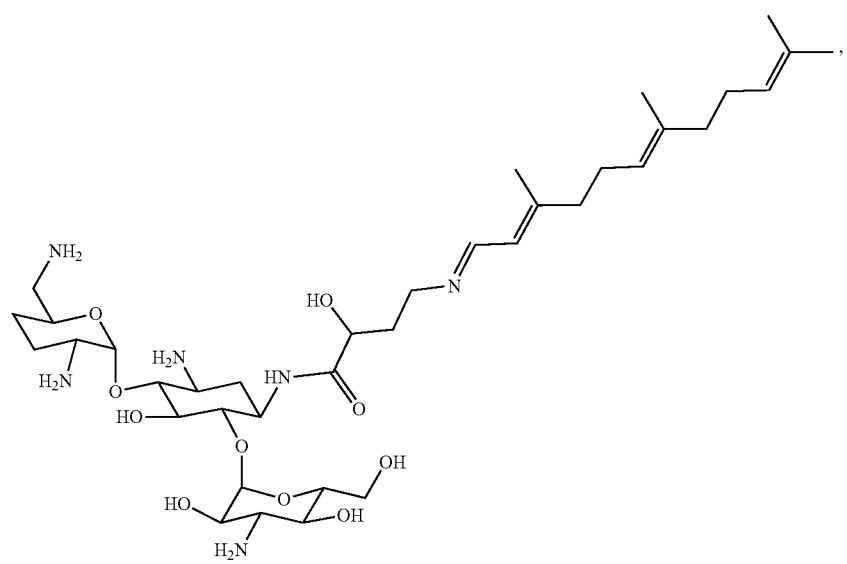
Arbekacin-Farnesylderivative conjugation (ix) gentamicin C1-farnesyl conjugates of the following formula

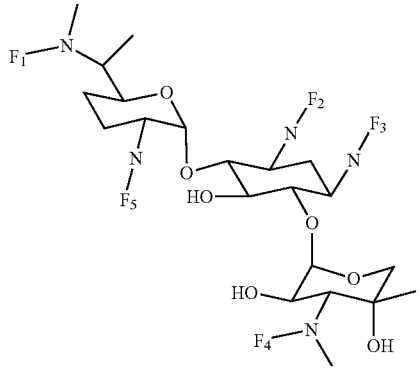

Gentamicin C1-FarnesylFormula wherein $F_2$, $F_3$, $F_5$ are —$H_2$ is Fi, wherein $F_1$, $F_4$ are —H or Fen and wherein at least one of $F_2$, $F_3$, $F_5$ is Fi, for example the following gentamicin C1-farnesyl conjugate

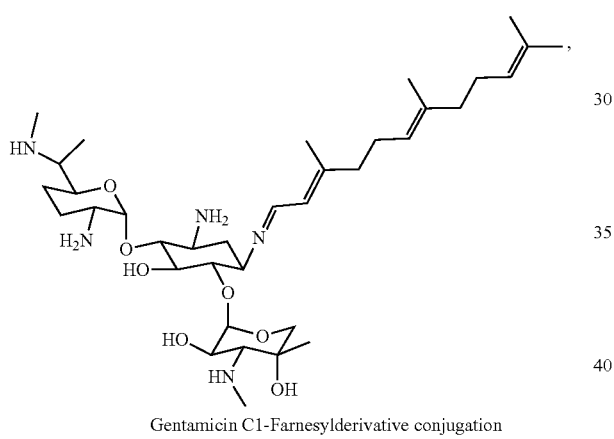

Gentamicin C1-Farnesylderivative conjugation (x) gentamicin C2-farnesyl conjugates of the following formula

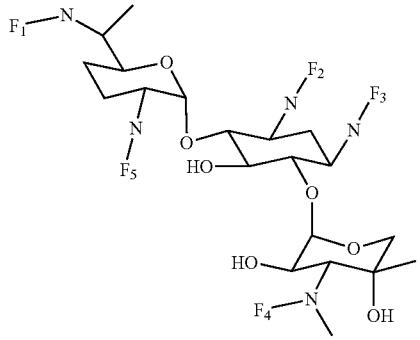

Gentamicin C2-FarnesylFormula wherein $F_1$, $F_2$, $F_3$, $F_5$ are —$H_2$ is Fi, wherein $F_4$ is —H or Fen and wherein at least one of $F_1$, $F_2$, $F_3$, $F_5$ is Fi, for example the following gentamicin C2-farnesyl conjugate

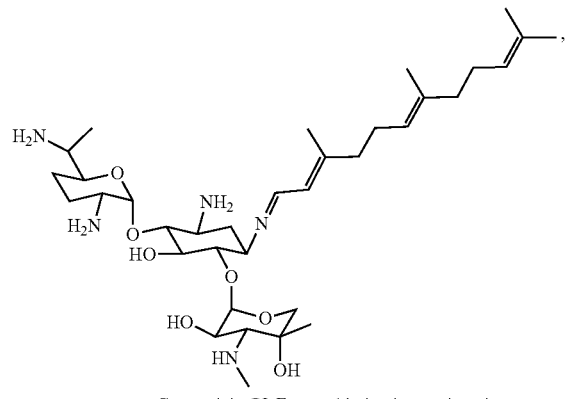

Gentamicin C2-Farnesylderivative conjugation (xi) gentamicin C1A-farnesyl conjugates of the following formula

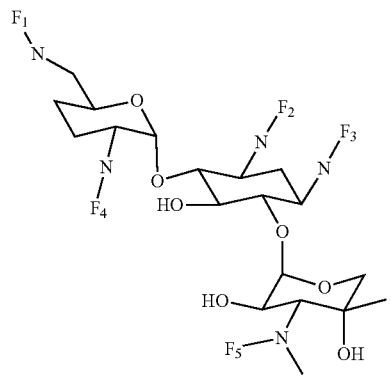

Gentamicin C1A-FarnesylFormula wherein $F_1$, $F_2$, $F_3$, $F_4$ are —$H_2$ is Fi, wherein $F_5$ is —H or Fen and wherein at least one of $F_1$, $F_2$, $F_3$, $F_4$ is Fi, for example the following gentamicin C1A-farnesyl conjugate

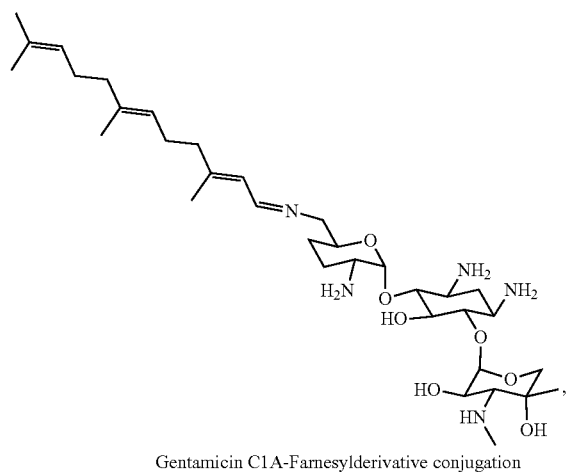 [SMILES: CNC1C(O)C(OC2C(N)CC(N)C(OC3OC(C/N=C/C=C(\C)CC/C=C(\C)CCC=C(C)C)CCC3N)C2O)OCC1(C)O]

Gentamicin C1A-Farnesylderivative conjugation (xii) geneticin (G418)-farnesyl conjugates of the following formula

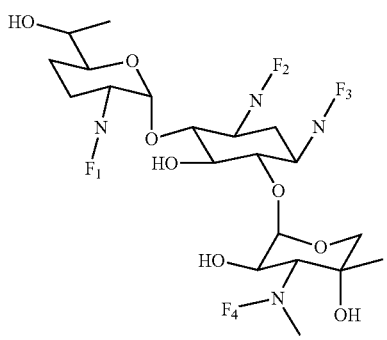

Geneticin(G418)-FarnesylFormula wherein $F_1$, $F_2$, $F_3$ are —$H_2$ is Fi, wherein $F_4$ is —H or Fen and wherein at least one of $F_1$, $F_2$, $F_3$ is Fi, for example the following geneticin (G418)-farnesyl conjugate

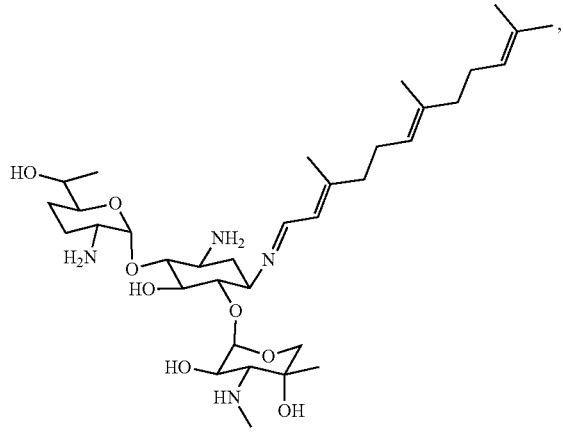

Geneticin(G418)-Farnesylderivative conjugation (xiii) netilmicin-farnesyl conjugates of the following formula

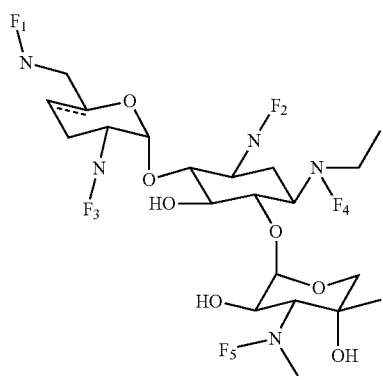

Netilmicin-FarnesylFormula wherein $F_1$, $F_2$, $F_3$ are —$H_2$ is Fi, wherein $F_4$, $F_5$ are —H or Fen and wherein at least one of $F_1$, $F_2$, $F_3$ is Fi, for example the following netilmicin-farnesyl conjugate

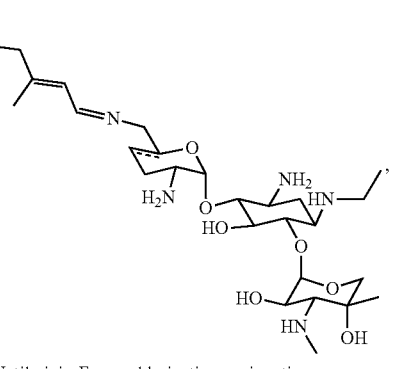

Netilmicin-Farnesylderivative conjugation (xiv) sisomicin-farnesyl conjugates of the following formula

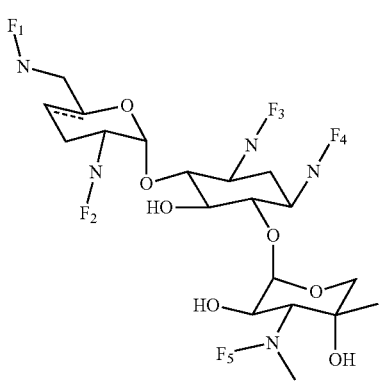

Sisomicin-FarnesylFormula wherein $F_1, F_2, F_3, F_4$ are —$H_2$ is Fi, wherein $F_5$ is —H or Fen and wherein at least one of $F_1, F_2, F_3, F_4$ is Fi, for example the following sisomicin-farnesyl conjugate

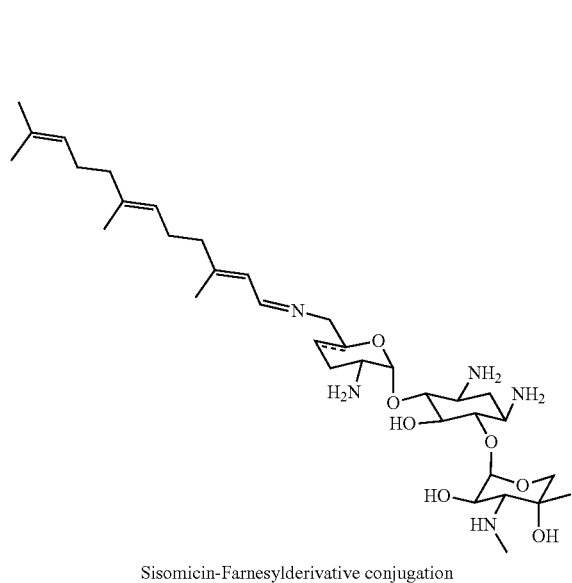

Sisomicin-Farnesylderivative conjugation (xv) verdamicin-farnesyl conjugates of the following formula

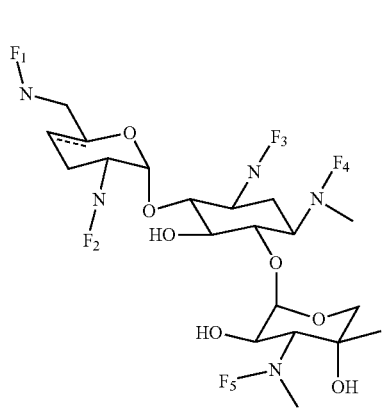

Verdamicin-FarnesylFormula wherein $F_1, F_2, F_3$ are —$H_2$ is Fi, wherein $F_4, F_5$ are —H or Fen and wherein at least one of $F_1, F_2, F_3$ is Fi, for example the following verdamicin-farnesyl conjugate

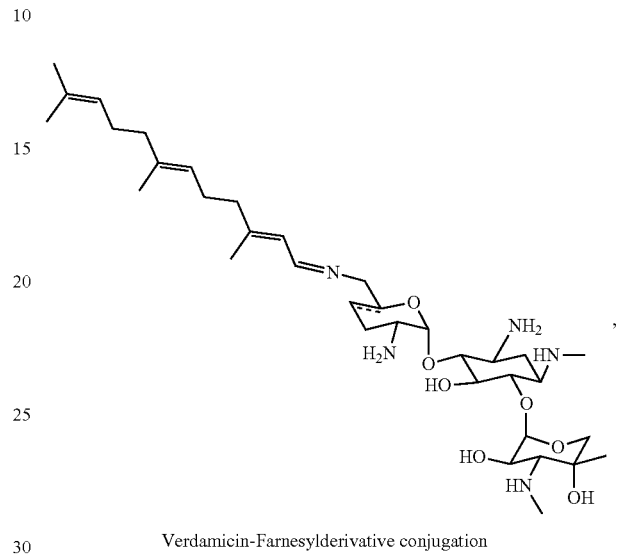

Verdamicin-Farnesylderivative conjugation (xvi) plazomicin-farnesyl conjugates of the following formula

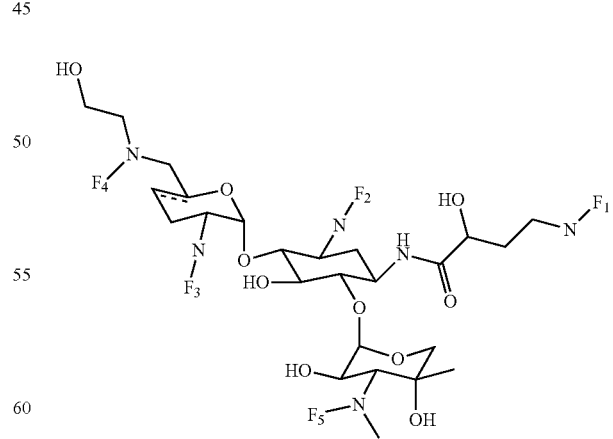

Plazomicin-FarnesylFormula wherein $F_1, F_2, F_3$ are —$H_2$ is Fi, wherein $F_4, F_5$ are —H or Fen and wherein at least one of $F_1, F_2, F_3$ is Fi, for example the following plazomicin-farnesyl conjugate

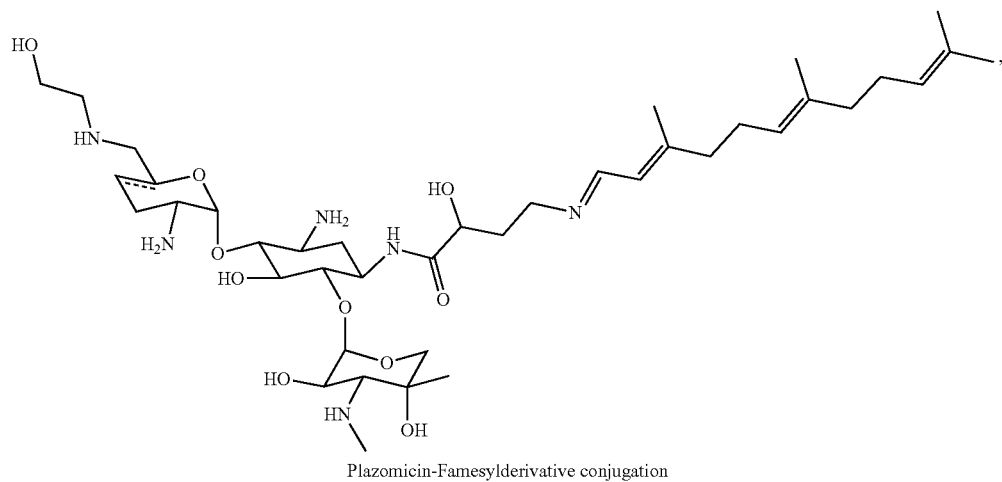
Plazomicin-Farnesylderivative conjugation
(xvii) isepamicin-farnesyl conjugates of the following formula
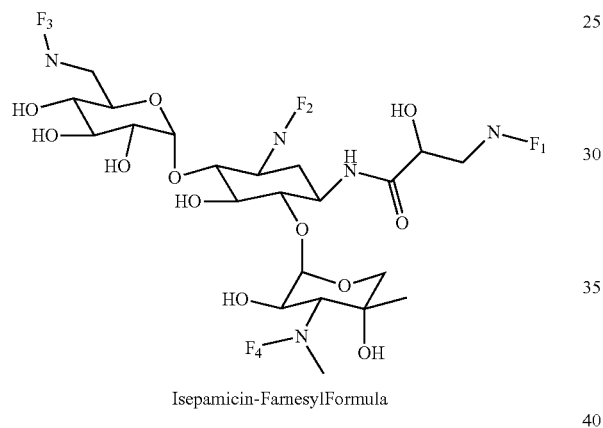
Isepamicin-FarnesylFormula
wherein $F_1$, $F_2$, $F_3$ are —$H_2$ is Fi, wherein $F_4$ is —H or Fen and wherein at least one of $F_1$, $F_2$, $F_3$ is Fi, for example the following isepamicin-farnesyl conjugate
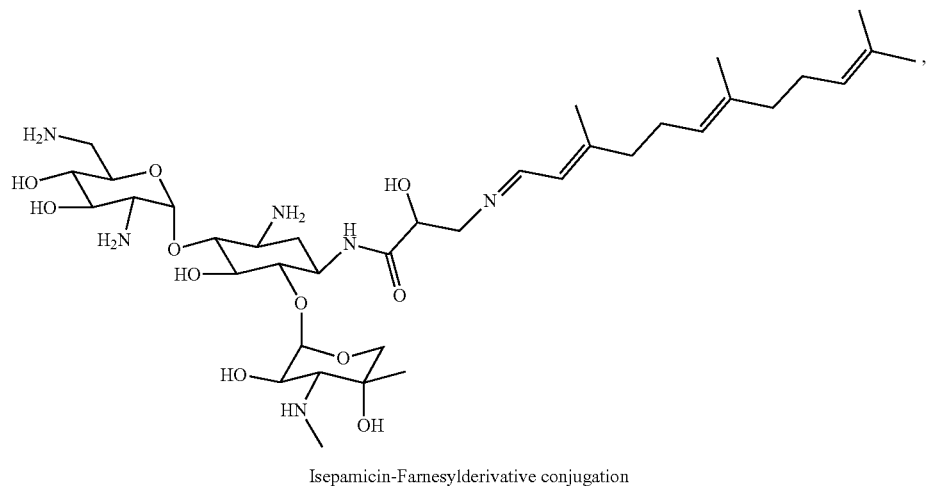 [SMILES: CNC1C(O)C(OC2C(NC(=O)C(O)CN=C/C=C(\C)CC/C=C(\C)CCC=C(C)C)CC(N)C(OC3OC(CN)C(O)C(O)C3N)C2O)OCC1(C)O]
Isepamicin-Farnesylderivative conjugation (xviii) neomycin B-farnesyl conjugates of the following formula

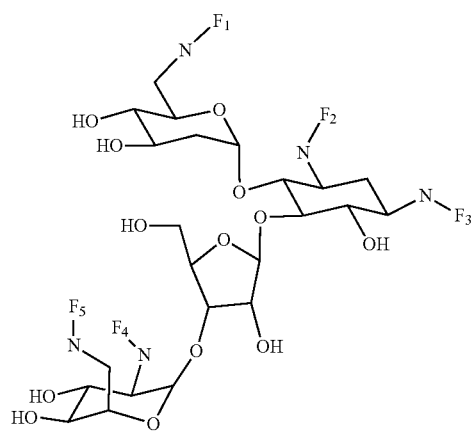

Neomycin B-FarnesylFormula wherein $F_1$, $F_2$, $F_3$, $F_4$, $F_5$ are —$H_2$ or Fi and wherein at least one of $F_1$, $F_2$, $F_3$, $F_4$, $F_5$ is Fi, for example the following neomycin B-farnesyl conjugate

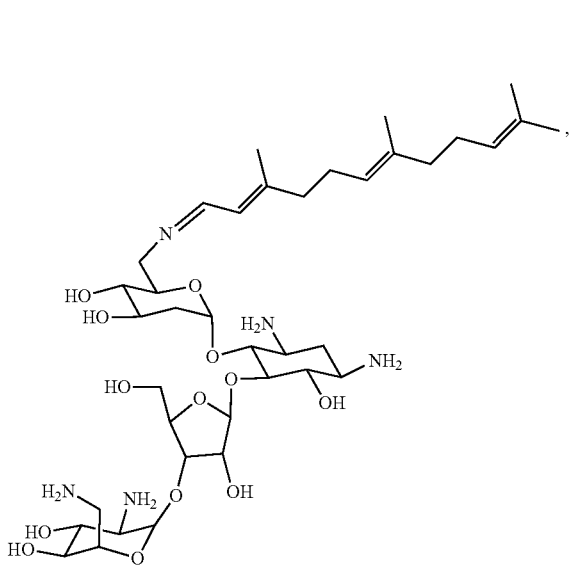

Neomycin B-Farnesylderivative conjugation (xix) neomycin C-farnesyl conjugates of the following formula

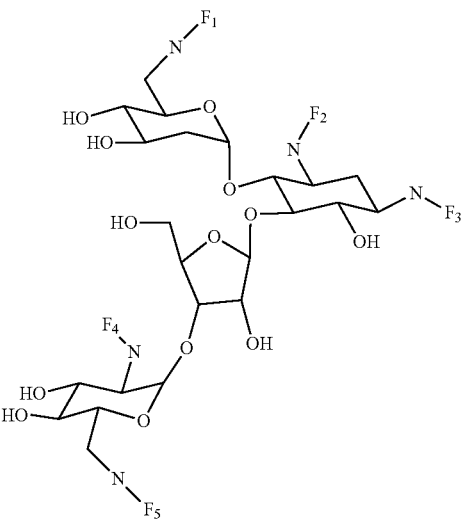

Neomycin C-FarnesylFormula wherein $F_1$, $F_2$, $F_3$, $F_4$, $F_5$ are —$H_2$ or Fi and wherein at least one of $F_1$, $F_2$, $F_3$, $F_4$, $F_5$ is Fi, for example the following neomycin C-farnesyl conjugate

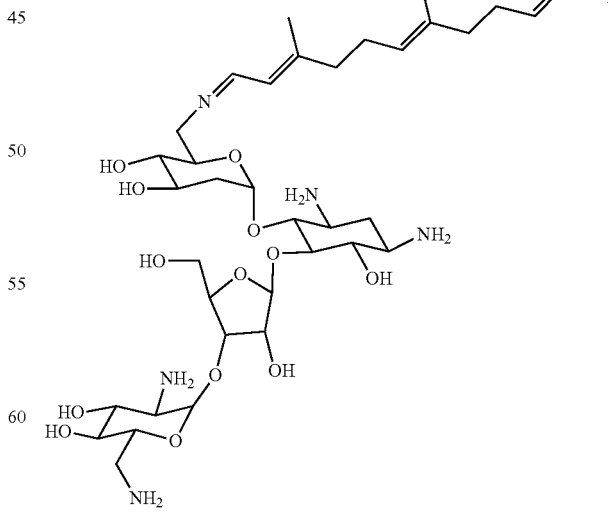

Neomycin C-Farnesylderivative conjugation (xx) neomycin E-farnesyl conjugates of the following formula

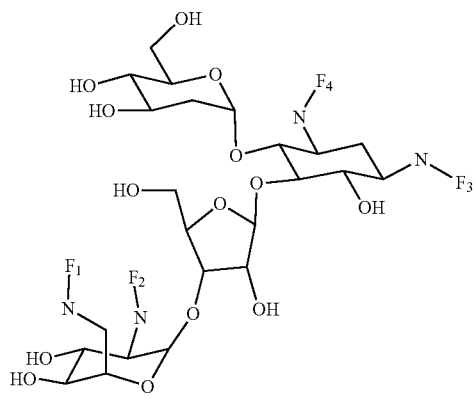

Paramomycin (Neomycin E)-FarnesylFormula wherein $F_1$, $F_2$, $F_3$, $F_4$ are —$H_2$ or Fi and wherein at least one of $F_1$, $F_2$, $F_3$, $F_4$ is Fi, for example the following neomycin E-farnesyl conjugate

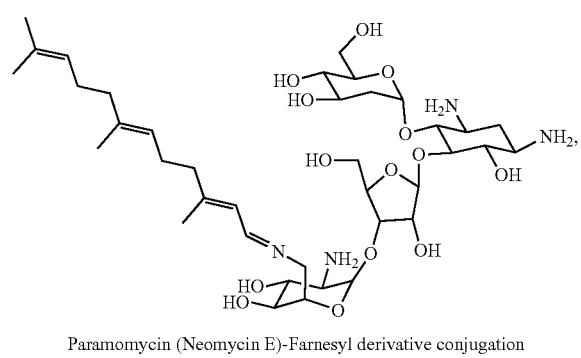 [SMILES: CC(C)=CCC/C(C)=C/CC/C(C)=C/C=N/CC1OC(OC2C(CO)OC(OC3C(O)C(N)CC(N)C3OC3CC(O)C(O)C(CO)O3)C2O)C(N)C(O)C1O]

Paramomycin (Neomycin E)-Farnesyl derivative conjugation (xxi) lividomycin B-farnesyl conjugates of the following formula

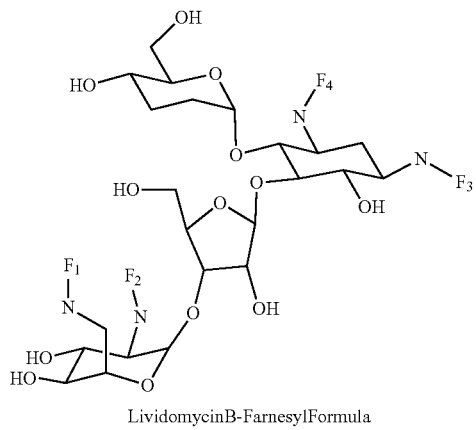

LividomycinB-FarnesylFormula wherein $F_1$, $F_2$, $F_3$, $F_4$ are —$H_2$ or Fi and wherein at least one of $F_1$, $F_2$, $F_3$, $F_4$ is Fi, for example the following lividomycin B-farnesyl conjugate

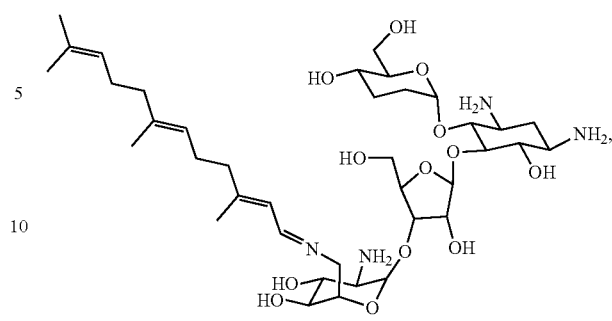

LividomycinB-Farnesylderivative conjugation (xxii) lividomycin A-farnesyl conjugates of the following formula

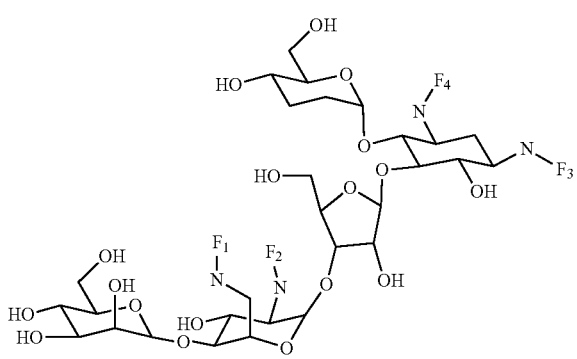

LividomycinA-FarnesylFormula wherein $F_1$, $F_2$, $F_3$, $F_4$ are —$H_2$ or Fi and wherein at least one of $F_1$, $F_2$, $F_3$, $F_4$ is Fi, for example the following lividomycin A-farnesyl conjugate

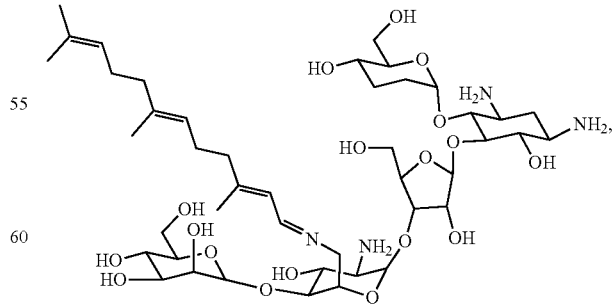

LividomycinA-Farnesylderivative conjugation (xxiii) butirosin B/A-farnesyl conjugates of the following formula

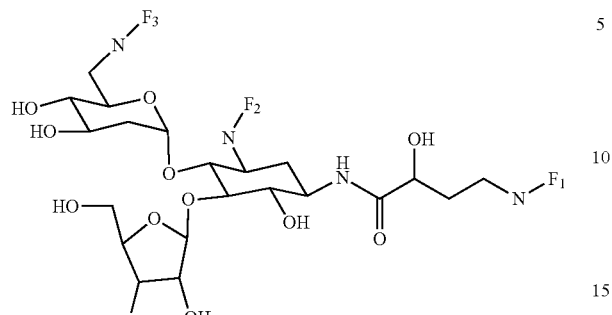

ButirosinB/A-FarnesylFormula wherein $F_1$, $F_2$, $F_3$ are —$H_2$ or Fi and wherein at least one of $F_1$, $F_2$, $F_3$ is Fi, for example the following butirosin B/A-farnesyl conjugate

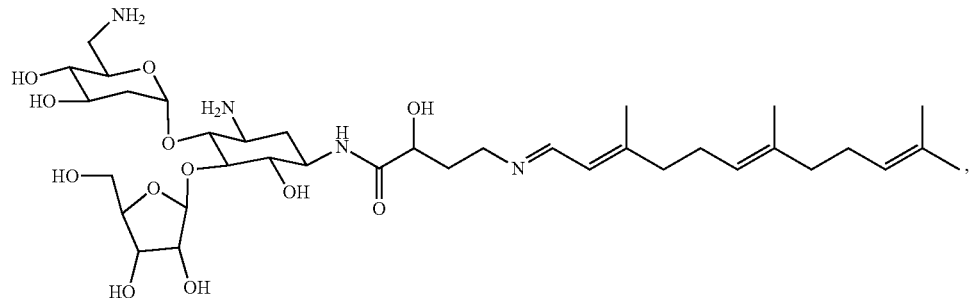

ButirosinB/A-Farnesylderivativeconjugation (xxiv) ribostamycin-farnesyl conjugates of the following formula

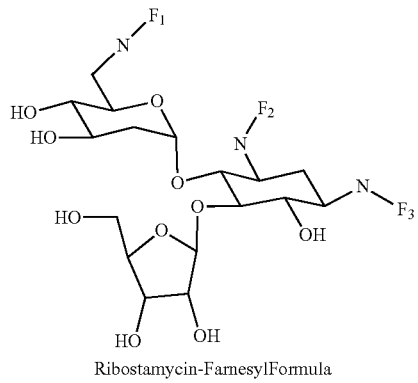

Ribostamycin-FarnesylFormula wherein $F_1$, $F_2$, $F_3$ are —$H_2$ or Fi and wherein at least one of $F_1$, $F_2$, $F_3$ is Fi, for example the following ribostamycin-farnesyl conjugate

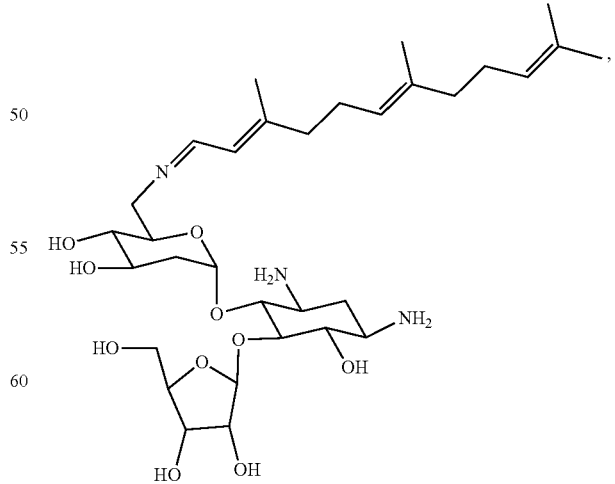

Ribostamycin-Farnesylderivative conjugation (xxv) streptomycin-farnesyl conjugates of the following formula (xxvi) 5'-hydroxystreptomycin-farnesyl conjugates of the following formula

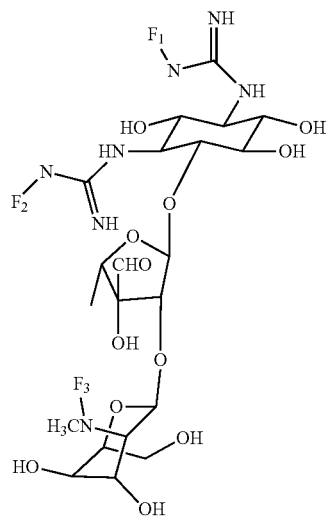

Streptomycin-FarnesylFormula

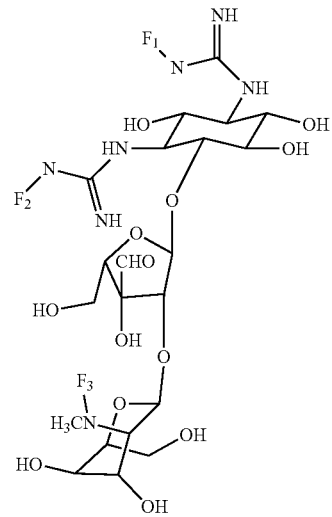

5'-hydroxystreptomycin-FarnesyFormula wherein $F_1$, $F_2$ are —$H_2$ is Fi, wherein $F_3$ is —H or Fen and wherein at least one of $F_1$, $F_2$ is Fi, for example the following streptomycin-farnesyl conjugate wherein $F_1$, $F_2$ are —$H_2$ is Fi, wherein $F_3$ is —H or Fen and wherein at least one of $F_1$, $F_2$ is Fi, for example the following 5'-hydroxystreptomycin-farnesyl conjugate

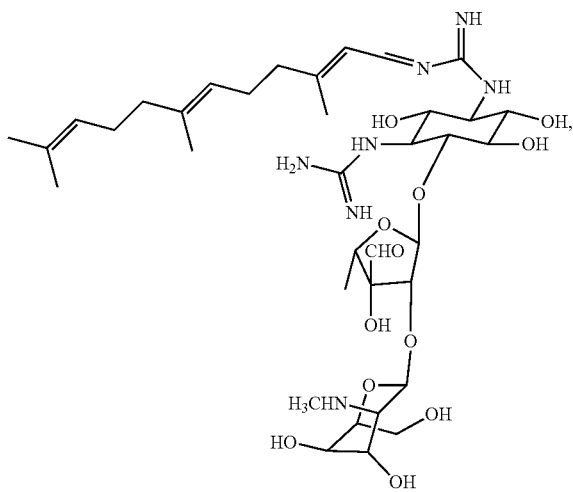

Streptomycin-Farnesylderivative conjugation

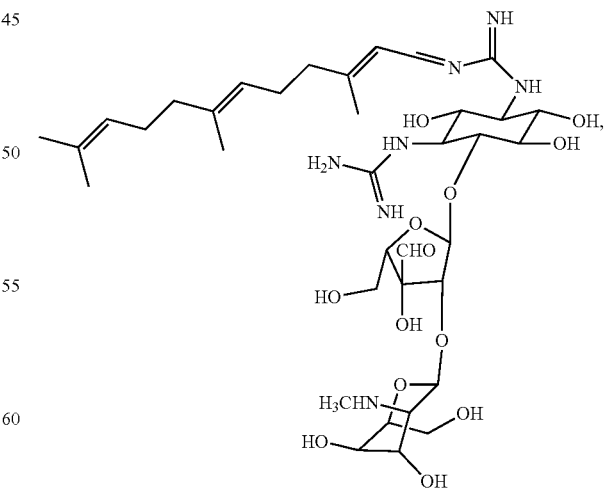

5'-hydroxystreptomycin-Farnesylderivative conjugation (xxvii) bluensomycin-farnesyl conjugates of the following formula

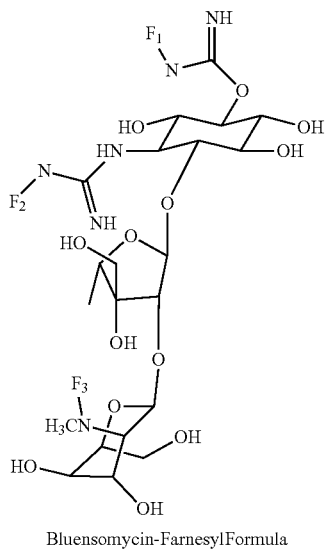

Bluensomycin-FarnesylFormula wherein $F_1$, $F_2$ are —$H_2$ is Fi, wherein $F_3$ is —H or Fen and wherein at least one of $F_1$, $F_2$ is Fi, for example the following bluensomycin-farnesyl conjugate

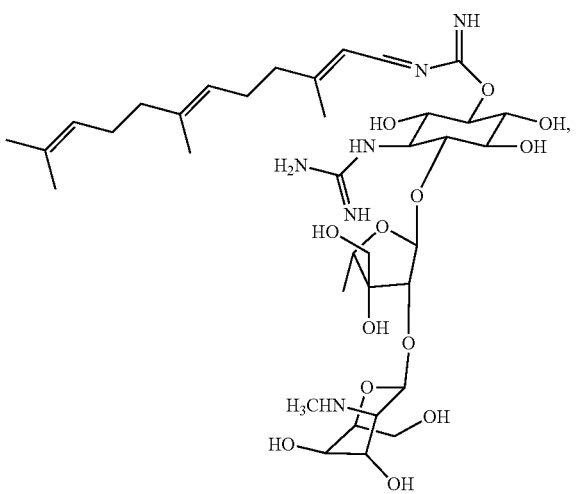

Bluensomycin-Farnesyderivative conjugation (xxviii) istamycin A-farnesyl conjugates of the following formula

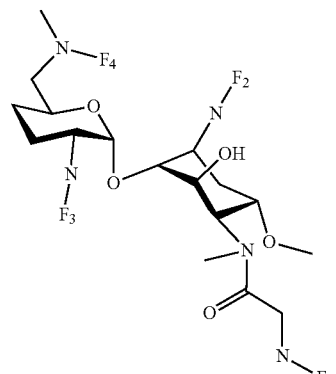

Istamycin A-FarnesylFormula wherein $F_1$, $F_2$, $F_3$ are —$H_2$ is Fi, wherein $F_4$ is —H or Fen and wherein at least one of $F_1$, $F_2$, $F_3$ is Fi, for example the following istamycin A-farnesyl conjugate

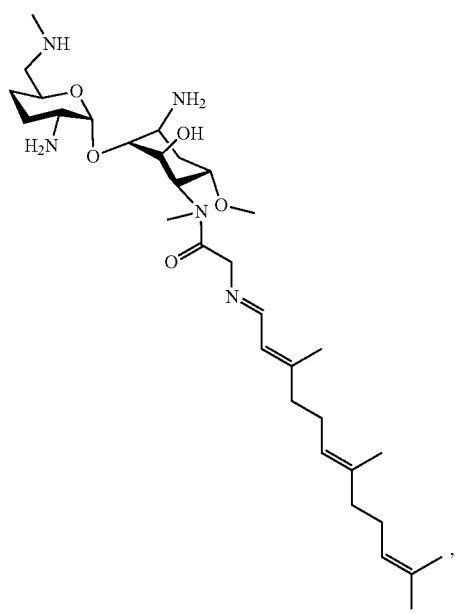

Istamycin A-Farnesylderivative conjugation (xxix) istamycin B-farnesyl conjugates of the following formula

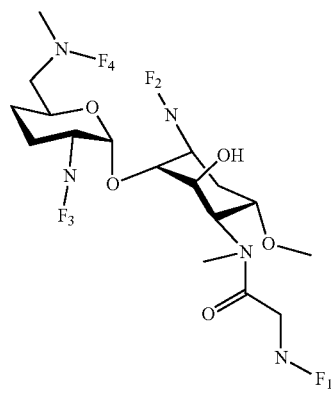

Istamycin A-FarnesylFormula wherein $F_1$, $F_2$, $F_3$ are —$H_2$ is Fi, wherein $F_4$ is —H or Fen and wherein at least one of $F_1$, $F_2$, $F_3$ is Fi, for example the following istamycin B-farnesyl conjugate (xxx) istamycin C-farnesyl conjugates of the following formula

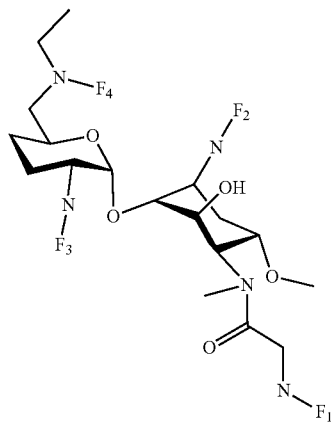

Istamycin C-Farnesyl Formula wherein $F_1$, $F_2$, $F_3$ are —$H_2$ is Fi, wherein $F_4$ is —H or Fen and wherein at least one of $F_1$, $F_2$, $F_3$ is Fi, for example the following istamycin C-farnesyl conjugate

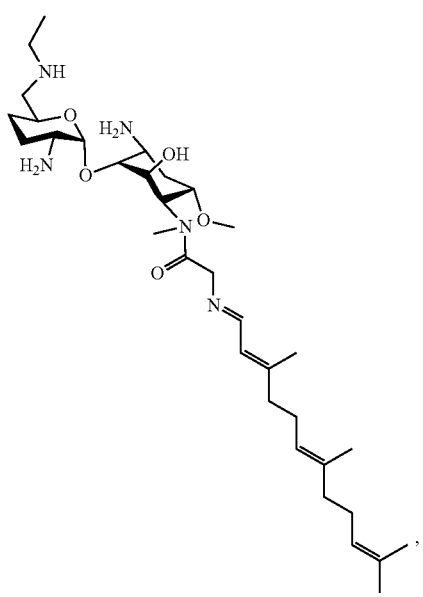

Istamycin C-Farnesylderivative conjugation

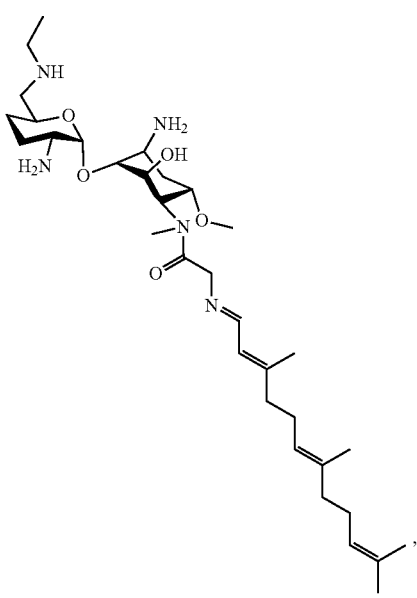

Istamycin C-Farnesylderivative conjugation (xxxi) fortimicin A (fortimicin B)-farnesyl conjugates of the following formula

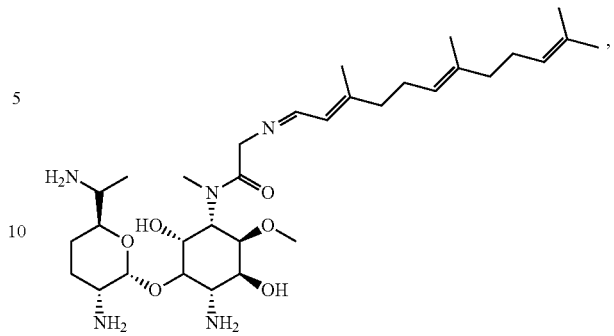

Fortimicin A (Fortimicin B)-Farnesylderivative conjugation

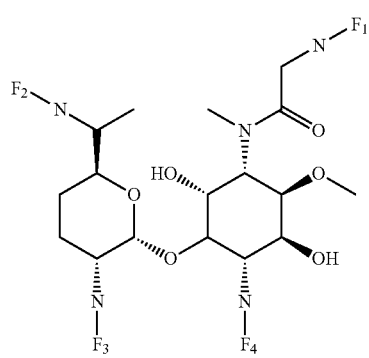

Fortimicin A (Fortimicin B)-FarnesylFormula wherein $F_1$, $F_2$, $F_3$, $F_4$ are —$H_2$ or Fi and wherein at least one of $F_1$, $F_2$, $F_3$, $F_4$ is Fi, for example the following fortimicin A (fortimicin B)-farnesyl conjugate (xxxii) apramycin-farnesyl conjugates of the following formula

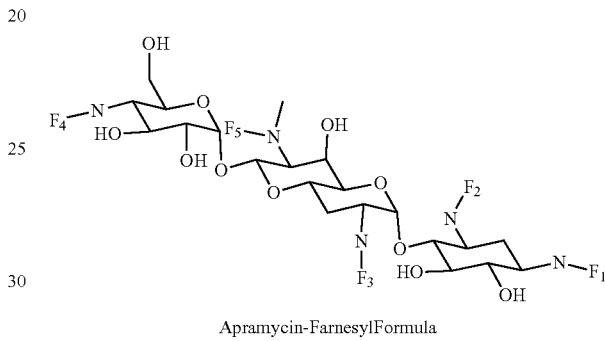

Apramycin-FarnesylFormula wherein $F_1$, $F_2$, $F_3$, $F_4$ are —$H_2$ is Fi, wherein $F_5$ is —H or Fen and wherein at least one of $F_1$, $F_2$, $F_3$, $F_4$ is Fi, for example the following apramycin-farnesyl conjugate

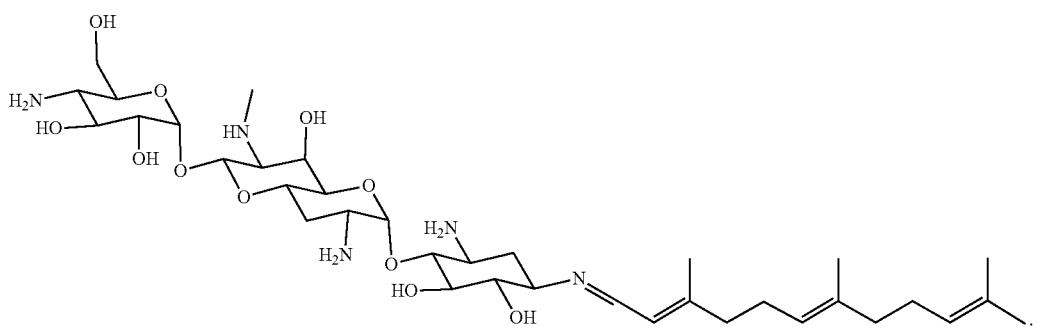

Apramycin-Farnesylderivative conjugation

As described above, the present invention also comprises conjugates, in which a terpenyl moiety linked to an aminoglycoside moiety via electrostatic interactions. A conjugate of the present invention comprising an aminoglycoside moiety and a terpenoid moiety linked via electrostatic interactions is exemplarily shown in FIG. 3.

Preferably, the electrostatic interactions involve positive charge on the aminoglycoside and negative charge on the terpenoid. Preferably, the negative charge on the terpenoid is mediated by an acid functional group. Therefore, in certain embodiments the terpenyl moiety preferably comprises at least one, more preferably exactly one acid functional group. Preferred acid functional groups are selected from the group consisting of carboxylic acid group, sulfonic acid group, phosphonic acid group, phosphoric acid group and hydrogen sulfate group. More preferably, the acid functional group is a carboxylic acid group.

Particularly preferred terpenyl moieties comprising acid functional groups are selected from the group consisting of farnesoic acid, farnesyl hydrogen sulfate, a-hydroxy farnesyl phosphonic acid, farnesyl monophosphate, farnesyl diphosphate and farnesyl triphosphate. Such terpenyl moieties are shown in FIG. 4. More preferably, the terpenyl moiety comprising acid functional group is selected from the group consisting of farnesoic acid and farnesyl hydrogen sulfate.

Preferably, the conjugate of the present invention is cleavable into a pharmaceutically active aminoglycoside and a pharmaceutically active terpenoid. Preferred pharmaceutical activity of the terpenoid is quorum sensing inhibitory activity. Preferably, the pharmaceutically active terpenoid is farnesol or a derivative thereof, in particular farnesal and/or farnesoic acid. Release of aminoglycoside and terpenoid from the conjugate may occur upon cleavage, in particular pH-sensitive cleavage of a covalent linkage between the aminoglycoside moiety and the terpenyl moiety, in particular covalent linkage via an imine group or via an enamine group. According to the present invention, the term "cleavage" of the conjugate also comprises separation of aminoglycoside moiety and terpenyl moiety that had been linked via electrostatic interactions.

The conjugate of the present invention is preferably present in form of nano-assemblies having an average diameter of from 50 to 800 nm, more preferably of from 100 to 500 nm, more preferably of from 150 to 300 nm. Preferably, the average diameter is determined by transmission electron microscopy (TEM) or by dynamic light scattering (DLS). More preferably, the average diameter is determined by DLS.

The present invention also relates to a nano-assembly comprising the conjugate of the present invention. Preferably, the nano-assembly has an average diameter of from 50 to 800 nm, more preferably of from 100 to 500 nm, more preferably of from 150 to 300 nm. Preferably, the average diameter is determined by TEM or by DLS. More preferably, the average diameter is determined by DLS. Preferably, the nano-assembly of the present invention has a hydrophilic shell (preferably formed by the aminoglycoside moiety) and a hydrophobic core (preferably formed by the terpenyl moiety). The nano-assembly of the invention is preferably "single-layered". In other words, the conjugates of the invention do preferably not form bilayers.

Representative TEM images of nano-assemblies of the present invention are shown in FIG. 5.

In certain embodiments of the present invention, the nano-assembly may comprise at least one further active substance in addition to the aminoglycoside moiety and to the at least one terpenyl moiety. However, the present invention also comprises embodiments, in which the nano-assembly does not comprise any further active substances in addition to the aminoglycoside moiety and to the at least one terpenyl moiety.

The nano-assemblies of the present invention may be used as carrier system, in particular for hydrophobic substances. Such hydrophobic substances may be loaded into the core of the nano-assemblies. For example, in certain embodiments it may be desired to further increase the quorum sensing inhibitory activity. In such embodiments, the nano-assemblies may be loaded with quorum sensing inhibitors, in particular with quorum sensing inhibitors selected from farnesol and derivatives thereof, quinolone and derivatives thereof (in particular 2-heptyl-6-nitro-4-oxo-1,4-dihydroquinoline-3-carboxamide), as well as mixture of one or more of those quorum sensing inhibitors.

Some preferred embodiments relate to nano-assemblies of the present invention loaded with farnesol.

Some preferred embodiments relate to nano-assemblies of the present invention loaded with farnesol derivatives having the formula

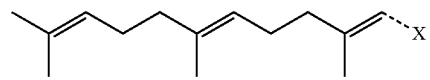

Farnesol derivative formular wherein X is selected from the group consisting of

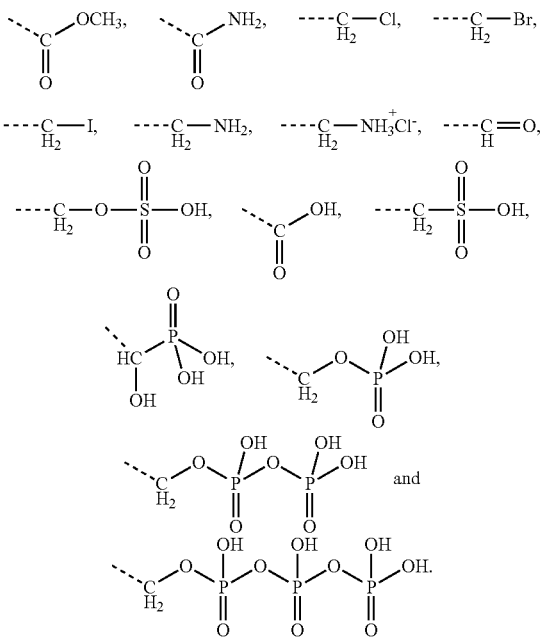

Some preferred embodiments relate to nano-assemblies of the present invention loaded with farnesol derivatives having the formula

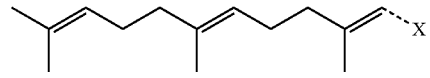

Farnesol derivative formular wherein X is selected from the group consisting of

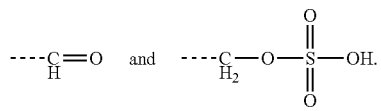

Some preferred embodiments relate to nano-assemblies of the present invention loaded with farnesol derivatives having the formula

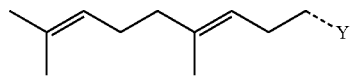

wherein Y is selected from the group consisting of

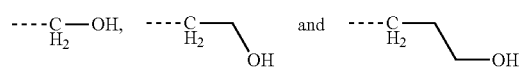

Some preferred embodiments relate to nano-assemblies of the present invention loaded with farnesol derivatives having the formula

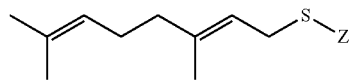

wherein Z is selected from the group consisting of

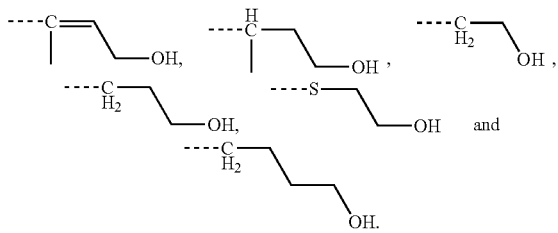

Some preferred embodiments relate to nano-assemblies of the present invention loaded with farnesol derivatives having the formula

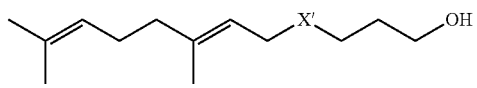

wherein X' is selected from the group consisting of S, Se and SCH$_2$.

Some preferred embodiments relate to nano-assemblies of the present invention loaded with farnesol derivatives having the formula

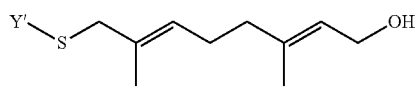

wherein Y' is selected from the group consisting of n-butyl, isobutyl, n-pentyl, benzyl and phenyl.

Some preferred embodiments relate to nano-assemblies of the present invention loaded with farnesol and/or with at least one farnesol derivative described above. Particularly preferred embodiments relate to nano-assemblies of the present invention loaded with farnesol and with at least one farnesol derivative having the formula

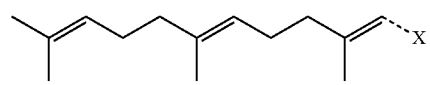

Farnesol derivative formular wherein X is selected from the group consisting of

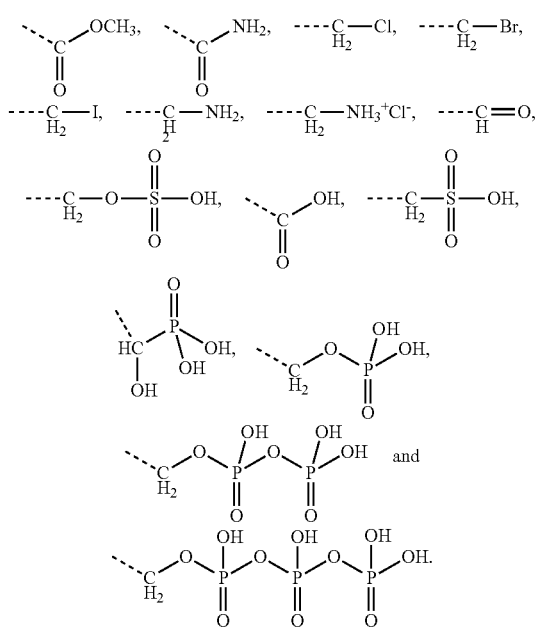

Even more preferred embodiments relate to nano-assemblies of the present invention loaded with farnesol and with at least one farnesol derivative having the formula

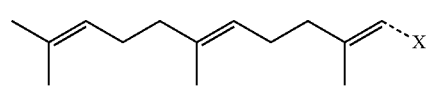

Farnesol derivative formular wherein X is selected from the group consisting of

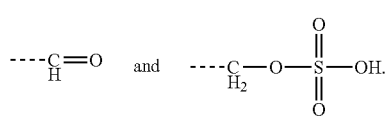

More preferably, nano-assemblies of the invention are loaded with farnesol or with farnesal or with farnesyl hydrogen sulfate.

In certain embodiments, nano-assemblies of the present invention may comprise both aminoglycosides that are linked to a terpenyl moiety by a covalent linkage, such as linkage by an imine group, and aminoglycosides that are linked to a terpenyl moiety via electrostatic interactions, in particular to a terpenyl moiety comprising an acid functional group.

The present invention also relates to the conjugate or the nano-assembly of the present invention for use in therapy.

The present invention also relates to the conjugate or the nano-assembly of the present invention for use in treatment of infectious diseases. Preferably, the infectious disease is responsive to the pharmaceutical activity of the aminoglycoside. In embodiments, in which the terpenoid has pharmaceutical activity, it is preferable that the infectious disease is responsive to the pharmaceutical activity of the terpenoid. Particularly preferably, the infectious disease is responsive to the pharmaceutical activity of the aminoglycoside and to the pharmaceutical activity of the terpenoid. Preferably, the infectious disease is selected from the group consisting of respiratory infections including those associated with cystic fibrosis, lower respiratory tract infections, bacterial eye infections such as conjunctivitis, in particular infections involving aerobic bacteria, bacterial infections of the eyelids, conjunctiva and cornea, urinary tract infections, skin and skin structure infections, infections involving aerobic gram-negative bacteria, such as *Pseudomonas, Acinetobacter*, and *Enterobacter*, infections with multi-drug resistant bacteria, in particular with multi-drug resistant gram-negative bacteria, for example infections of wounds, and infections with multi-drug resistant Enterobacteriaceae.

The present invention also relates to a pharmaceutical composition comprising the conjugate or the nano-assembly of the present invention. Preferably, the pharmaceutical composition is an aqueous solution. The pharmaceutical composition may comprise pharmaceutically acceptable excipients. Pharmaceutically acceptable excipients are for example sugar or polymers such as poloxamers, for example F68 poloxamer. Pharmaceutical compositions of the present invention may be administered by different routes of application. Preferred routes of application are selected from the group consisting of (i) topical administration, including inhalational administration (pulmonary or respiratory), ophthalmic administration (application into the eyes), epicutaneous administration (application onto the skin), otic administration (application into the ears) and buccal (application onto mucosal membrane), nasal (application into the nose), vaginal or any other mucosal administration,
(ii) oral administration,
(iii) intravenous administration, and
(iv) intramuscular administration.

In order to achieve particularly high drug concentration at the site of infection and to reduce systemic exposure and related adverse effects, topical administration is most preferred.

The present invention also relates to a method for preparing a conjugate comprising an aminoglycoside moiety and at least one terpenyl moiety as well as to a method for preparing a nano-assembly comprising such conjugate. In particular, the method of the present invention is a method for preparing a conjugate of the present invention, thus a conjugate comprising an aminoglycoside moiety and at least one terpenyl moiety, wherein the terpenyl moiety has at most 20 carbon atoms. The present invention also relates to a method for preparing a nano-assembly comprising such conjugate. Preferably, the method comprises the following steps:

a) Mixing an aminoglycoside with a terpenoid in a solvent,
b) Incubating the mixture,
c) Isolating the conjugate or the nano-assembly.

Preferably, the method consists of steps a) to c) above. This is particularly advantageous because it is very efficient to prepare the conjugate or the nano-assembly with such a low number of steps. Furthermore, a very high yield is supported by the low number of steps.

According to step a) of the method of the present invention, an aminoglycoside is mixed with a terpenoid. Preferably, the molar ratio of aminoglycoside to terpenoid in the mixture is from 1:0.9 to 1:10, more preferably from 1:1 to 1:5, more preferably about 1:1.1. Low molar ratios of aminoglycoside to terpenoid are accompanied by high proportions of terpenoid. This is particularly advantageous in embodiments in which a further increased QSI activity mediated by the terpenoid, in particular by farnesol and derivatives thereof, is desired.

The terpenoid comprises at most 20 carbon atoms. Preferably, the terpenoid comprises at least 10 carbon atoms. Preferably, the terpenoid comprises at most 15 carbon atoms. Preferably, the terpenoid comprises from 10 to 15 carbon atoms. Particularly preferably, the terpenoid comprises exactly 10 carbon atoms or exactly 15 carbon atoms. Preferably, the terpenoid is selected from the group consisting of geraniol, farnesol and derivatives thereof. Preferably, the terpenoid is a sesquiterpenoid. Particularly preferably, the terpenoid is farnesol or a derivative thereof.

Preferably, the farnesol derivative is a farnesol derivative of the formula

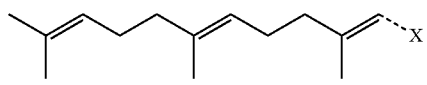

Farnesol derivative formular wherein X is selected from the group consisting of

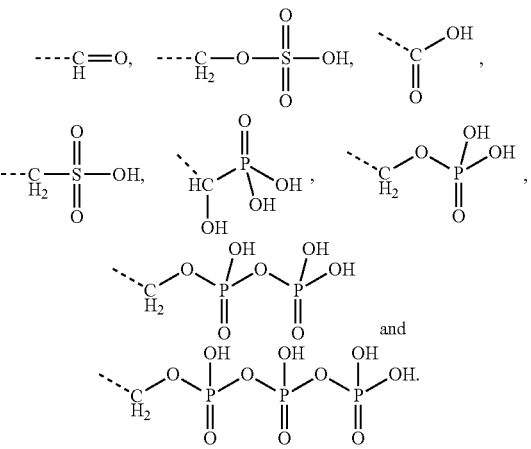

More preferably, X is selected from the group consisting of

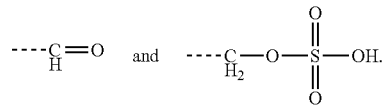

Even more preferably, X is

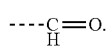

In embodiments in which X is

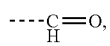

the aminoglycoside moiety and the terpenyl moiety are preferably linked via a covalent linkage, such as linkage by an imine group. In embodiments in which X is one of

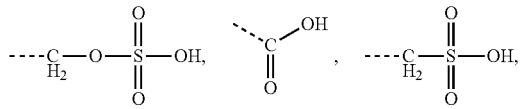

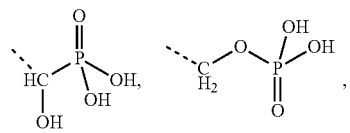

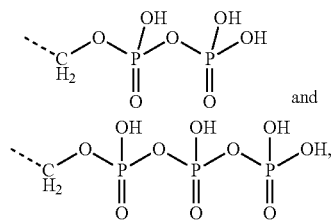

the aminoglycoside moiety and the terpenyl moiety are preferably linked via electrostatic interactions. In embodiments in which the terpenoid is farnesol, the aminoglycoside moiety and the terpenyl moiety are preferably linked via electrostatic interactions.

Preferably, the farnesol derivative is selected from the group consisting of farnesal, farnesoic acid, farnesyl hydrogen sulfate, a-hydroxy farnesyl phosphonic acid, farnesyl monophosphate, farnesyl diphosphate and farnesyl triphosphate. More preferably, the farnesyl derivative is selected from the group consisting of farnesal, farnesoic acid and farnesyl hydrogen sulfate. Even more preferably, the farnesyl derivative is farnesal.

Preferred embodiments relate to a nano-assembly comprising at least one conjugate comprising a farnesol derivative in which X is

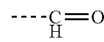

and at least one conjugate comprising farnesol or a farnesol derivative in which X is one of

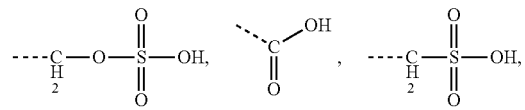

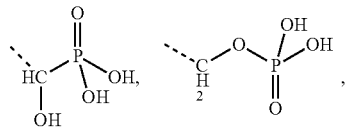

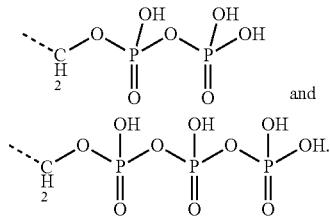

Such nano-assemblies comprise at least one conjugate in which the linkage between the aminoglycoside moiety and the farnesyl moiety is pH-sensitive and at least one conjugate in which the aminoglycoside moiety and the farnesyl moiety are linked via electrostatic interactions. More preferably, a nano-assembly of the invention comprises at least one conjugate comprising a farnesol derivative in which X is

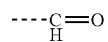

and at least one conjugate comprising farnesol or a farnesol derivative in which X is

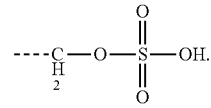

Preferably, a nano-assembly of the invention comprises at least one conjugate comprising farnesal.

Preferably, the aminoglycoside is selected from the group consisting of aminoglycosides of kanamycin class, aminoglycosides of gentamicin class, aminoglycosides of neomycin class, aminoglycosides of streptomycin class and aminoglycosides of istamycin class. More preferably, the aminoglycoside is selected from the group consisting of aminoglycosides of kanamycin class, aminoglycosides of gentamicin class and aminoglycosides of neomycin class. Particularly preferably, the aminoglycoside is an aminoglycoside of kanamycin class.

According to the present invention, aminoglycosides of kanamycin class are characterized by the following formula:

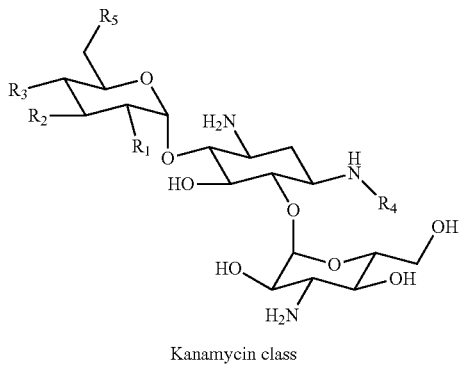

Kanamycin class wherein $R_1$ is OH or $NH_2$, $R_2$ is H or OH, $R_3$ is H or OH, $R_4$ is H or (S)-4-amino-2-hydroxybutiryl and $R_5$ is OH or $NH_2$.

Particularly preferably, aminoglycosides of kanamycin class are selected from the group consisting of kanamycin A, kanamycin B, kanamycin C, 6'-OH-kanamycin A, dibekacin, tobramycin, amikacin and arbekacin. Particularly preferred aminoglycosides of kanamycin class are kanamycin A and tobramycin.

According to the present invention, aminoglycosides of gentamicin class are characterized by the following formula:

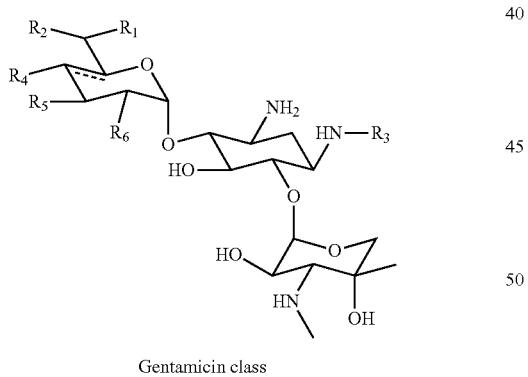

Gentamicin class wherein $R_1$ is H or $CH_3$, $R_2$ is OH, $NH_2$, $NHCH_3$ or $NHCH_2CH_2OH$, $R_3$ is H, $CH_3$, $CH_2CH_3$, (S)-4-amino-2-hydroxybutiryl or 3-amino-2-hydroxypropanyl, $R_4$ is H or OH, $R_5$ is H or OH and $R_6$ is OH or $NH_2$ and wherein the dashed line indicated an optional double bond.

Particularly preferably, aminoglycosides of gentamicin class are selected from the group consisting of gentamicin C1, gentamicin C2, gentamicin C1A, geneticin (G418), netilmicin, sisomicin, verdamicin, plazomicin and isepamicin.

According to the present invention, aminoglycosides of neomycin class are characterized by the following formula:

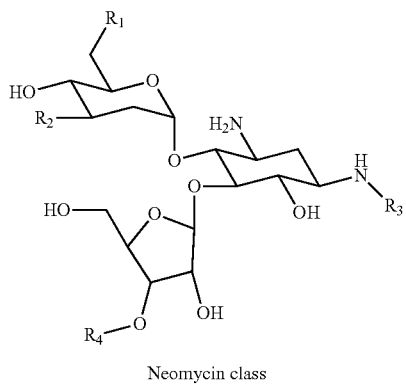

Neomycin class wherein $R_1$ is OH or $NH_2$, $R_2$ is H or OH, $R_3$ is H or (S)-4-amino-2-hydroxybutiryl, $R_4$ is H or a DAG (2,6-diamino-2,6-deoxy-alpha-L-glucopyranosyl) moiety of the following formula:

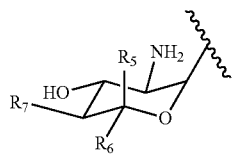

wherein $R_5$ is H or $CH_2NH_2$, $R_6$ is H or $CH_2NH_2$ and $R_7$ is OH or a mannose moiety of the following formula:

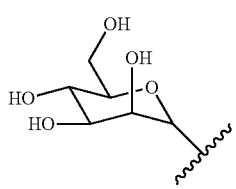 [SMILES: *C1OC(CO)C(O)C(O)C1O]

Particularly preferably, aminoglycosides of neomycin class are selected from the group consisting of neomycin B, neomycin C, paramomycin (neomycin E), lividomycin B, lividomycin A, butirosin B/A and ribostamycin.

According to the present invention, aminoglycosides of streptomycin class are characterized by the following formula:

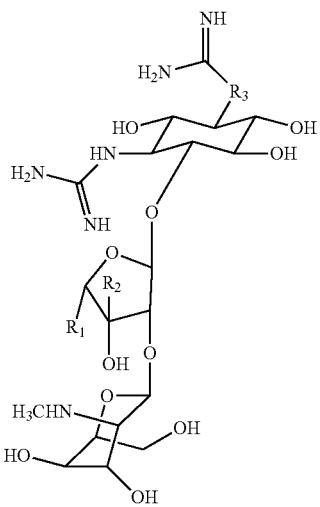

wherein $R_1$ is $CH_3$ or $CH_2OH$, $R_2$ is CHO or $CH_2OH$ and $R_3$ is —NH— or –O—.

Particularly preferably, aminoglycosides of streptomycin class are selected from the group consisting of streptomycin, 5'-hydroxystreptomycin and bluensomycin.

According to the present invention, aminoglycosides of istamycin class are characterized by the following formula:

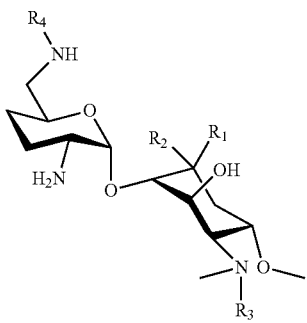

wherein $R_1$ is H or $NH_2$, $R_2$ is H or $NH_2$, $R_3$ is H, $COCH_2NH_2$, $COCH_2NHCHO$ or $COCH_2NHCONH_2$ and $R_4$ is $CH_3$ or $CH_2CH_3$.

Particularly preferably, aminoglycosides of istamycin class are selected from the group consisting of istamycin A (sannamycin), istamycin B, istamycin C, istamycin $A_0$, istamycin $B_0$, istamycin $C_0$, istamycin $A_1$, istamycin $B_1$, istamycin $C_1$ and istamycin $A_2$.

Preferably, the aminoglycoside is selected from the group consisting of kanamycin A, kanamycin B, kanamycin C, 6'-OH-kanamycin A, dibekacin, tobramycin, amikacin, arbekacin, gentamicin C1, gentamicin C2, gentamicin C1A, geneticin (G418), netilmicin, sisomicin, verdamicin, plazomicin, isepamicin, neomycin B, neomycin C, paramomycin (neomycin E), lividomycin B, lividomycin A, butirosin B/A, ribostamycin, streptomycin, 5'-hydroxystreptomycin, bluensomycin, istamycin A (sannamycin), istamycin B, istamycin C, istamycin $A_0$, istamycin $B_0$, istamycin $C_0$, istamycin $A_1$, istamycin $B_1$, istamycin $C_1$, istamycin $A_2$, apramycin, fortimicin A and fortimicin B. More preferably, the aminoglycoside moiety is selected from the group consisting of tobramycin, amikacin, plazomicin, neomycin B, gentamicin, kanamycin, netilmicin, sisomicin and dibekacin. More preferably, the aminoglycoside is selected from the group consisting of kanamycin and tobramycin. The term "gentamicin" is used as a collective term for gentamicin C1, gentamicin C2 and gentamicin C1A in the present specification. The term "kanamycin" is used as a collective term for kanamycin A, kanamycin B, kanamycin C and 6'-OH-kanamycin A in the present specification. More preferably, the aminoglycoside is selected from the group consisting of kanamycin A and tobramycin.

Preferably, the method of the present invention comprises the step of preparing an aminoglycoside solution and/or a terpenoid solution prior to mixing the aminoglycoside with the terpenoid according to step a) of the method of the present invention.

Preferably, an aminoglycoside solution is prepared by dissolving the aminoglycoside in solvent A. Aminoglycosides are generally comparably hydrophilic compounds. Therefore, preferably aqueous solvents are used as solvent A for preparation of the initial aminoglycoside solution. Preferably, solvent A is an aqueous medium, in particular water. Preferably, the concentration of aminoglycoside in the aminoglycoside solution is from 0.1 to 10.0 mg/ml, more preferably from 0.5 to 5.0 mg/ml, more preferably from 1.0 to 3.0 mg/ml. Preferably, the pH of the initial aminoglycoside solution is adjusted to a pH of from 6.0 to 7.5, more preferably of from 6.5 to 7.0.

Preferably, a terpenoid solution is prepared by dissolving the terpenoid in solvent B. Terpenoids are generally less hydrophilic as compared to aminoglycosides. Therefore, preferably less polar solvents (in comparison to the aqueous solvent used for preparation of the initial aminoglycoside solution) are used as solvent B for preparation of the terpenoid solution. The polarity of a solvent can be described by the polarity index. In the present specification, it is referred to the polarity index according to Paul C. Sadek, The HPLC Solvent Guide, 2nd Edition, Wiley-Interscience, 2002. Higher values of the polarity index indicate a higher polarity of the solvent. For example, water has a polarity index of 9.0. Preferably, solvent B has a polarity index of from 3.0 to 7.5, more preferably of from 3.5 to 6.5, more preferably of from 3.9 to 6.0. Preferably, solvent B is selected from the group consisting of ethanol, acetone, tetrahydrofuran (THF), acetonitrile, methanol, isopropyl alcohol, dioxane, dimethyl formamide (DMF) and dimethylsulfoxide (DMSO). More preferably, solvent B is selected from the group consisting of ethanol, acetone, THF, acetonitrile, methanol, isopropyl alcohol and dioxane. More preferably, solvent B is selected from the group consisting of ethanol, acetone, THF and isopropyl alcohol. More preferably, solvent B is ethanol.

The inventors found that it is advantageous if solvent C is added to the initial aminoglycoside solution before mixing the aminoglycoside with the terpenoid. Preferably, solvent C is less polar in comparison to solvent A used for preparation of the initial aminoglycoside solution. Preferably, solvent C has a polarity index of from 3.0 to 7.5, more preferably of from 3.5 to 6.5, more preferably of from 3.9 to 6.0. Solvent C is preferably selected from the group consisting of ethanol, acetone, THF, acetonitrile, methanol, isopropyl alcohol, dioxane, DMF and DMSO. More preferably, solvent C is selected from the group consisting of ethanol, acetone, THF, acetonitrile, methanol, isopropyl alcohol and dioxane. More preferably, solvent C is selected from the group consisting of ethanol, acetone, THF and isopropyl alcohol. More preferably, solvent C is ethanol. Preferably, solvent C is added to the initial aminoglycoside solution until the volume ratio of the solvent A to the solvent C is from 1:0.3 to 1:1, more preferably from 1:0.5 to 1:0.9, more preferably about 1:0.8. The aminoglycoside solution obtained by addition of solvent C is termed "solvent-adjusted aminoglycoside solution" within the present specification.

Preferably, the solvent B used for preparation of the terpenoid solution and solvent C used for solvent-adjustment of the initial aminoglycoside solution are the same solvent. Particularly preferably, ethanol is used as solvent B for preparation of the terpenoid solution and as solvent C for solvent-adjustment of the initial aminoglycoside solution.

Preferably, the aminoglycoside is mixed with the terpenoid according to step a) of the method of the present invention by adding the terpenoid solution into the solvent-adjusted aminoglycoside solution. Preferably, the resulting solution (mixture) is stirred during mixing of aminoglycoside and terpenoid.

The mixture of aminoglycoside and terpenoid is incubated according to step b) of the method of the present invention. Preferably, the mixture is incubated for 0.5 to 30 hours, more preferably for 1 to 24 hours, more preferably for 2 to 18 hours, more preferably for 3 to 15 hours. Preferably, the mixture is stirred during incubation. The conjugate comprising an aminoglycoside moiety and at least one terpenyl moiety is formed during the incubation. Preferably, the pH of the mixture is adjusted to a pH of 7.0 to 8.5, more preferably of 7.0 to 7.8 after 0.5 to 5 hours, more preferably 1 to 4 hours, more preferably 2 to 3.5 hours of incubation. Adjustment of the pH is advantageous for further stabilization of the conjugate.

The conjugate or the nano-assembly is isolated according to step c) of the method of the present invention.

Preferably, the step of isolating the conjugate or the nano-assembly comprises a step of removing the solvents B and C. Preferably, solvents B and C are removed by evaporation in a vacuum rotary evaporator. Different methods of removal are preferred in embodiments, in which DMF and/or DMSO are used as solvents B and/or C. In particular, DMF is preferably removed by membrane dialysis. DMSO is preferably removed by freeze drying. In embodiments, in which a hydrophobic substance is to be loaded into the nano-assembly, the hydrophobic substance is preferably added to the conjugate prior to removal of solvents B and C.

Preferably, the step of isolating the conjugate or the nano-assembly comprises a step of removing non-conjugated aminoglycosides. Preferably, non-conjugated aminoglycosides are removed by membrane dialysis, in particular by membrane dialysis in water. In certain embodiments of the present invention, membrane dialysis is used for removing both DMF and non-conjugated aminoglycosides.

Preferably, the step of isolating the conjugate or the nano-assembly comprises both a step of removing solvents B and C and a step of removing non-conjugated aminoglycosides. Preferably, the step of removing non-conjugated aminoglycosides is performed subsequent to the step of removing solvents B and C.

The present inventors found that the nano-assembly of the present invention forms spontaneously upon removal of solvents B and C. Hence, the nano-assembly is preferably isolated according to step c) of the method of the present invention by removing solvents B and C and removing non-conjugated aminoglycosides.

The conjugate of the present invention may be isolated prior to or subsequent to formation of the nano-assembly.

In embodiments, in which the conjugate is isolated prior to formation of the nano-assembly, removal of solvents B and C is preferably avoided. In such embodiments, the conjugate is preferably isolated by removal of non-conjugated aminoglycosides. Preferably, non-conjugated aminoglycosides are removed by membrane dialysis, in particular by membrane dialysis in a mixture of solvent A with solvents B and C that corresponds to the mixture of solvents that the conjugate has been formed in during incubation according to step b) of the method of the present invention. Optionally, a hydrophobic substance may be added to the obtained isolated conjugate in order to load the hydrophobic substance into the nano-assembly to be formed.

The present invention also comprises embodiments in which the conjugate is isolated subsequent to formation of the nano-assembly. As described above, the nano-assembly forms spontaneously upon removal of solvents B and C. The nano-assembly has to be disassembled in order to isolate the conjugate. Preferably, the nano-assembly is disassembled by removal of solvent A. Preferably, solvent A is removed by freeze-drying. The isolated conjugate is preferably stored at a temperature of at most −5° C., more preferably at most −10° C., more preferably at most −15° C., more preferably at most −20° C. In certain embodiments of the present invention, in particular in embodiments in which DMSO is used as solvent B and C, freeze-drying is used for removing solvents A, B and C.

The present invention also comprises embodiments in which the nano-assembly is formed from the stored conjugate. For this purpose, the stored conjugate is preferably dissolved in a mixture of solvent A and solvent B. Preferably, the ratio (v:v) of solvent A to solvent B is from 1:5 to 5:1, more preferably from 1:2 to 2:1, more preferably about 1:1. Optionally, a hydrophobic substance may be added to the dissolved conjugate in order to load the hydrophobic substance into the nano-assembly to be formed. The nano-assembly is formed by removal of solvent B. Preferably, solvent B is removed by evaporation in a vacuum rotary evaporator. Optionally, trace amounts of solvent B and/or non-conjugated aminoglycosides may be removed for isolation of the nano-assembly. Removal of trace amounts of solvent B and/or non-conjugated aminoglycosides is preferably done by membrane dialysis, in particular by membrane dialysis in water.

As described above, the terpenyl moiety is conjugated to an amino group on the aminoglycoside. Importantly, aminoglycosides comprise more than one amino group. The present inventors found that there is no bias for certain amine groups to be conjugated preferentially. Rather, conjugation occurs as a statistical process so that the conjugates of the present invention may be obtained as a mixture of different conjugates having terpenyl moieties conjugated to different amine groups. Notably, the different conjugates of such a mixture do not differ with regard to their pharmaceutical activity because the pharmaceutically active substances are generated upon cleavage of the conjugate and identical aminoglycoside and terpenoid molecules are obtained upon cleavage of the different molecules independent of the amine group of the aminoglycoside to which the terpenyl moiety was conjugated. Hence, as the different constituents of the mixture are pharmacodynamically comparable such a mixture may be used without further separation of the different conjugates. However, the method of the present invention may comprise an additional step of isolating distinct conjugates from the obtained mixture of conjugates, wherein such distinct conjugates have the terpenyl moiety conjugated to a specific amino group of the aminoglycoside. The skilled person is aware of suitable methods for isolation of such distinct conjugates.

The method of the present invention is characterized by a very high yield. Preferably, the conversion yield is at least 90%, more preferably at least 95%, more preferably at least 98%, more preferably at least 99%, more preferably at least 99.9%, more preferably even 100%. The method of the present invention is based on the reaction of an aminoglycoside with a terpenoid in a solvent. The aminoglycoside reacts to a certain percentage (x %) while (1–x) % remain unreacted. Likewise, the terpenoid reacts to a certain percentage (y %) while (1–y) % remain unreacted. The term "conversion yield" refers to the percentage x % for x>y and to the percentage y % for y>x. If x=y, the conversion yield can be determined as x % or as y %. For example, if at least one of the reactants (aminoglycoside and terpenoid (in particular Farnesal)) has reacted to 100% and not been remained in the reacting solution, the conversion yield is 100%.

Preferably, the isolated yield is at least 80%, more preferably at least 85%, more preferably at least 90%, more preferably at least 92%, more preferably at least 93%, more preferably at least 94%, more preferably at least 95%. The isolated yield is calculated as the fraction of the amount of substance of the isolated product and the amount of substance that could have been obtained theoretically based on the amount of substance of the input reagents.

The method of the present invention may comprise an additional step of loading at least one, preferably exactly one additional substance, in particular an additional active substance, into the nano-assembly. The additional substance may be hydrophilic or hydrophobic. The step of loading the additional substance into the nano-assembly preferably differs depending on the hydrophobicity of the substance to be loaded into the nano-assembly. Hydrophilic substances are preferably loaded onto the nano-assembly after formation of the nano-assembly. In particular, hydrophilic substances are preferably loaded onto the surface (shell part) of the nano-assembly. In contrast, hydrophobic substances are preferably loaded during formation of the nano-assembly, particularly preferably by co-precipitation into the core of the nano-assembly.

A hydrophilic substance, in particular a hydrophilic active substance, is preferably loaded onto the nano-assembly by adding the hydrophilic substance to the already formed nano-assembly and incubating the mixture for 0.5 to 30 hours, more preferably for 1 to 24 hours, more preferably for 2 to 18 hours, more preferably for 3 to 15 hours in a polar solvent, in particular in solvent A. Preferred hydrophilic substances are selected from the group consisting of enzymes (in particular alginase) and nucleases (in particular DNase I).

For loading hydrophobic substances, in particular hydrophobic active substances, these substances are preferably added to the conjugate prior to formation of the nano-assembly. As described above, the nano-assembly of the present invention forms spontaneously upon removal of the less polar solvent(s) (solvent B and/or C). Thus, hydrophobic substances to be loaded into the nano-assembly are preferably added to the conjugate prior to the indicated removal of the less polar solvent. Preferably, the hydrophobic substance is dissolved in a mixture of solvent A and solvent B. Preferably, the ratio (v:v) of solvent A to solvent B is from 1:5 to 5:1, more preferably from 1:2 to 2:1, more preferably about 1:1. Subsequently, the dissolved hydrophobic substance is preferably added to the isolated conjugate of the present invention obtained as described above. Thus, a mixture comprising the conjugate and the hydrophobic substance is preferably obtained. Preferably, the nano-assembly is then formed in the resulting mixture of conjugate and hydrophobic substance by removal of the less polar solvent(s) (solvent B and/or C). As the hydrophobic substance has strongly reduced solubility or is even insoluble in the remaining polar solvent (solvent A), the hydrophobic substance is preferably loaded into the forming nano-assembly by co-precipitation with the conjugate, in particular into the core of the nano-assembly.

Removal of the less polar solvent(s) is preferably done by evaporation in a vacuum rotary evaporator. Optionally, trace amounts of less polar solvent(s) and/or non-conjugated aminoglycosides may be removed by membrane dialysis, in particular by membrane dialysis in water.

EXAMPLES

Example 1: Preparation of the Conjugate

In the following, preparation of inventive conjugates will be exemplarily described. The described conjugates comprise an aminoglycoside (kanamycin A or tobramycin) moiety and a farnesyl moiety. However, it should be noted that the present invention is not restricted to these specific conjugates. Rather, the aminoglycoside moiety may be any aminoglycoside moiety in accordance with the present invention. Likewise, the farnesyl moiety may be replaced by any terpenyl moiety.

Figure 1:
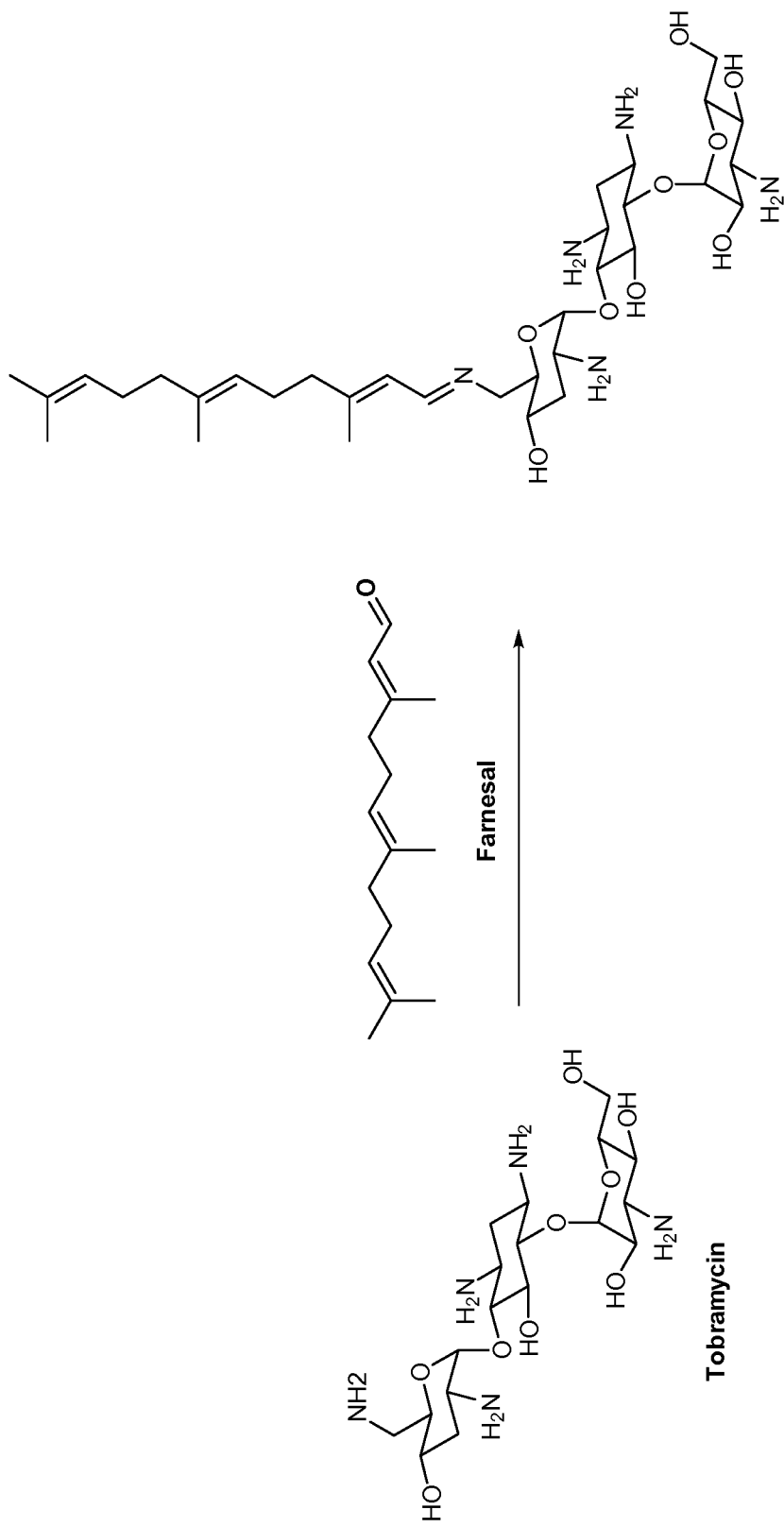
FIG. 1 schematically shows the preparation of a conjugate of the present invention comprising a tobramycin moiety and a farnesyl moiety. Notably, the preparation of the conjugate is essentially a single step preparation.
Figure 2:
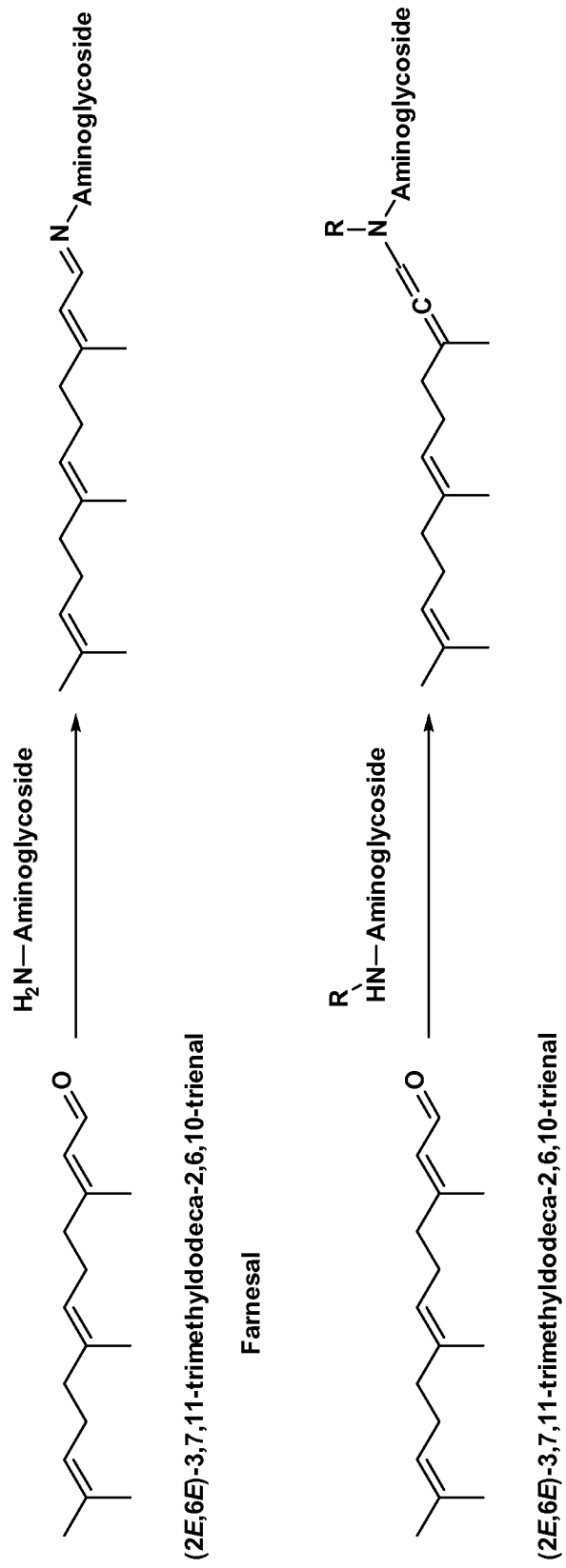
FIG. 2 schematically shows covalent linkage of farnesal to an aminoglycoside. When farnesal is bound to a primary amine group on the aminoglycoside, the farnesyl moiety is linked to the aminoglycoside moiety via an imine group (top). When farnesal is bound to a secondary amine group on the aminoglycoside, the farnesyl moiety is linked to the aminoglycoside moiety via an enamine group (bottom).
Figure 3:
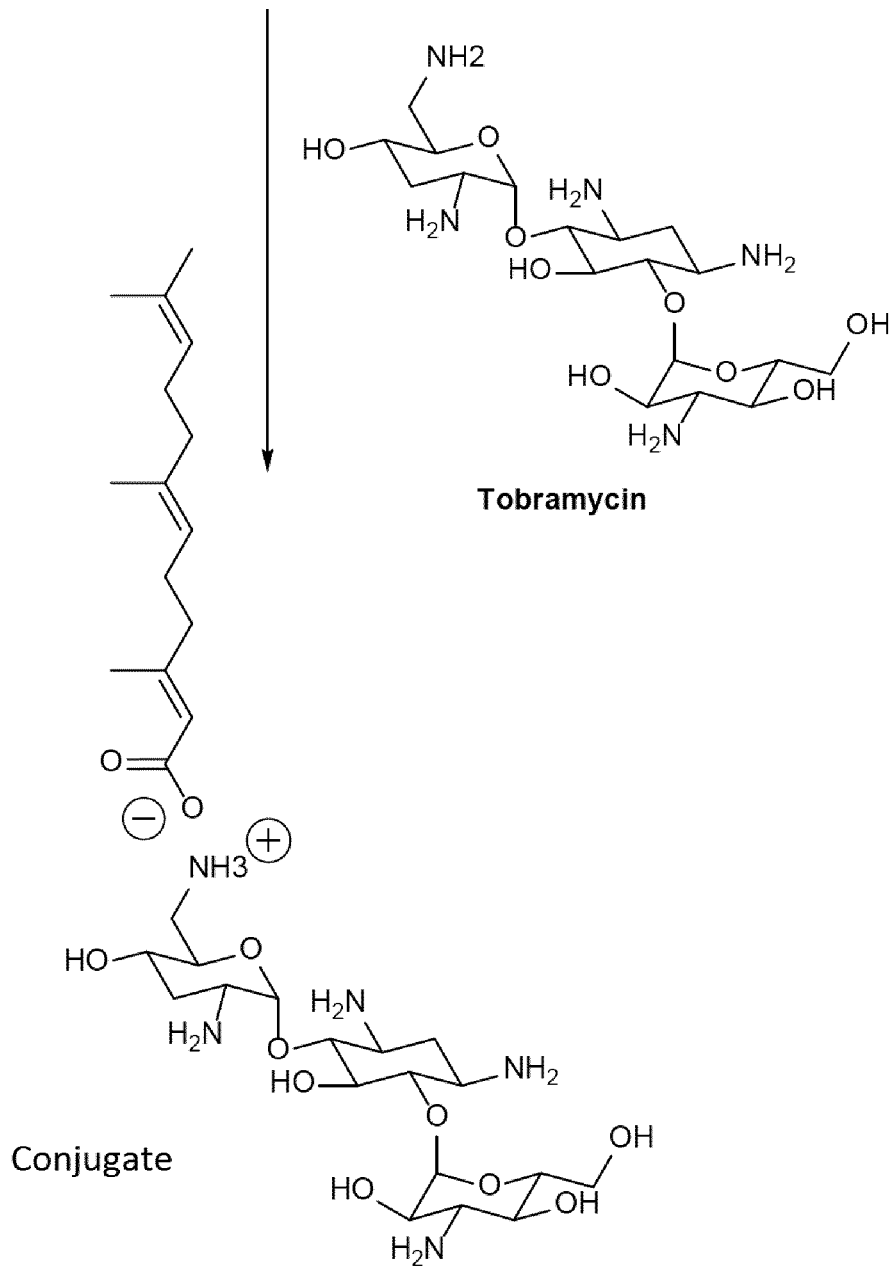
FIG. 3 schematically shows the preparation of a conjugate of the present invention comprising a tobramycin moiety and a farnesyl moiety. Notably, the preparation of the conjugate is essentially a single step preparation. The tobramycin moiety and the farnesyl moiety of the conjugate are linked via electrostatic interactions.
Figure 4:
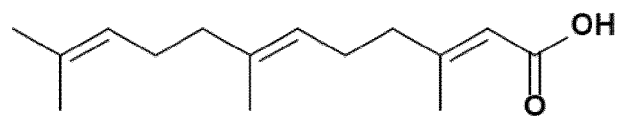
FIG. 4 shows farnesyl moieties comprising acid functional groups.
Figure 4:
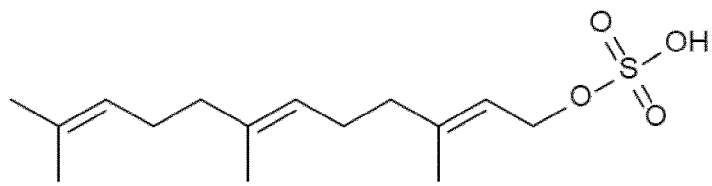
Figure 4:
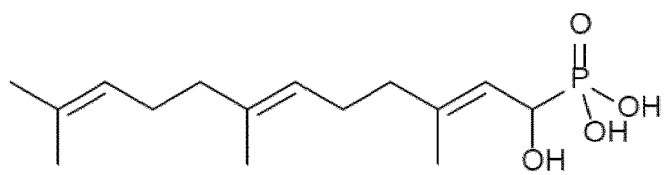
Figure 4:
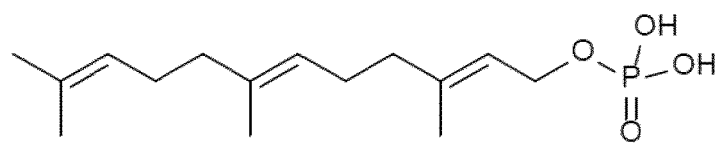
Figure 4:
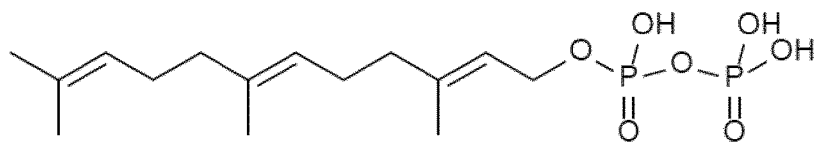
Figure 4:
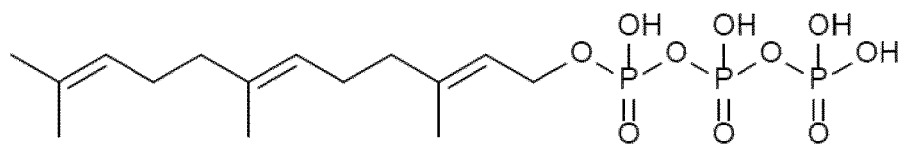

The preparation of the conjugate is schematically illustrated in FIGS. 1 (conjugate of tobramycin and farnesal) and 6 (conjugate of kanamycin A and farnesal). It can be seen that the aminoglycoside moiety and the farnesal moiety are linked via an imine group.

Preparation of an Aminoglycoside Solution and a Farnesal Solution

Aminoglycoside (kanamycin A or tobramycin) was dissolved in water. The pH of the aminoglycoside solution was adjusted to values of about 6.5 to 7.0. Then ethanol was slowly added into the solution until the volume ratio of water to ethanol reached about 1:0.8.

A farnesal solution was prepared in a separate flask using ethanol as a solvent.

Formation of the Conjugate

The farnesal solution was slowly added into the aminoglycoside solution until the molar ratio of aminoglycoside to farnesal was 1:1.1. The resulting solution was vigorously stirred for 3 hours. Then the pH was adjusted to values of about 7.0 to 7.8 and the solution was incubated for another 12 hours.

During the incubation a conjugate of the present invention was formed. The conjugate comprised an aminoglycoside moiety and a farnesyl moiety as shown in FIG. 1.

Isolation and Storage of the Conjugate

Subsequent to the formation of the conjugate described above the ethanol was removed by a vacuum rotary evaporator. Trace amounts of ethanol as well as non-conjugated aminoglycosides were removed by membrane dialysis in water. Subsequently, water was removed by freeze-drying and the sample was stored at −20° C. as closed and dried conditions.

Example 2: Preparation of the Nano-Assembly without Storage of the Conjugate

The conjugate of the present invention was formed as described in example 1 above. Subsequent to formation of the conjugate during incubation of the mixture of tobramycin and farnesal, ethanol was removed by a vacuum rotary evaporator as described in example 1 above. Trace amounts of ethanol as well as non-conjugated aminoglycosides were removed by membrane dialysis in purified water (MilliQ water). The present inventors found that the nano-assembly of the present invention formed spontaneously during removal of ethanol.

Example 3: Preparation of the Nano-Assembly Subsequent to Storage of the Conjugate The nano-assembly of the present invention can also be formed using the conjugate prepared and stored as described in example 1 as starting material. For this purpose, the respective conjugate was dissolved in a mixture of water and ethanol. The ratio (v/v) of water to ethanol was 1:1. Subsequently, ethanol was removed by a vacuum rotary evaporator as described in example 1 above. Trace amounts of ethanol as well as non-conjugated aminoglycosides were removed by membrane dialysis in purified water (MilliQ water). The present inventors found that the nano-assembly of the present invention formed spontaneously during removal of ethanol.

Example 4: Confirmation of Conjugation

Nano-assemblies of examples 2 and 3 were analyzed.

Successful formation of conjugates comprising an aminoglycoside moiety and a farnesyl moiety and formation of nano-assemblies thereof were confirmed by dynamic light scattering (DLS) measurements. A dramatic increase in zeta-potential was observed. Zeta-potential of pure farnesal was −33.8±0.5 mV, while the zeta potential of the nano-assemblies was found to be 29.6±0.5 mV. The increase in zeta-potential demonstrates successful conjugation of aminoglycoside and farnesal.

Example 5: Size of Nano-Assemblies

Figure 5:
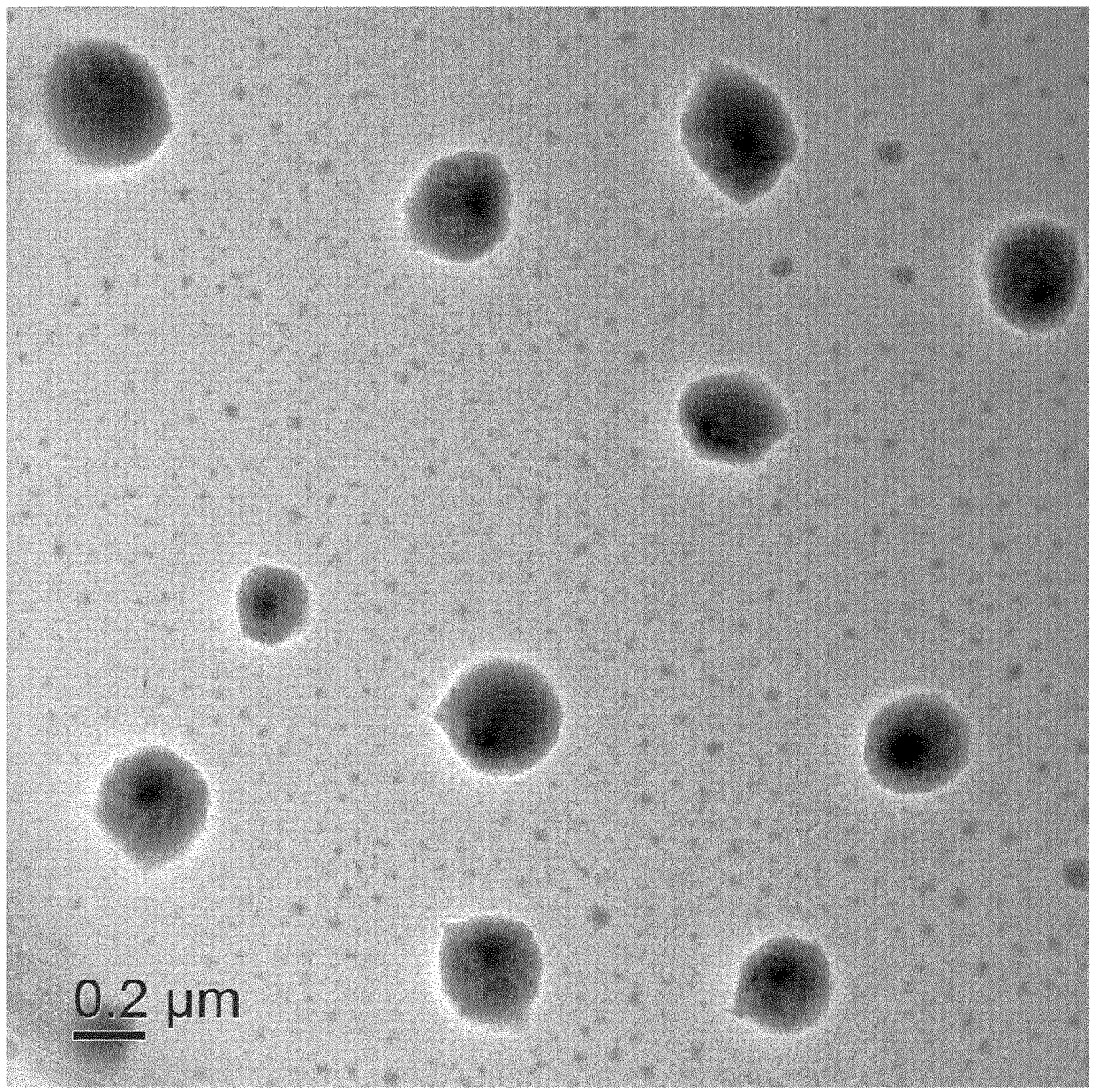
FIG. 5 shows representative TEM images of nano-assemblies comprising a kanamycin A moiety and a farnesyl moiety. The nano-assemblies were stained by phosphotungstic acid hydrate. The images were taken with a magnification of 6000×. The scale bar indicates 0.2 μm.
Figure 6:
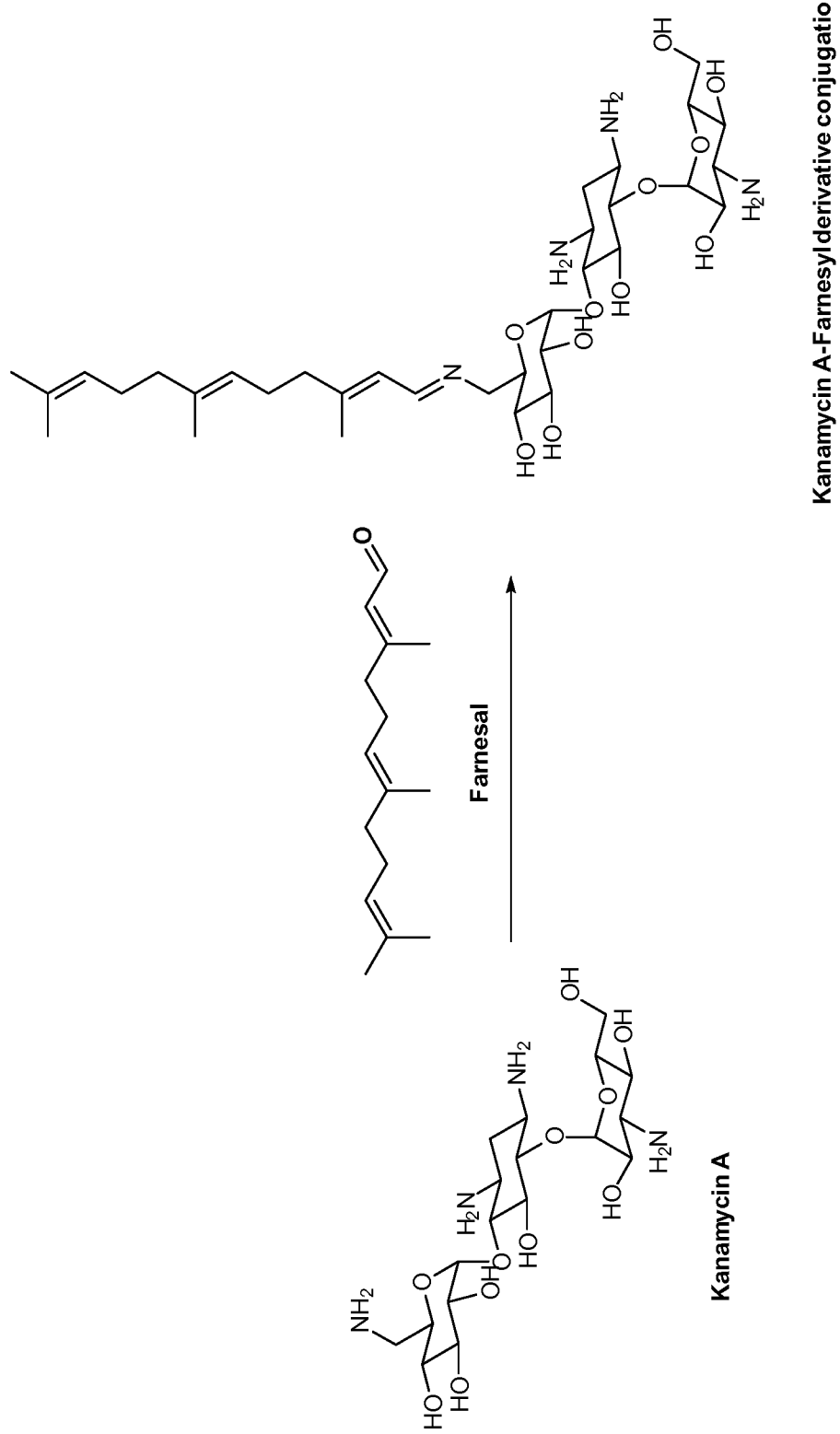
FIG. 6 schematically shows the preparation of a conjugate of the present invention comprising a kanamycin A moiety and a farnesyl moiety. Notably, the preparation of the conjugate is essentially a single step preparation.

Nano-assemblies of examples 2 and 3 were analyzed by transmission electron microscopy and were found to have a mean diameter of about 200 nm. FIG. 5 shows a representative TEM image. DLS experiments confirmed the mean diameter to be about 270 nm.

DLS experiments also confirmed homogeneous size distribution of the nano-assemblies. In fact, the polydispersity index (PDI) was determined to be 0.060±0.001, indicating a homogeneous distribution. PDI was calculated according to the following formula:

$$PDI = \left(\frac{\text{size standard deviation (nm)}}{\text{mean size (nm)}}\right)^2$$

Example 6: pH-Dependent Drug Release

In the obtained conjugates, the aminoglycoside moiety and the farnesyl moiety are connected via an imine bond. In order to check whether the imine bond might be cleaved in a pH-dependent manner, the tobramycin-containing nano-assemblies of examples 2 and 3 were incubated at different pH-values and the release of tobramycin was monitored at different time points by fluorescent activating method. Briefly, the product fluorescence of tobramycin was measured at 344/450 nm (Ex/Em) by Tecan microplate reader. The reagent consisted of 0.2 g of O-Phthalaldehyde dissolved in 1 mL methanol, 19 mL boric acid 0.4 M at pH 10.4 and 0.4 mL of 2-mercaptoethanol 14.3 M. 2 mL of the resulting mixture was then diluted with 16 mL methanol before use.

Figure 7:
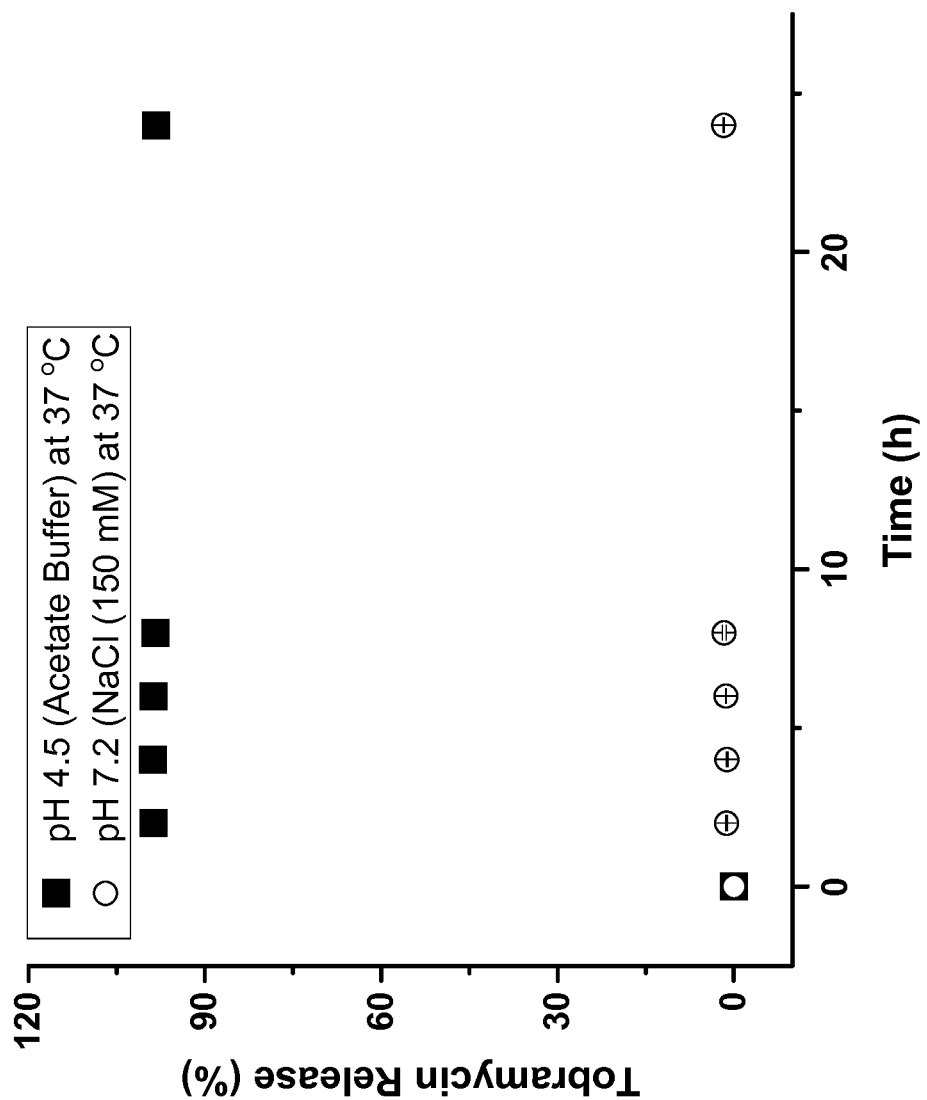
FIG. 7 shows stability of the nano-assembly of the present invention at different pH values. Release of tobramycin (y-axis) is plotted against the duration of incubation (x-axis).

The nano-assemblies were either incubated in saline (150 mM NaCl, pH 7.2) or in an acetate buffer consisting of sodium acetate and acetic acid (pH 4.5, 150 mM) at 37° C. and the release of tobramycin was checked after 2, 4, 6, 8 and 24 hours. The results of the experiment are shown in FIG. 7.

As can be seen clearly, tobramycin was almost completely released from the nano-assembly after 2 hours of incubation at pH 4.5. In contrast, the nano-assembly is stable in saline without release of drugs. In other words, there is no burst release because release is not based on a concentration gradient. Hence, the nano-assembly of the present invention does not only prevent burst release but also enhances locally sustained release at acidic pH environment. This is a huge advantage for controlled drug release.

Figure 8:
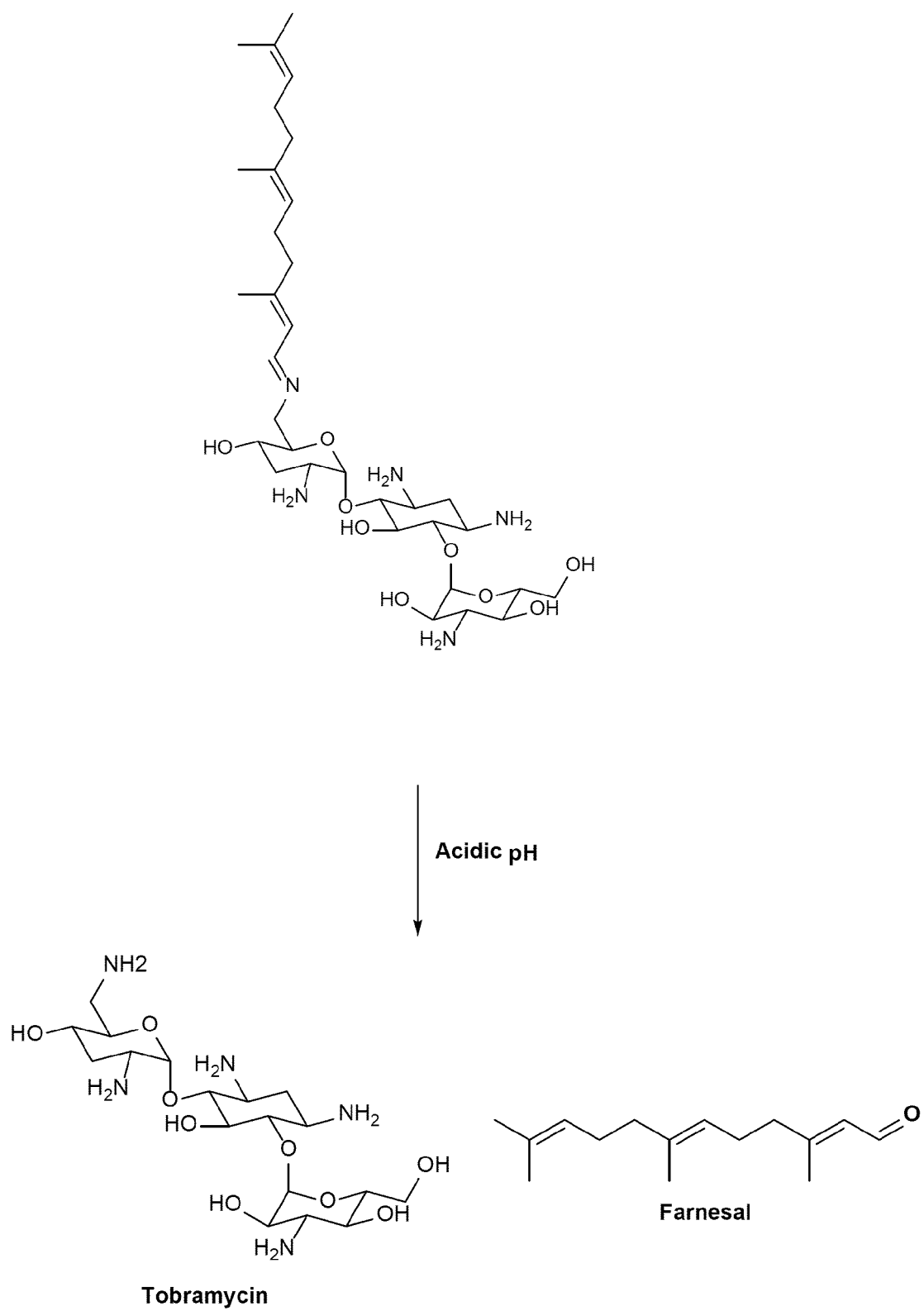
FIG. 8 schematically shows drug release from a conjugate of the present invention upon cleavage of the imine bond linking the aminoglycoside moiety and the farnesyl moiety.

In the present experiment, only release of the aminoglycoside moiety of the conjugate of the present invention was monitored. However, it should be noted that pH-dependent cleavage of the imine bond does not only release the aminoglycoside moiety but also the terpenoid moiety. The drug release upon cleavage of the imine bond is schematically shown in FIG. 8.

Example 7: Minimum Inhibitory Concentration (MIC)

The minimum inhibitory concentration (MIC) of the nano-assemblies of the tobramycin containing nano-assemblies against *E. coli* was tested and compared to known MIC values of tobramycin. The term "MIC-90" refers to the minimum inhibitory concentration required to inhibit the growth of 90% of the bacteria.

Dienstag and Neu (Antimicrobial Agents and Chemotherapy, 1972, vol. 1, p. 41-45) reported the MIC-90 of tobramycin against *E. coli* to be 6.25 µg/ml. The present inventors found the MIC-90 of the nano-assemblies of the present invention against *E. coli* to be substantially lower, namely about 0.125 µg/ml. In other words, the MIC-90 of the nano-assemblies of the present invention against *E. coli* is lower by a factor of 50 as compared to tobramycin alone.

Notably, the nano-assemblies of the present invention comprise a terpenoid moiety in addition to the aminoglycoside moiety. Thus, considering the molecular of weight of tobramycin (467.515 g/mol) and of farnesal (220.356 g/mol), the tobramycin content of 0.125 µg nano-assemblies is about 0.125*(467.515/(467.515+220.356))=0.083 µg. Hence, in relation to the content of tobramycin, the MIC-90 against *E. coli* is even at 0.083 µg/ml, which corresponds to a reduction of about 75-fold as compared to the known MIC-90 of tobramycin alone.

Example 8: Loading Additional Substances into the Nano-Assemblies

Nano-assemblies of the present invention loaded with different additional substances were produced.

Farnesol-Loaded Nano-Assemblies 3 mg of a tobramycin-farnesyl conjugate of example 1 as well as 1 mg of farnesol were dissolved in a mixture of water and ethanol, wherein the ratio (v/v) of water to ethanol was 1:1. Subsequently, ethanol was evaporated. The nano-assembly formed spontaneously upon evaporation of ethanol. Farnesol was co-precipitated into the forming nano-assembly. Subsequently, trace amounts of ethanol were removed by membrane dialysis in purified water (MilliQ water). Loading of farnesol into the nano-assembly is schematically shown in the following scheme:

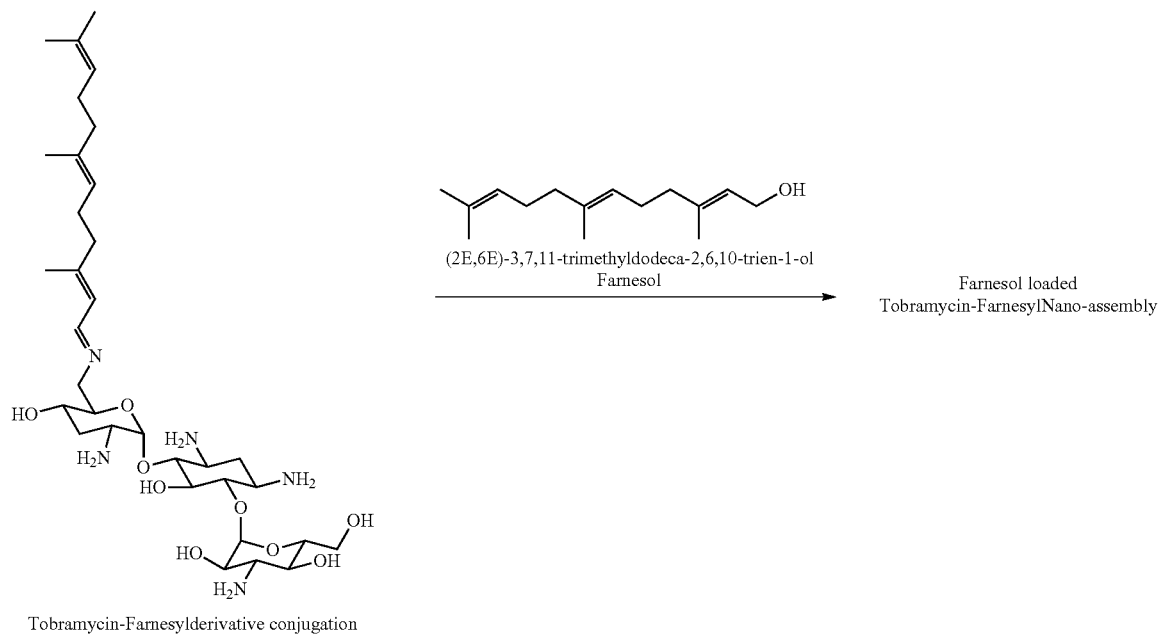 [SMILES: CC(C)=CCC/C(C)=C/CC/C(C)=C/C=N/CC1OC(OC2C(N)CC(N)C(OC3OC(CO)C(O)C(N)C3O)C2O)C(N)CC1O ; CC(C)=CCC/C(C)=C/CC/C(C)=C/CO]

Tobramycin-Farnesylderivative conjugation

The farnesol loaded nano-assemblies had a mean diameter of 576.5±19.3 nm, a PDI of 0.116±0.064 and a zeta-potential of 33.2±1.68 mV. Thus, the mean diameter of the loaded nano-assemblies is substantially increased in comparison to unloaded nano-assemblies (see example 5).

The loading of farnesol was quantified by liquid chromatography-mass spectrometry (LC-MS). Encapsulation efficiency was determined to be 93.5%, and loading rate was determined to be 23.76%. Thus, loading of farnesol into the nano-assembly was very efficient.

The encapsulation efficiency was calculated according to the following formula:

$$\text{Encapsulation Efficiency} = \frac{\text{Actual weight of Farnesol loaded in the nanoassembly}}{\text{Initial weight of Farnesol used to load}} \times 100\%$$

The loading rate was calculated according to the following formula:

$$\text{Loading rate} = \frac{\text{Actual weight of Farnesol loaded in the nanoassembly}}{\text{Actual weight of Farnesol loaded in the nanoassembly} + \text{Weight of conjugate}} \times 100\%$$

Farnesal-Loaded Nano-Assemblies

Farnesal may be loaded into the nano-assemblies as described for farnesol-loading above. However, more preferably, farnesal may be used in excess during conjugate formation in order to obtain farnesal-loaded nano-assemblies as described in the following.

A conjugate comprising an aminoglycoside moiety and a farnesyl moiety can be formed using a farnesal solution and an aminoglycoside solution as described in example 1. Furthermore, nano-assemblies of such conjugates can be formed as described in examples 2 and 3.

Example 1 describes that for formation of the conjugates the farnesal solution was slowly added into the aminoglycoside solution until the molar ratio of aminoglycoside to farnesal was 1:1.1. Higher amounts of farnesal can be used for preparing nano-assemblies of conjugates of the invention loaded with additional farnesal.

For example, the molar ratio of aminoglycoside to farnesal may be 1:x (with x>1). When x is smaller or equal to the total number of amine functional groups in the aminoglycoside (e.g Tobramycin with 5 primary amine groups, or Kanamycin A with 4 primary amine groups, or Plazomicin with 3 primary amine groups, and 2 secondary amine groups), there will be covalent linkages formed between aminoglycoside and farnesal via the chemical reaction between aldehyde and amine groups.

However, when x exceeds the total number of amine functional groups in the aminoglycoside, the un-reacted farnesal is loaded into the nano-assembly upon nano-assembly formation. Such farnesal-loaded nano-assemblies are formed when the excess amount of farnesal is not removed from the resulting conjugate prior to nano-assembly formation. Such farnesal-loaded nano-assemblies are particularly useful when the amount of quorum sensing inhibitor in the nano-assembly is needed to be increased for further application (e.g biofilm eradication).

Farnesal-loaded nano-assemblies were prepared by using farnesal in excess over the total number of amine functional groups in the aminoglycoside during conjugate formation and subsequently forming the nano-assembly as described in example 2 without removing the excess amount of farnesal from the resulting conjugate prior to nano-assembly formation.

Nano-Assemblies Loaded with Farnesyl Hydrogen Sulfate

Preparing Farnesyl Hydrogen Sulfate Nano-Assemblies

A newly synthesized quorum sensing inhibitor, Farnesyl hydrogen sulfate is a product of a reaction between Farnesol and sulfur trioxide triethylamine complex in dimethylformamide (DMF).

Figure 14:
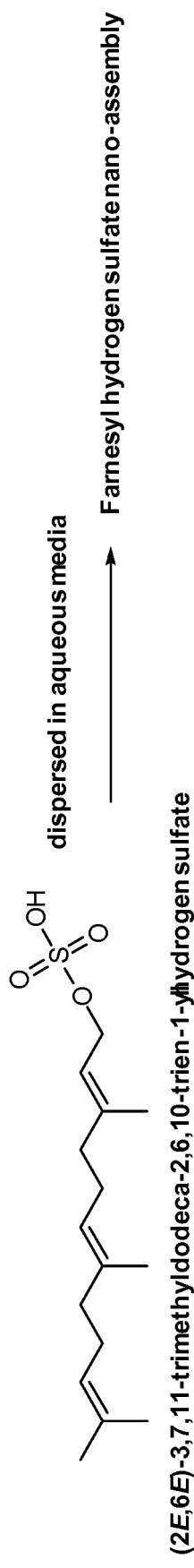
FIG. 14 shows schematically the formation of Farnesyl hydrogen sulfate nano-assemblies in aqueous media.

Farnesyl hydrogen sulfate forms nano-assemblies when being dispersed in aqueous media due to the strong hydrophilicity of hydrogen sulfate functional group. Formation of Farnesyl hydrogen sulfate nano-assemblies is schematically shown in FIG. 14.

The formation of Farnesyl hydrogen sulfate nano-assemblies in aqueous media was done as follows: Farnesyl hydrogen sulfate was solubilized in ethanol. 0.2 mL of the solution of Farnesyl hydrogen sulfate in ethanol (10 mg/mL) were then dropped into 1 mL MilliQ water, and the nano-assembly of Farnesyl hydrogen sulfate was formed spontaneously. Ethanol was then evaporated, and the trace amount of ethanol was further removed by membrane dialysis in MilliQ water.

The nano-assemblies had a mean diameter of 145.8±1.4 nm, a PDI 0.053±0.014, and a zeta-potential of −33.7±0.9 mV after completely removing ethanol. The morphology was confirmed by Cryo Transmission Electron Microscopy (not shown). These Farnesyl hydrogen sulfate nano-assemblies were used in the Pyocyanin assay (example 10).

Loading Farnesyl Hydrogen Sulfate into Nano-Assemblies of the Invention

Farnesyl hydrogen sulfate and the Tobramycin-Farnesyl conjugate of Example 1 were dissolved in a mixture of water:ethanol ratio of 1:1 (v:v). The nano-assembly was formed spontaneously when ethanol was evaporated. Farnesyl hydrogen sulfate is in the core side together with Farnesyl moieties when ethanol is removed. Thus, Farnesyl hydrogen sulfate loaded nano-assemblies are obtained. Trace amount of ethanol were removed by membrane dialysis in MilliQ water. The formation of the Farnesyl hydrogen sulfate loaded nano-assemblies is schematically shown below.

The Farnesyl hydrogen sulfate loaded Tobramycin-Farnesyl nano-assemblies had a mean diameter of 378.5±8.3 nm, PDI of 0.103±0.024, and a zeta-potential of 27.2±2.98 mV. Thus, the mean diameter of the loaded nano-assemblies is increased in comparison to unloaded nano-assemblies (see example 5). However, the mean diameter of the Farnesyl hydrogen sulfate loaded nano-assemblies is substantially smaller as compared to the mean diameter of the Farnesol-loaded nano-assemblies.

Due to the self-assembling properties of Farnesyl hydrogen sulfate and the similar hydrophobicity of Farnesyl moieties, the encapsulation efficiency was maximized to 100%, and the loading rate was controlled as the feeding ratio of the two compounds.

Nano-Assemblies Loaded with Quinolone Derivative (Another Quorum Sensing Inhibitor)

3 mg of a tobramycin-farnesyl conjugate of example 1 as well as 50 µg of 2-heptyl-6-nitro-4-oxo-1,4-dihydroquinoline-3-carboxamide were dissolved in a mixture of water and ethanol, wherein the ratio (v/v) of water to ethanol was 1:1. Subsequently, ethanol was evaporated. The nano-assembly formed spontaneously upon evaporation of ethanol. 2-heptyl-6-nitro-4-oxo-1,4-dihydroquinoline-3-carboxamide was co-precipitated into the forming nano-assembly. Subsequently, trace amounts of ethanol were removed by membrane dialysis in water. Loading of 2-heptyl-6-nitro-4-oxo-1,4-dihydroquinoline-3-carboxamide into the nano-assembly is schematically shown in the following scheme:

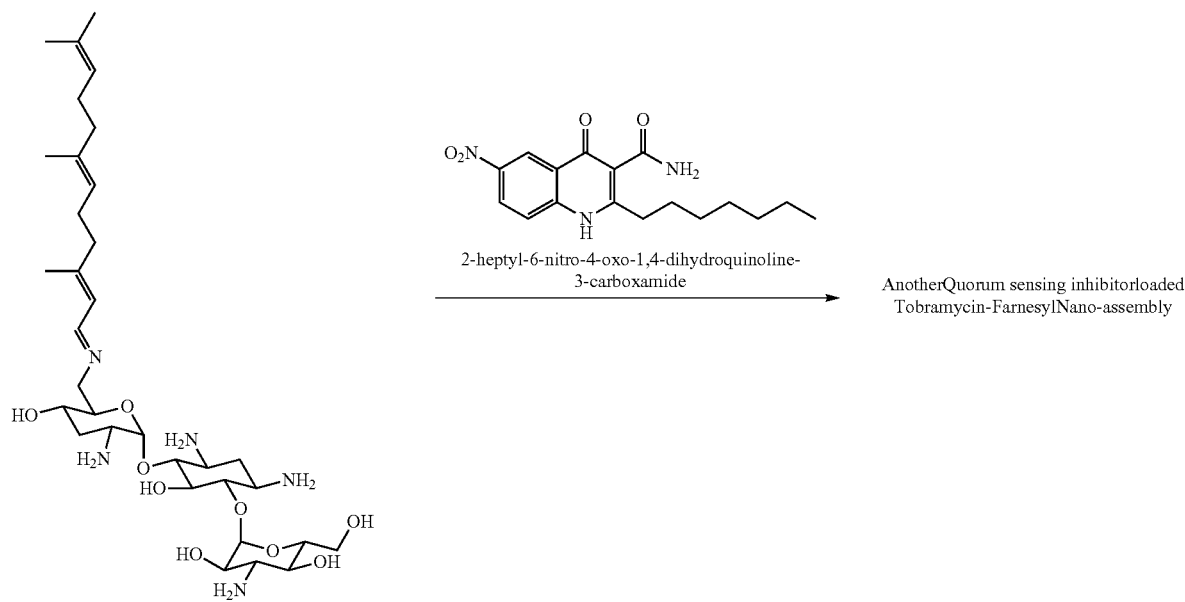

The 2-heptyl-6-nitro-4-oxo-1,4-dihydroquinoline-3-carboxamide loaded nano-assemblies had a mean diameter of 294±3.9 nm, a PDI of 0.137±0.041 and a zeta-potential of 34.8±0.404 mV. Thus, the mean diameter of the loaded nano-assemblies is smaller as compared to the farnesol-loaded nano-assemblies.

The loading of 2-heptyl-6-nitro-4-oxo-1,4-dihydroquinoline-3-carboxamide was quantified by liquid chromatography-mass spectrometry (LC-MS). Encapsulation efficiency was determined to be 94%, and loading rate was determined to be 1.54%. Thus, loading of 2-heptyl-6-nitro-4-oxo-1,4-dihydroquinoline-3-carboxamide into the nano-assembly was very efficient.

Encapsulation efficiency and loading rate were calculated based on the formulas indicated above for loading of farnesol.

Nano-Assemblies Loaded with Nile Red 3 mg of a tobramycin-farnesyl conjugate of example 1 as well as 6 µg of Nile red were dissolved in a mixture of water and ethanol, wherein the ratio (v/v) of water to ethanol was 1:1. Subsequently, ethanol was evaporated. The nano-assembly formed spontaneously upon evaporation of ethanol. Nile red was co-precipitated into the forming nano-assembly. Subsequently, trace amounts of ethanol were removed by membrane dialysis in water. Loading of Nile red into the nano-assembly is schematically shown in the following scheme:

Encapsulation efficiency and loading rate were calculated based on the formulas indicated above for loading of farnesol.

Example 9: MIC Assay Against *Pseudomonas aeruginosa*

The minimum inhibitory concentration (MIC) of the of the tobramycin containing nano-assemblies of example 2 against the *P. aeruginosa* strain PA14 (wild type) was tested and compared to known MIC values of tobramycin. The term "MIC-90" refers to the minimum inhibitory concentration required to inhibit the growth of 90% of the bacteria.

The MIC-90 of Tobramycin against PA14 was found to be in the range 6.25-12.5 µg/mL, while the MIC values of the nano-assemblies of the present invention comprising Farnesyl moieties and Tobramycin with the molar ratio Farnesyl moieties:Tobramycin 1:1, and 4:1 were found to be 3.125 µg/mL, and 1.562 µg/mL, respectively.

Thus, the amount of Tobramycin in the nano-assemblies with the molar ratio Farnesyl moieties:Tobramycin 1:1, and 4:1 was 2.075 µg/mL (calculated following the equation (see also example 7 above): 3.125*(467.515/(467.515+220.356))= 2.075 µg/mL), and 0.541 µg/mL (calculated following the equation: 1.562*(467.515/(467.515+4*220.356))=0.541 µg/mL, which show the improvement by 3-6 fold, and 11.5-23 fold compared to the free Tobramycin.

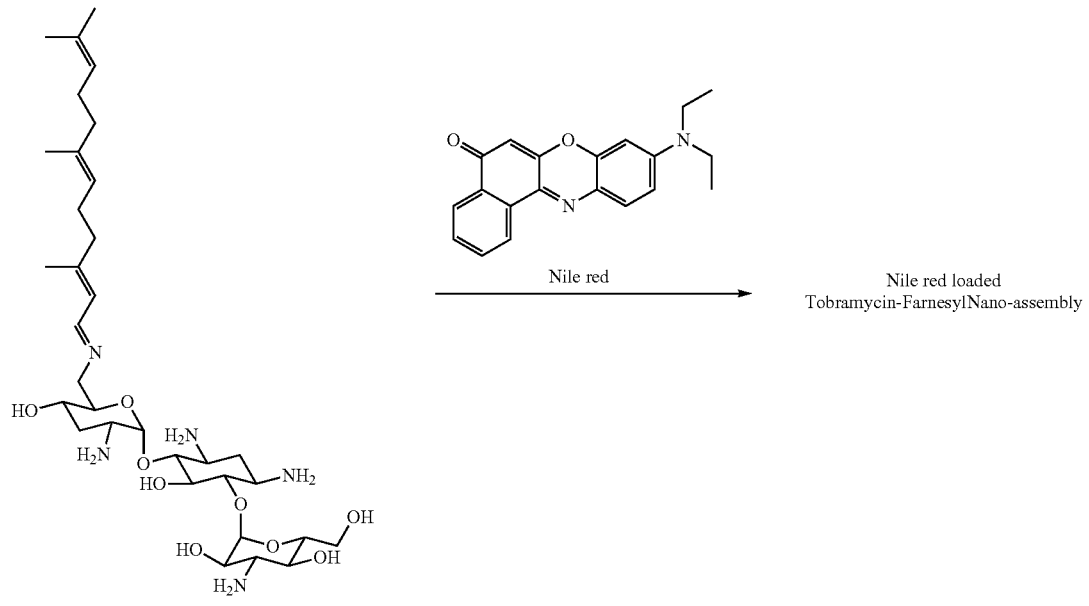

Tobramycin-Farnesylderivative conjugation

The Nile red loaded nano-assemblies had a mean diameter of 270 nm, a PDI of 0.080±0.001 and a zeta-potential of 25.9±0.603 mV. Thus, the mean diameter of the loaded nano-assemblies is smaller as compared to the farnesol-loaded nano-assemblies.

The loading of Nile red was quantified by fluorescence intensity of the Nile red dye. Encapsulation efficiency was determined to be 97%, and loading rate was determined to be 0.16%. Thus, loading of Nile red into the nano-assembly was very efficient.

Example 10: Pyocyanin Assay on *Pseudomonas aeruginosa*

Pyocyanin assay was used to quantify the amount of Pyocyanin molecule released from PA14 bacteria (wild type) which were grown aerobically for 16 hours. The Pyocyanin assay was performed as follows:

A single colony of PA14 was removed from agar plates after 16 hours of growth at 37° C. and transferred into 25 mL Erlenmeyer flasks with 10 mL of PPGAS (proteose peptone glucose ammonium salt medium which is composed of (1 g/L NH$_4$Cl, 1.5 g/L KCl, 19 g/L Tris-HCl, 10 g/L peptone, glucose 5 g/L and 0.1 g/L MgSO$_4$·7H$_2$O, the medium was adjusted to pH 7.4, and sterilized before use). Following 16 hours of aerobic growth with shaking at 200 rpm and 37° C., cultures were centrifuged at 7.450 g, washed twice with 10 mL of fresh PPGAS medium, and resuspended to a final volume of 5 mL solution. Cultures were then diluted to a final OD600 of 0.02 and distributed into 24 well-plates, 1.5 mL each well.

Compounds Farnesal and Farnesol were diluted in DMSO, then added to wells containing PA14 bacteria, in 1:100 dilutions with a final DMSO concentration of 1% (v/v), so that the final concentration of Farnesal was 18 μg/mL, and of Farnesol was 18 μg/mL.

The nano-assemblies containing Farnesal dispersed in MilliQ water (see example 8), or nano-assemblies containing Farnesol dispersed in MilliQ water (see example 8) were added to wells containing PA14 bacteria, in 1:100 dilutions with a final MilliQ water concentration of 1% (v/v). The final concentration of total Farnesal (=loaded Farnesal+Farnesyl moieties of the conjugates forming the nano-assemblies) was 18 μg/mL for the Farnesal-loaded nano-assemblies. The final concentration of total Farnesol (=loaded Farnesol) was 18 μg/mL for the Farnesol-loaded nano-assemblies. Notably, tobramycin is generated upon cleavage of the tobramycin-farnesyl conjugates forming the nano-assemblies both in the case of Farnesal-loaded nano-assemblies and in the case of Farnesol-loaded nano-assemblies. However, the amount of tobramycin was so low that it was excluded that the observed effects were based on tobramycin. Rather, the effects were caused by Farnesal and Farnesol, respectively. Notably, Farnesal is generated upon cleavage of the tobramycin-farnesyl conjugates forming the nano-assemblies in case of the Farnesol-loaded nano-assemblies as well. However, the amount of Farnesal was so low as compared to the amount of Farnesol that it was excluded that the observed effects were based on Farnesal. Rather, the effects of the Farnesol-loaded nano-assemblies were based on Farnesol.

The nano-assemblies of Farnesyl hydrogen sulfate dispersed in MilliQ water (see example 8) were added to wells containing PA14 bacteria, in 1:100 dilutions with a final MilliQ water concentration of 1% (v/v), and the final concentration of total Farnesyl hydrogen sulfate was 10 μg/mL. The Farnesyl hydrogen sulfate nano-assemblies did not contain any moieties potentially generating aminoglycosides or Farnesal. Thus, the observed effects were based on Farnesyl hydrogen sulfate.

Untreated cultures of PA14 were also incubated to serve as controls.

All cultures were incubated for an additional 16 h under aerobic conditions as mentioned above. Pyocyanin was extracted by adding 900 μL of chloroform to 900 μL of 16 h culture and subsequently re-extracted with 250 μL of 0.2 M HCl from the organic phase. OD520 was measured in the aqueous phase. Pyocyanin formation values were normalized to a corresponding OD600 of the respective sample.

OD600 and OD520 are absorbance values of the solution at the wave-length 600 nm and 520 nm, respectively.

The results are presented as percentage (%) inhibition of released Pyocyanin molecules in comparison to PA14 wt control. The results are shown in FIG. 9.

Pyocyanin molecules are important agents for the communication of bacteria and the formation of biofilms. Pyocyanin molecules play an essential role in resistance of bacteria. As a result, quorum sensing inhibitory molecules are developed to inhibit the production of Pyocyanin molecules, which would help preventing the fast resistance of bacteria, and at the same time improving infection treatment.

Some Farnesyl derivatives are natural quorum sensing inhibitors which would be preferable in pharmaceutical application. They, however, are highly hydrophobic compounds; hence, its water-insolubility seriously limits their applying potential, as well as the pharmacological efficacy.

Figure 9:
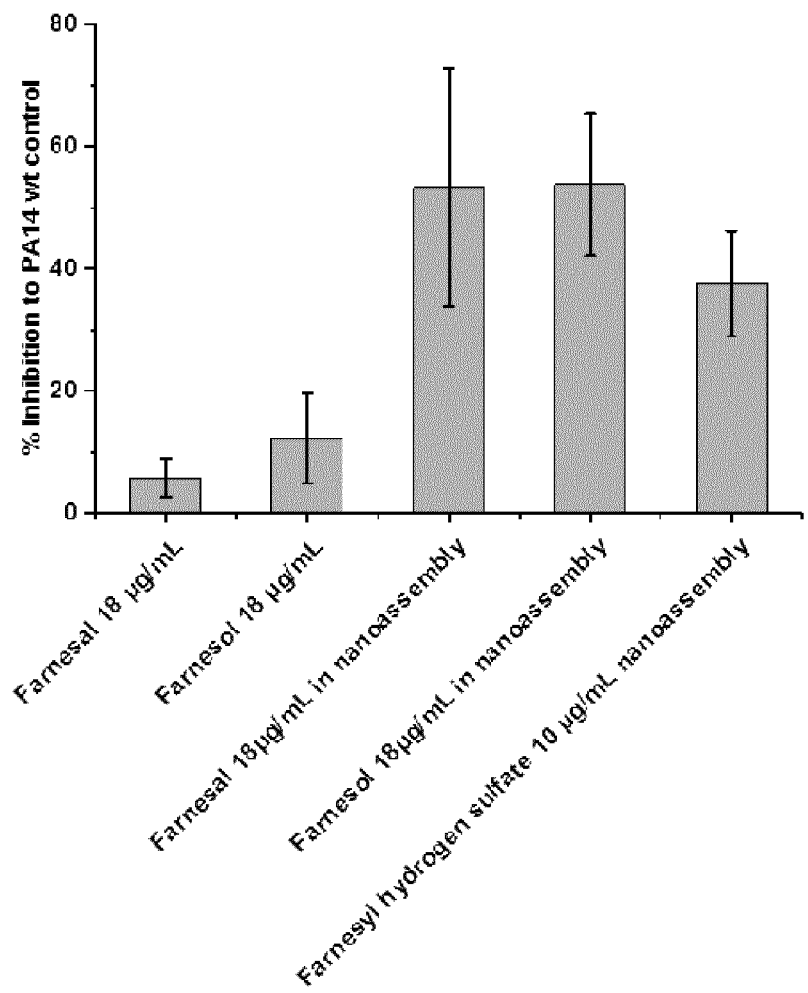
FIG. 9 shows percentages of inhibition of released Pyocyanin molecules in comparison to PA14 wild type control when applying Farnesal 18 μg/mL diluted in DMSO, Farnesol 18 μg/mL diluted in DMSO, Farnesal 18 μg/mL in the nano-assembly dispersed in MilliQ water, Farnesol 18 μg/mL loaded in the nano-assembly dispersed in MilliQ water, and Farnesyl hydrogen sulfate 10 μg/mL nano-assembly dispersed in MilliQ water. All values represent the average of three independent experiments with practical triplicate (n=9). The error bars indicate the standard deviation.

As can be seen in FIG. 9, the free Farnesyl derivatives (Farnesal, and Farnesol) had to be diluted in DMSO before applying into bacteria culture. Although the inhibition of Pyocyanin production by those two compounds was shown, the efficacy was not significant with the percentage of inhibition lower than 20% at 18 μg/mL concentration in both cases. (Detailed results: Farnesal: 5.85±3.10% inhibition, Farnesol: 12.29±7.35%)

Notably, the nano-assemblies loaded with Farnesal or Farnesol dispersed in MilliQ water showed significant improvement in Pyocyanin inhibition in comparison to corresponding free compound at the same concentration. The inhibitory efficacy of Farnesal loaded nano-assembly was 53.35±19.53%, and of Farnesol loaded nano-assembly was 53.80±11.68%.

Notably, Farnesyl hydrogen sulfate forms the nano-assembly by itself in MilliQ water, and shows remarkable inhibition in Pyocyanin production even at lower concentration of 10 μg/mL. The percentage inhibition was 37.62±8.54%.

In summary, the results of the Pyocyanin assay show that the conjugates of the present invention have remarkable quorum sensing inhibitory properties and are superior to free Farnesal and Farnsesol.

Example 11: MBEC Assay Against *Pseudomonas aeruginosa*

Minimum Biofilm Eradicating Concentration (MBEC) assay was used to determine the minimum concentration of active agents at which a 24 hours old PA14 biofilm is completely eradicated. The MBEC assay was performed as follows:

A single colony of PA14 was removed from agar plates after 16 hours of growth at 37° C. and transferred into 25 mL Erlenmeyer flasks with 10 mL of PPGAS (proteose peptone glucose ammonium salt medium which is composed of (1 g/L NH$_4$Cl, 1.5 g/L KCl, 19 g/L Tris-HCl, 10 g/L peptone, glucose 5 g/L and 0.1 g/L MgSO$_4$·7H$_2$O, the medium was adjusted to pH 7.4, and sterilized before use). Following 16 hours of aerobic growth with shaking at 200 rpm and 37° C., cultures were centrifuged at 7.450 g, washed twice with 10 mL of fresh PPGAS medium, and resuspended to a final volume of 5 mL solution. Cultures were then diluted to a final OD600 of 3.0 and distributed into 96 well-plates, 0.2 mL each well.

The 96 well-plates were then kept at 37° C. without shaking for 24 hours to allow the forming of biofilm. Afterwards, the planktonic bacteria were removed, and the 24 hours old biofilm was washed twice with PBS, then fed with fresh PPGAS medium, and ready for the assay.

For the assay, free Tobramycin was solubilized in MilliQ water at different concentrations, then added to wells containing PA14 bacteria biofilm, in 1:20 dilutions, so that the final concentration of Tobramycin was ranged from 6.25 to 100 μg/mL.

The nano-assemblies of conjugates of Tobramycin and Farnesal dispersed in MilliQ water were prepared with various feeding concentrations of Tobramycin, then added to wells containing PA14 bacteria biofilm, in 1:20 dilutions, so that the final concentration of Tobramycin was ranged from 6.25 to 100 μg/mL, while concentration of Farnesal was kept constant.

Similarly, the Farnesol-loaded nano-assemblies of example 8 dispersed in MilliQ water were prepared with various feeding concentrations of Tobramycin, then added to wells containing PA14 bacteria biofilm, in 1:20 dilutions, so that the final concentration of Tobramycin was ranged from 6.25 to 100 μg/mL, while concentrations of Farnesal and Farnesol were kept constant.

Similarly, the nano-assemblies composed of Tobramycin, Farnesal and Farnesyl hydrogen sulfate dispersed in MilliQ water (see example 8) were prepared with various feeding concentrations of Tobramycin, then added to wells containing PA14 bacteria biofilm, in 1:20 dilutions, so that the final concentration of Tobramycin was ranged from 6.25 to 100 μg/mL, while concentrations of Farnesal and Farnesyl hydrogen sulfate were kept constant.

Untreated biofilm of PA14 were also incubated to serve as controls.

All cultures were incubated for an additional 24 hours at 37° C. without shaking. Then, all samples were washed twice with PBS, added 200 mL fresh PPGAS and sonicated to disperse the biofilm. From each well of the challenged plates, 100 mL of dispersed biofilm was transferred to new 96 well-plates which are further incubated for 24 hours at 37° C. without shaking. All cultures were then measured OD650, and the biofilm is considered to be completely eradicated once the resulting OD650 is equal or lower than OD650 of PPGAS medium.

OD600 and OD650 are absorbance values of the solution at the wave-length 600 nm and 650 nm, respectively.

The results are shown in FIGS. 10 to 13.

Figure 10:
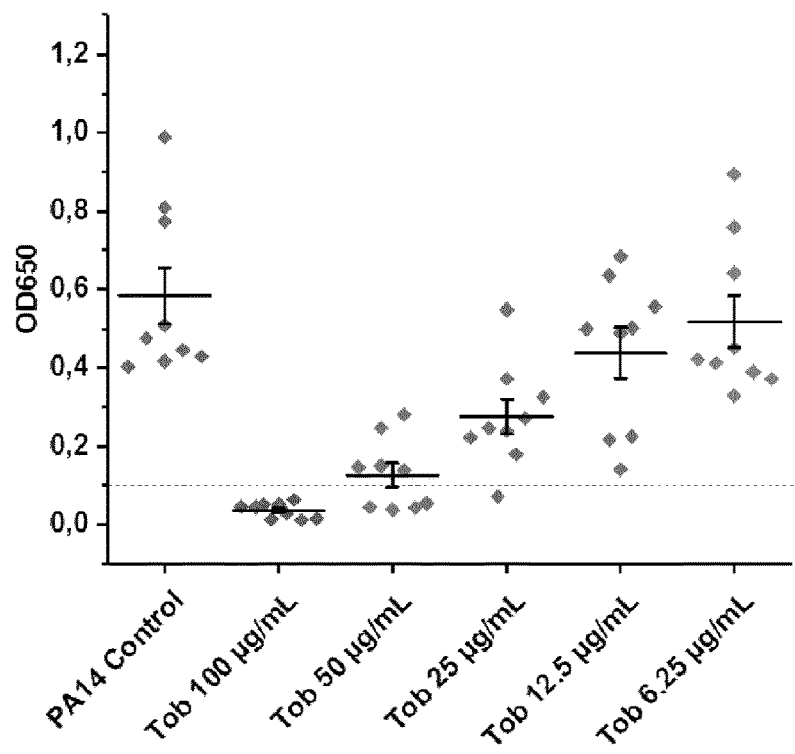
FIG. 10 shows MBEC assay results of 24 hours old PA14 wild type biofilm treated with free Tobramycin for 24 hours. Each dot represents the results of one experiment. 9 independent experiments have been performed for each condition. The mean results are indicated as a horizontal bar. The error bars show the standard deviation. The dotted horizontal line shows the OD650 of PPGAS medium that serves as the standard for determining complete eradication.

As shown in Example 9, free Tobramycin concentration at 6.25 to 12.5 μg/mL was the minimum concentration against planktonic PA14. However, once bacteria are protected in biofilm, the concentration of Tobramycin needed to completely eradicate bacterial infection was 100 μg/mL or higher, as shown in FIG. 10. The fact of higher Tobramycin dose needed to eliminate biofilm is known and was verified here. The need for higher dose is a challenge in biofilm-associated infections and shortcomings in the delivery of the needed amount can promote bacterial antibiotic resistance development.

Figure 11:
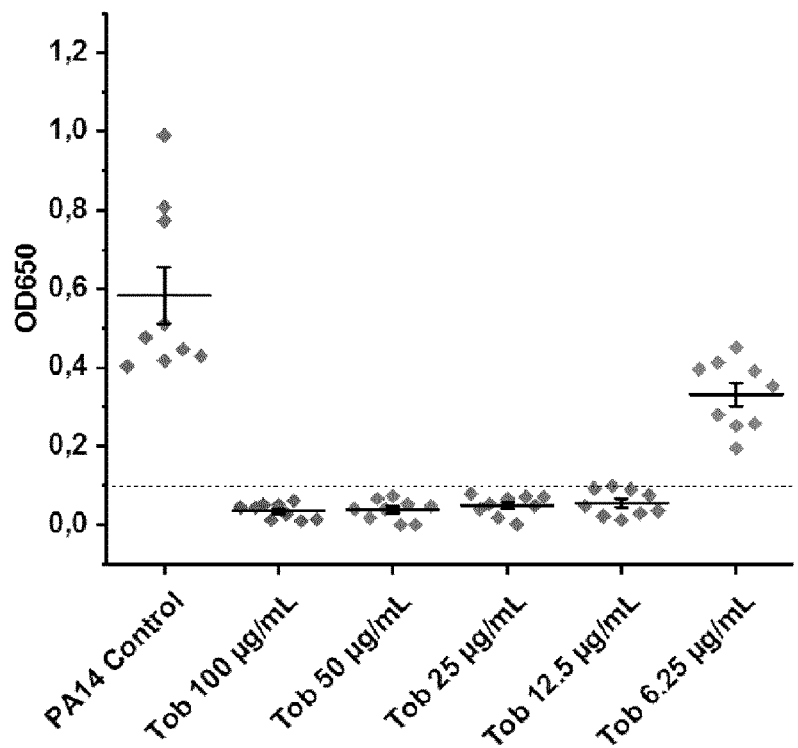
FIG. 11 shows MBEC assay results of 24 hours old PA14 wild type biofilm treated with nano-assemblies of conjugates of Tobramycin and Farnesal for 24 hours. Each dot represents the results of one experiment. 9 independent experiments have been performed for each condition. The mean results are indicated as a horizontal bar. The error bars show the standard deviation. The dotted horizontal line shows the OD650 of PPGAS medium that serves as the standard for determining complete eradication.
Figure 12:
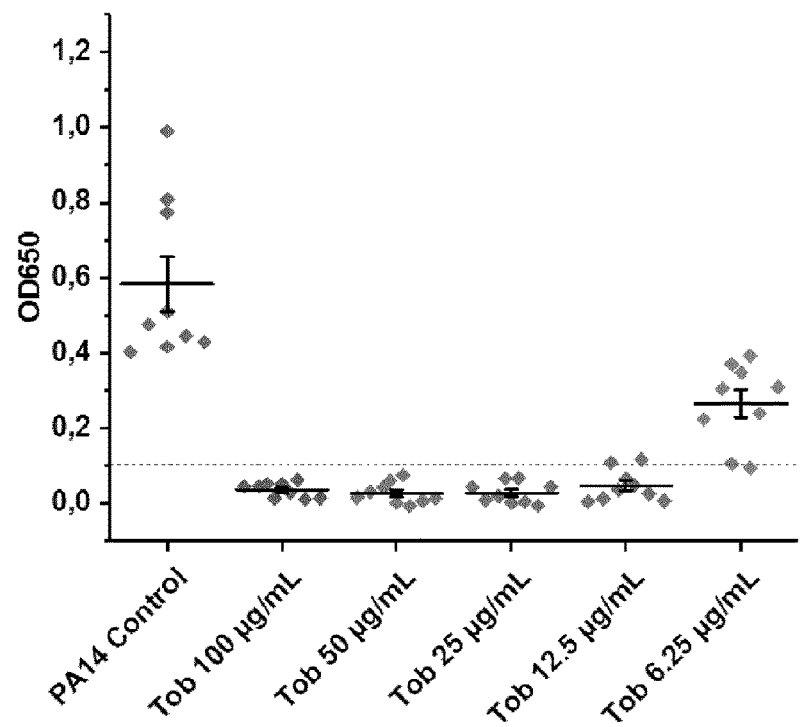
FIG. 12 shows MBEC assay results of 24 hours old PA14 wild type biofilm treated for 24 hours with nano-assemblies of conjugates of Tobramycin and Farnesal further loaded with Farnesol. Each dot represents the results of one experiment. 9 independent experiments have been performed for each condition. The mean results are indicated as a horizontal bar. The error bars show the standard deviation. The dotted horizontal line shows the OD650 of PPGAS medium that serves as the standard for determining complete eradication.
Figure 13:
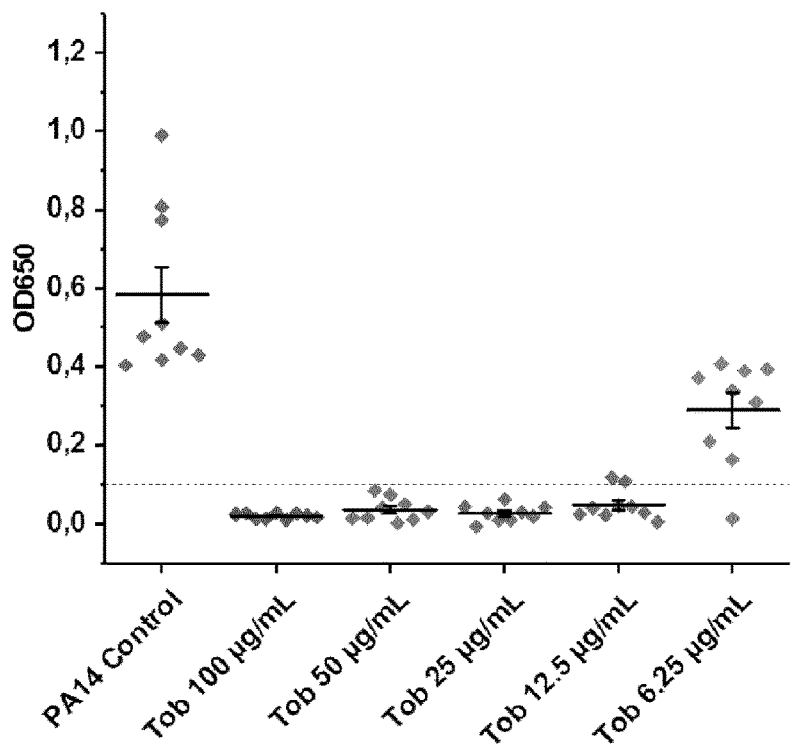
FIG. 13 shows MBEC assay results of 24 hours old PA14 wild type biofilm treated for 24 hours with nano-assemblies of conjugates of Tobramycin and Farnesal further loaded with Farnesyl Hydrogen Sulfate. Each dot represents the results of one experiment. 9 independent experiments have been performed for each condition. The mean results are indicated as a horizontal bar. The error bars show the standard deviation. The dotted horizontal line shows the OD650 of PPGAS medium that serves as the standard for determining complete eradication.

The present invention comprises the complementary treatment strategy of combining Tobramycin and Farnesyl quorum sensing inhibitors. Moreover, the conjugates of the two active compounds were also able to self-assembly into nano-assemblies. The nano-assemblies remarkably improve the efficacy against PA14 biofilm in comparison to the use of just free Tobramycin. As shown in FIGS. 11, 12 and 13, the Tobramycin needed for the complete biofilm eradication was at 12.5 μg/mL which is 8-fold lower than that of free Tobramycin.

In summary, the results of the MBEC assay show that the conjugates of the present invention have remarkable biofilm eradicating properties and are superior to free Tobramycin.

The invention claimed is:

1. A conjugate comprising an aminoglycoside moiety and at least one terpenyl moiety, wherein the terpenyl moiety has at most 20 carbon atoms, and wherein the aminoglycoside moiety and the terpenyl moiety are linked via a pH-sensitive link that is not stable at a pH<5.0, wherein the term "not stable" indicates that at least 80% of the aminoglycoside is released from the conjugate after incubation at pH<5.0 for at most 8 hours at a temperature of 37° C.

2. The conjugate according to claim 1, wherein the aminoglycoside moiety and the terpenyl moiety are covalently linked.

3. The conjugate according to claim 1, wherein the aminoglycoside moiety and the terpenyl moiety are covalently linked via an imine group.

4. The conjugate according to claim 1, wherein the aminoglycoside moiety and the terpenyl moiety are linked via electrostatic interactions.

5. The conjugate according to claim 1, wherein the conjugate is cleavable into a pharmaceutically active aminoglycoside and a pharmaceutically active terpenoid.

6. The conjugate according to claim 1, wherein the terpenyl moiety is a farnesyl moiety.

7. The conjugate according to claim 1, wherein the conjugate is selected from the group consisting of
(i) tobramycin-farnesyl conjugates of the following formula

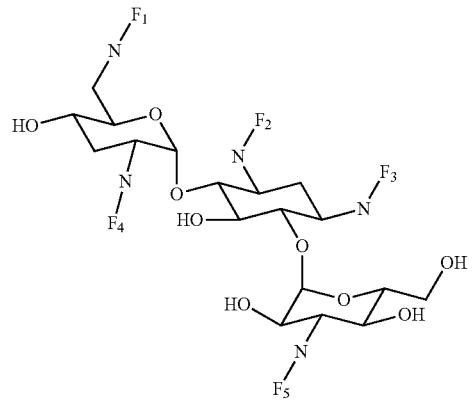

Tobramycin-Farnesyl Formula wherein $F_1$, $F_2$, $F_3$, $F_4$, $F_5$ are —$H_2$ or Fi and wherein at least one of $F_1$, $F_2$, $F_3$, $F_4$, $F_5$ is Fi, (ii) kanamycin A-farnesyl conjugates of the following formula

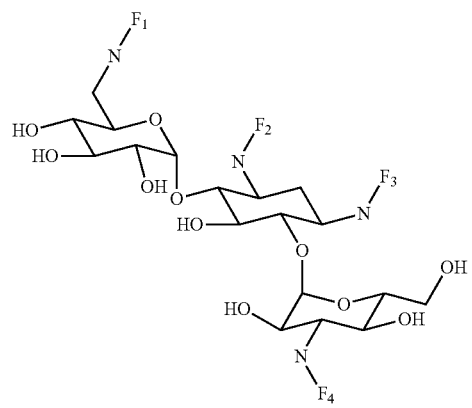

Kanamycin A-Farnesyl Formula wherein $F_1$, $F_2$, $F_3$, $F_4$ are —$H_2$ or Fi and wherein at least one of $F_1$, $F_2$, $F_3$, $F_4$ is Fi, (iii) kanamycin B-farnesyl conjugates of the following formula

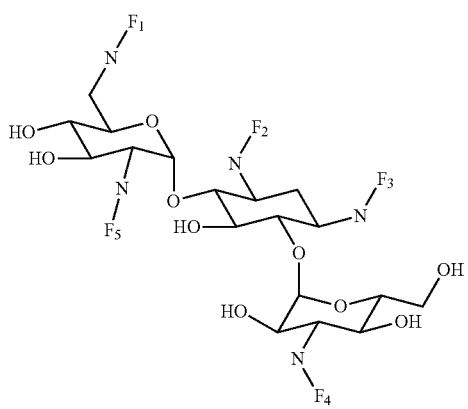

Kanamycin B-Farnesyl Formula wherein $F_1, F_2, F_3, F_4, F_5$ are $—H_2$ or Fi and wherein at least one of $F_1, F_2, F_3, F_4, F_5$ is Fi, (iv) kanamycin C-farnesyl conjugates of the following formula

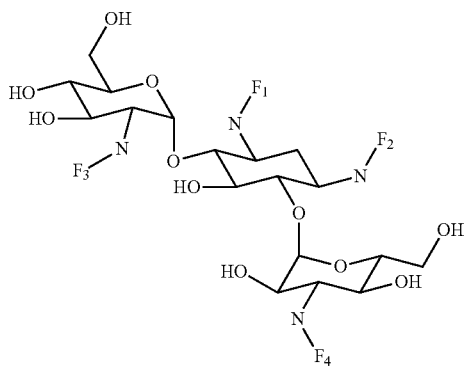

Kanamycin C-Farnesyl Formula wherein $F_1, F_2, F_3, F_4$ are $—H_2$ or Fi and wherein at least one of $F_1, F_2, F_3, F_4$ is Fi, (v) 6'-OH kanamycin A-farnesyl conjugates of the following formula

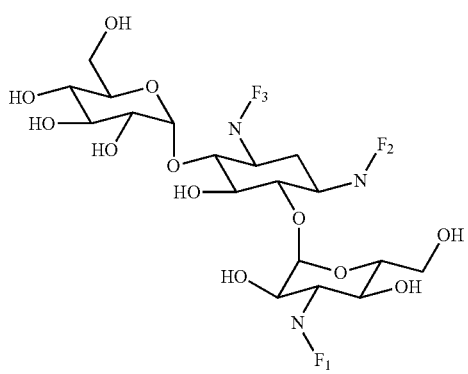

6'-OH-Kanamycin A-Farnesyl Formula wherein $F_1, F_2, F_3$ are $—H_2$ or Fi and wherein at least one of $F_1, F_2, F_3$ is Fi, (vi) dibekacin-farnesyl conjugates of the following formula

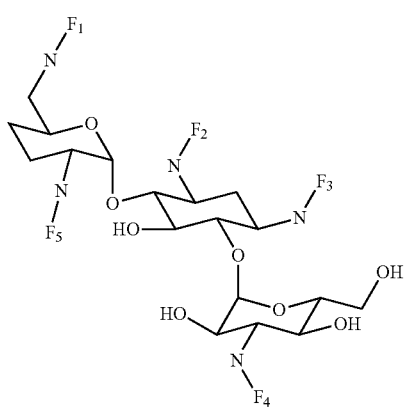

Dibekacin-Farnesyl Formula wherein $F_1, F_2, F_3, F_4, F_5$ are $—H_2$ or Fi and wherein at least one of $F_1, F_2, F_3, F_4, F_5$ is Fi, (vii) amikacin-farnesyl conjugates of the following formula

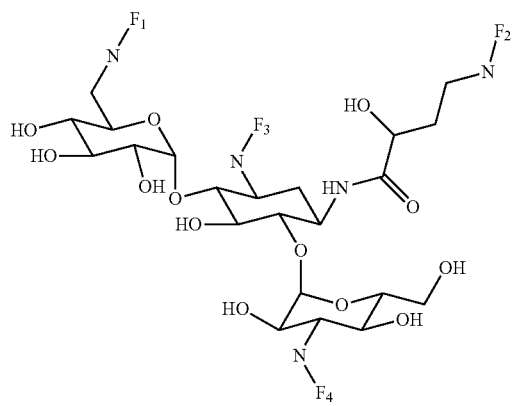

Amikacin-Farnesyl Formula wherein $F_1$, $F_2$, $F_3$, $F_4$ are —$H_2$ or Fi and wherein at least one of $F_1$, $F_2$, $F_3$, $F_4$ is Fi, (viii) arbekacin-farnesyl conjugates of the following formula

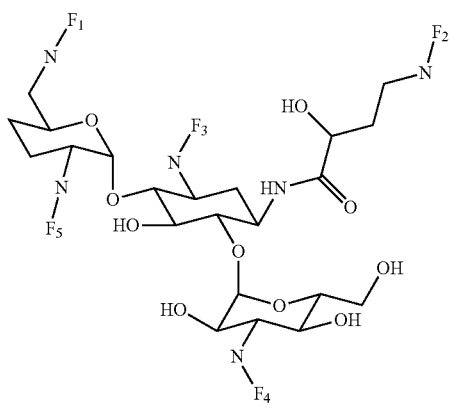

Arbekacin-Farnesyl Formula wherein $F_1$, $F_2$, $F_3$, $F_4$, $F_5$ are —$H_2$ or Fi and wherein at least one of $F_1$, $F_2$, $F_3$, $F_4$, $F_5$ is Fi, (ix) gentamicin C1-farnesyl conjugates of the following formula

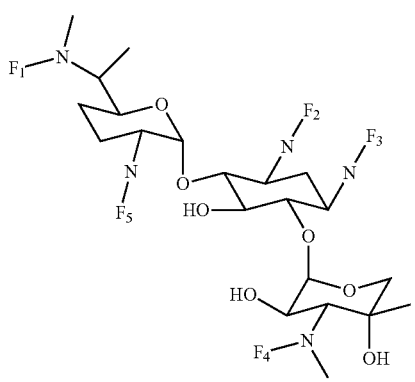

Gentamicin C1-Farnesyl Formula wherein $F_2$, $F_3$, $F_5$ are —$H_2$ or Fi, wherein $F_1$, $F_4$ are —H or Fen and wherein at least one of $F_2$, $F_3$, $F_5$ is Fi, (x) gentamicin C2-farnesyl conjugates of the following formula

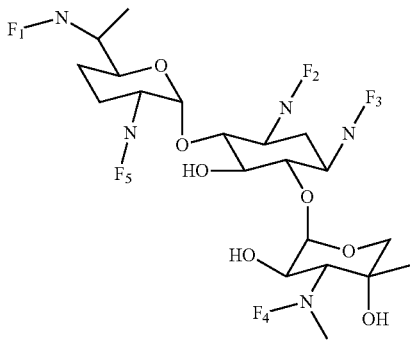

Gentamicin C2-Farnesyl Formula wherein $F_1$, $F_2$, $F_3$, $F_5$ are —$H_2$ or Fi, wherein $F_4$ is —H or Fen and wherein at least one of $F_1$, $F_2$, $F_3$, $F_5$ is Fi, (xi) gentamicin C1A-farnesyl conjugates of the following formula

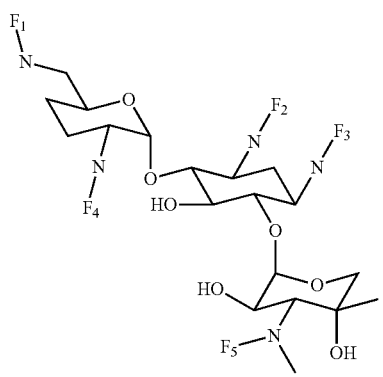

Gentamicin C1A-Farnesyl Formula wherein $F_1$, $F_2$, $F_3$, $F_4$ are —$H_2$ or Fi, wherein $F_5$ is —H or Fen and wherein at least one of $F_1$, $F_2$, $F_3$, $F_4$ is Fi, (xii) geneticin (G418)-farnesyl conjugates of the following formula

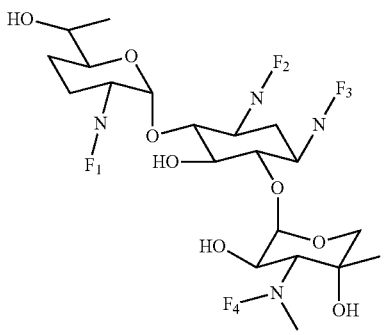

Geneticin (G418)-Farnesyl Formula wherein $F_1$, $F_2$, $F_3$ are —$H_2$ or Fi, wherein $F_4$ is —H or Fen and wherein at least one of $F_1$, $F_2$, $F_3$ is Fi, (xiii) netilmicin-farnesyl conjugates of the following formula

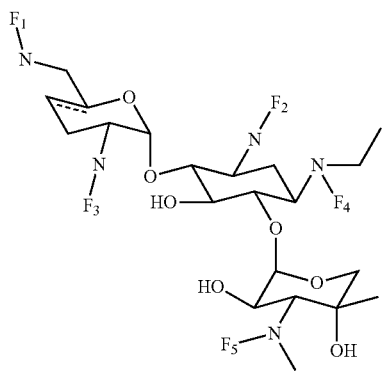

Netilmicin-Farnesyl Formula wherein $F_1$, $F_2$, $F_3$ are —$H_2$ or Fi, wherein $F_4$, $F_5$ are —H or Fen and wherein at least one of $F_1$, $F_2$, $F_3$ is Fi, (xiv) sisomicin-farnesyl conjugates of the following formula

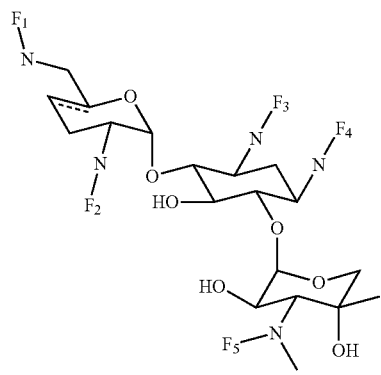

Sisomicin-Farnesyl Formula wherein $F_1$, $F_2$, $F_3$, $F_4$ are —$H_2$ or Fi, wherein $F_5$ is —H or Fen and wherein at least one of $F_1$, $F_2$, $F_3$, $F_4$ is Fi, (xv) verdamicin-farnesyl conjugates of the following formula

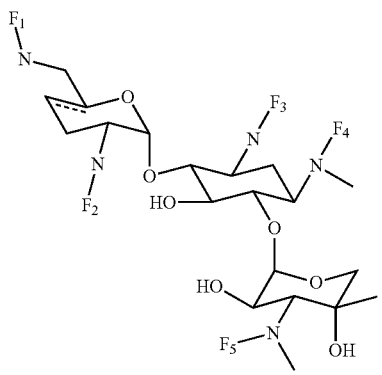

Verdamicin-Farnesyl Formula wherein $F_1$, $F_2$, $F_3$ are —$H_2$ or Fi, wherein $F_4$, $F_5$ are —H or Fen and wherein at least one of $F_1$, $F_2$, $F_3$ is Fi, (xvi) plazomicin-farnesyl conjugates of the following formula

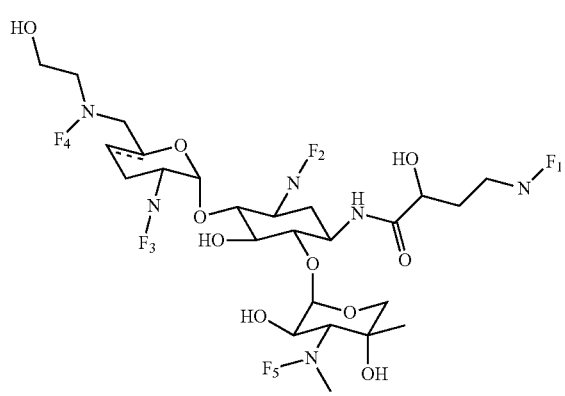

Plazomicin-Farnesyl Formula wherein $F_1$, $F_2$, $F_3$ are —$H_2$ or Fi, wherein $F_4$, $F_5$ are —H or Fen and wherein at least one of $F_1$, $F_2$, $F_3$ is Fi, (xvii) isepamicin-farnesyl conjugates of the following formula

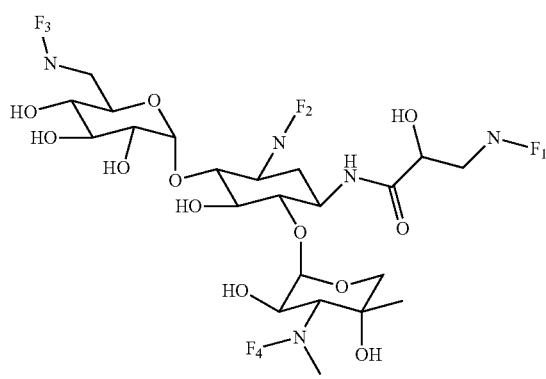

Isepamicin-Farnesyl Formula wherein $F_1$, $F_2$, $F_3$ are —$H_2$ or Fi, wherein $F_4$ is —H or Fen and wherein at least one of $F_1$, $F_2$, $F_3$ is Fi, (xviii) neomycin B-farnesyl conjugates of the following formula

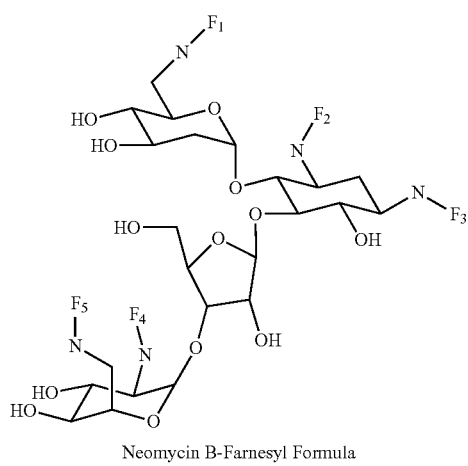

Neomycin B-Farnesyl Formula wherein $F_1$, $F_2$, $F_3$, $F_4$, $F_5$ are —$H_2$ or Fi and wherein at least one of $F_1$, $F_2$, $F_3$, $F_4$, $F_5$ is Fi, (xix) neomycin C-farnesyl conjugates of the following formula

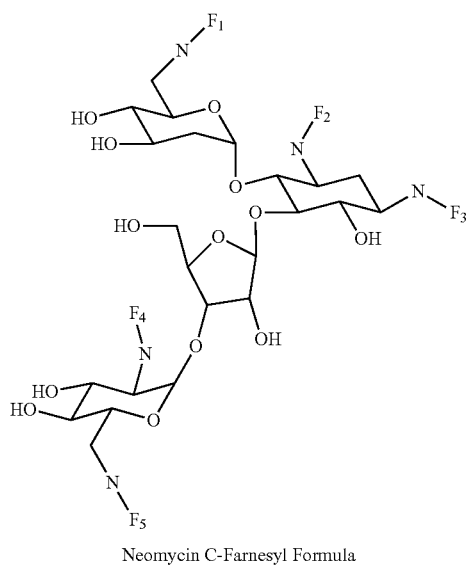

Neomycin C-Farnesyl Formula wherein $F_1$, $F_2$, $F_3$, $F_4$, $F_5$ are —$H_2$ or Fi and wherein at least one of $F_1$, $F_2$, $F_3$, $F_4$, $F_5$ is Fi, (xx) neomycin E-farnesyl conjugates of the following formula

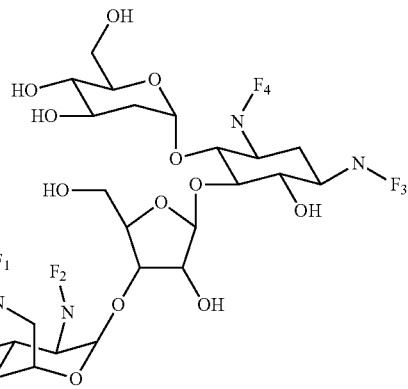

Paramomycin (Neomycin E)-Farnesyl Formula wherein $F_1$, $F_2$, $F_3$, $F_4$ are —$H_2$ or Fi and wherein at least one of $F_1$, $F_2$, $F_3$, $F_4$ is Fi, (xxi) lividomycin B-farnesyl conjugates of the following formula

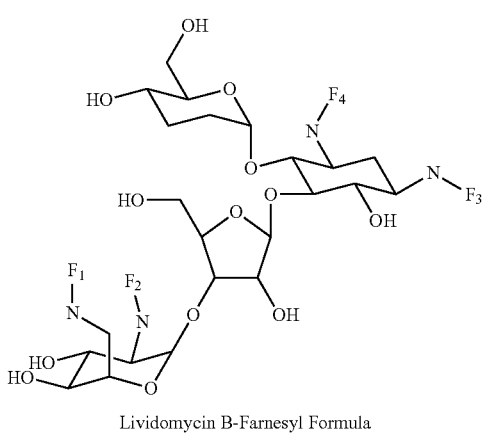

Lividomycin B-Farnesyl Formula wherein $F_1$, $F_2$, $F_3$, $F_4$ are —$H_2$ or Fi and wherein at least one of $F_1$, $F_2$, $F_3$, $F_4$ is Fi, (xxii) lividomycin A-farnesyl conjugates of the following formula

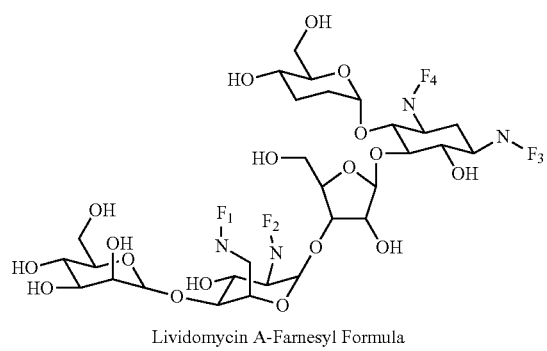

Lividomycin A-Farnesyl Formula wherein $F_1$, $F_2$, $F_3$, $F_4$ are —$H_2$ or Fi and wherein at least one of $F_1$, $F_2$, $F_3$, $F_4$ is Fi, (xxiii) butirosin B/A-farnesyl conjugates of the following formula

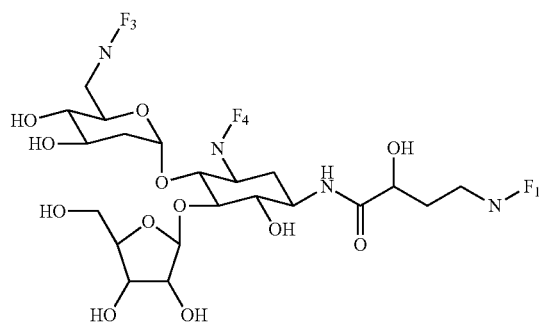

Butirosin B/A-Farnesyl Formula wherein $F_1$, $F_2$, $F_3$ are —$H_2$ or Fi and wherein at least one of $F_1$, $F_2$, $F_3$ is Fi, (xxiv) ribostamycin-farnesyl conjugates of the following formula

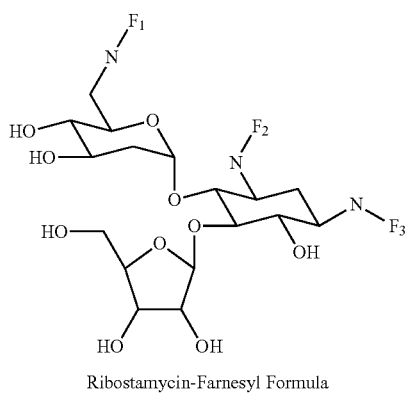

Ribostamycin-Farnesyl Formula wherein $F_1$, $F_2$, $F_3$ are —$H_2$ or Fi and wherein at least one of $F_1$, $F_2$, $F_3$ is Fi, (xxv) streptomycin-farnesyl conjugates of the following formula

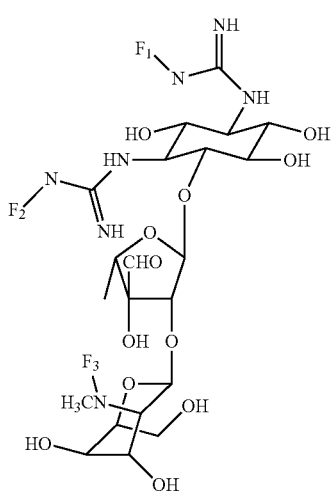

Streptomycin-Farnesyl Formula wherein $F_1$, $F_2$ are —$H_2$ or Fi, wherein $F_3$ is —H or Fen and wherein at least one of $F_1$, $F_2$ is Fi, (xxvi) 5'-hydroxystreptomycin-farnesyl conjugates of the following formula

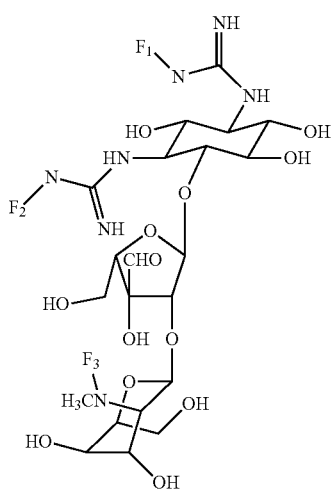

5'-hydroxystreptomycin-Farnesyl Formula wherein $F_1$, $F_2$ are —$H_2$ or Fi, wherein $F_3$ is —H or Fen and wherein at least one of $F_1$, $F_2$ is Fi, (xxvii) bluensomycin-farnesyl conjugates of the following formula

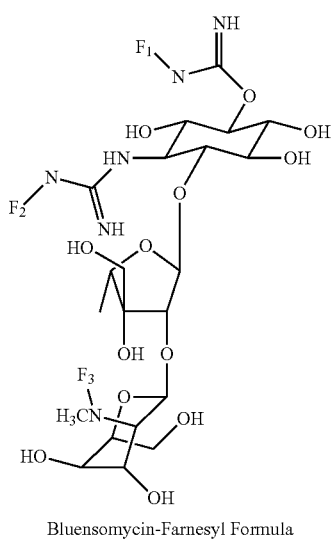

Bluensomycin-Farnesyl Formula wherein $F_1$, $F_2$ are —$H_2$ or Fi, wherein $F_3$ is —H or Fen and wherein at least one of $F_1$, $F_2$ is Fi, (xxviii) istamycin A-farnesyl conjugates of the following formula

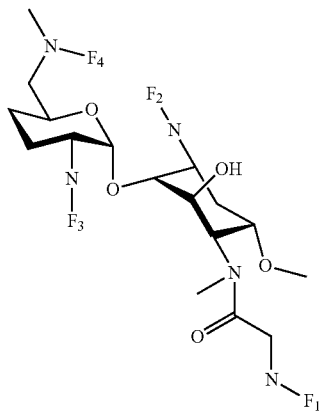

Istamycin B-Farnesyl Formula wherein $F_1$, $F_2$, $F_3$ are —$H_2$ or Fi, wherein $F_4$ is —H or Fen and wherein at least one of $F_1$, $F_2$, $F_3$ is Fi, (xxix) istamycin B-farnesyl conjugates of the following formula

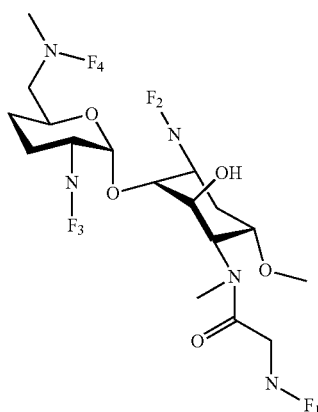

Istamycin B-Farnesyl Formula wherein $F_1$, $F_2$, $F_3$ are —$H_2$ or Fi, wherein $F_4$ is —H or Fen and wherein at least one of $F_1$, $F_2$, $F_3$ is Fi, (xxx) istamycin C-farnesyl conjugates of the following formula

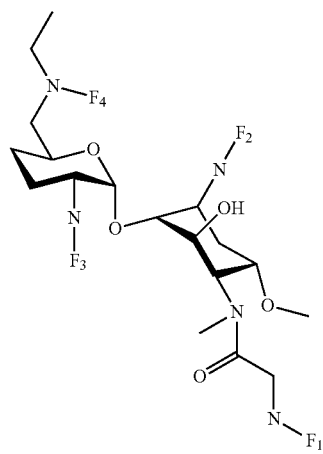

Istamycin C-Farnesyl Formula wherein $F_1$, $F_2$, $F_3$ are —$H_2$ or Fi, wherein $F_4$ is —H or Fen and wherein at least one of Fi, $F_2$, $F_3$ is Fi, (xxxi) fortimicin A (fortimicin B)-farnesyl conjugates of the following formula

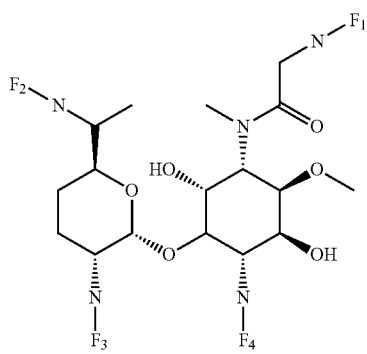

Fortimicin A (Fortimicin B)-Farnesyl Formula wherein $F_1$, $F_2$, $F_3$, $F_4$ are —$H_2$ or Fi and wherein at least one of $F_1$, $F_2$, $F_3$, $F_4$ is Fi, and (xxxii) apramycin-farnesyl conjugates of the following formula

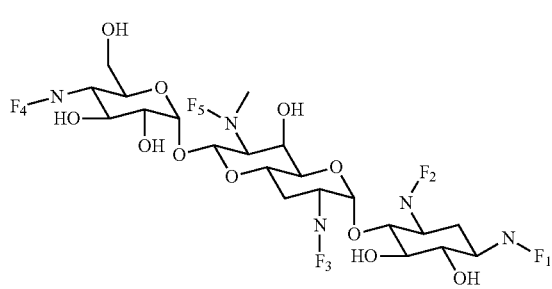

Apramycin-Farnesyl Formula wherein $F_1$, $F_2$, $F_3$, $F_4$ are —$H_2$ or Fi, wherein $F_5$ is —H or Fen and wherein at least one of $F_1$, $F_2$, $F_3$, $F_4$ is Fi, wherein Fi is a farnesyl moiety of the following formula

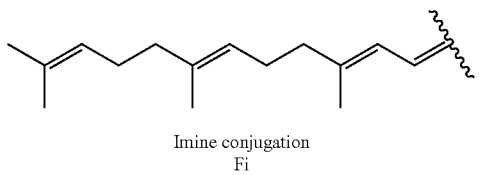 [SMILES: *=C/C=C(\C)CC/C=C(\C)CCC=C(C)C]

Imine conjugation
Fi and wherein Fen is a farnesyl moiety of the following formula

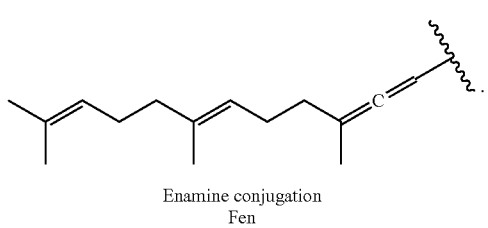 [SMILES: *C=C=C(C)CC/C=C(\C)CCC=C(C)C]

Enamine conjugation
Fen

8. The conjugate according to claim 1, wherein the aminoglycoside is selected from the group consisting of tobramycin, amikacin, plazomicin, neomycin, gentamicin, kanamycin, netilmicin, sisomicin and dibekacin.

9. A method of treating an infectious disease in a subject, comprising administering a therapeutically effective amount of one or more of the conjugates of claim 1 to a subject having an infectious disease.

10. The method according to claim 9, wherein the infectious disease is responsive to the pharmaceutical activity of the aminoglycoside and/or to the pharmaceutical activity of the terpenoid.

11. A pharmaceutical composition comprising the conjugate of claim 1.

12. A method for preparing the conjugate of claim 1, the method comprising the following steps:
 a) mixing an aminoglycoside with a terpenoid in a solvent,
 b) incubating the mixture,
 c) isolating the conjugate.

13. The method according to claim 12, wherein the terpenoid is selected from the group consisting of farnesol and derivatives thereof.

14. A nano-assembly comprising the conjugate of claim 1.

15. The conjugate according to claim 1, wherein the conjugate is selected from the group consisting of

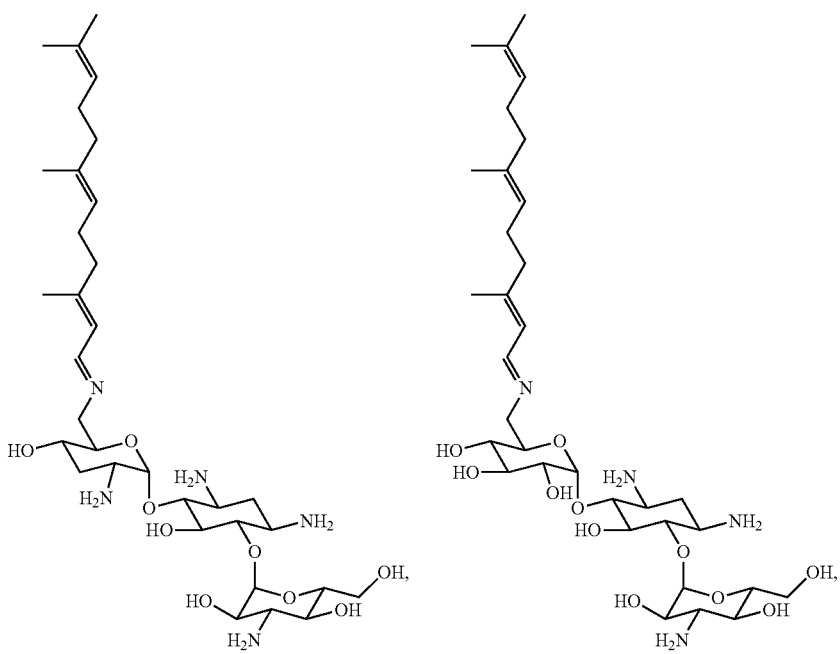

-continued
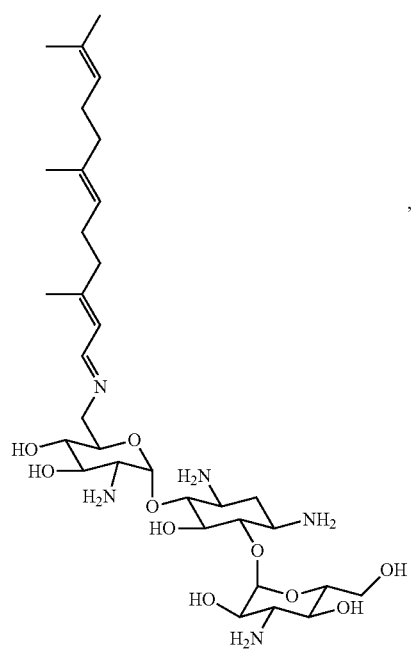
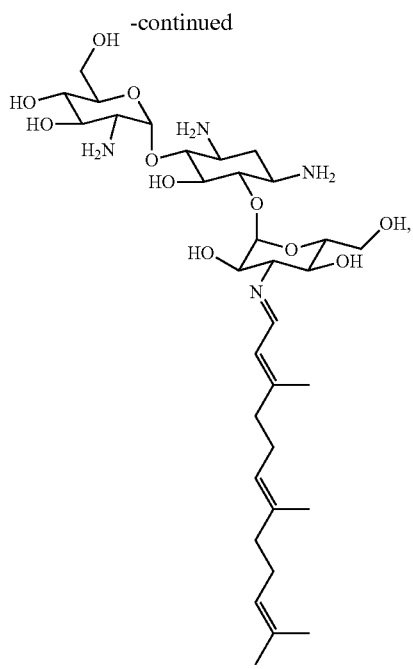
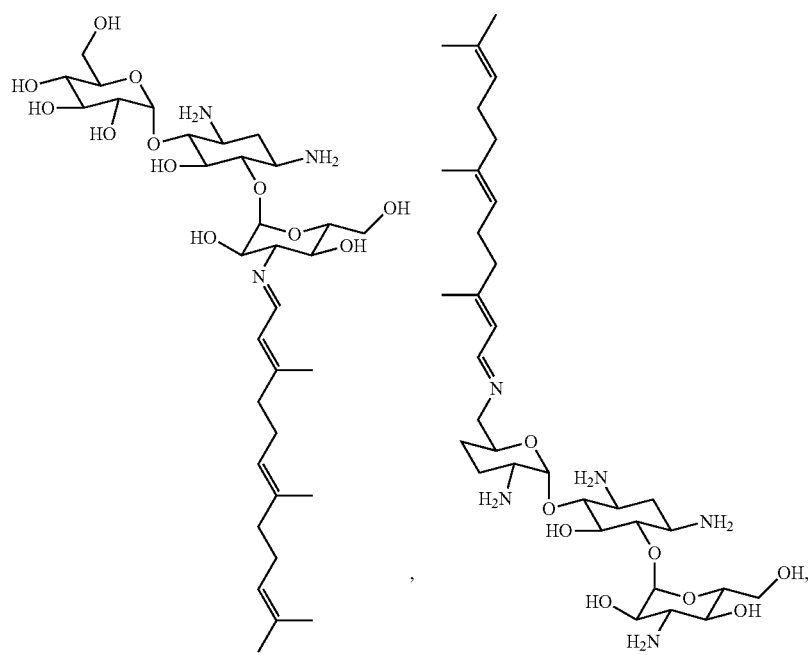

-continued
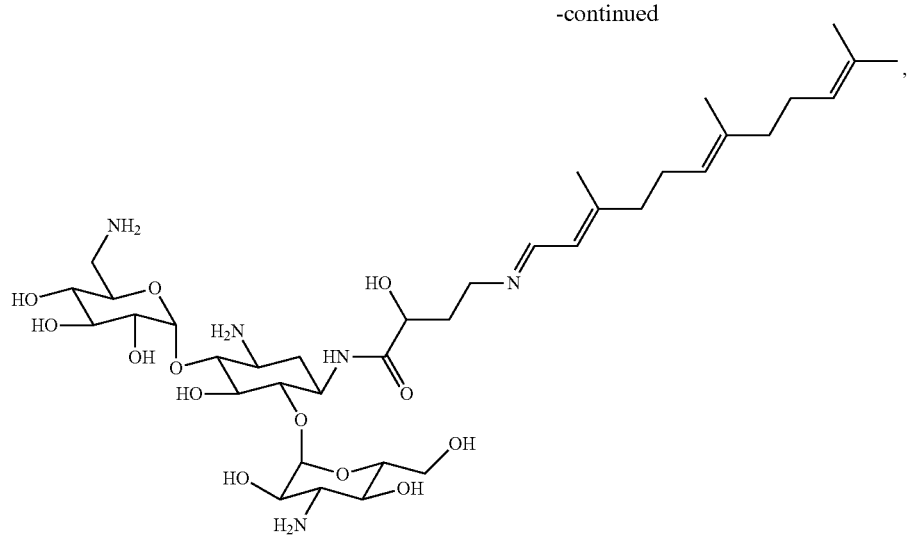
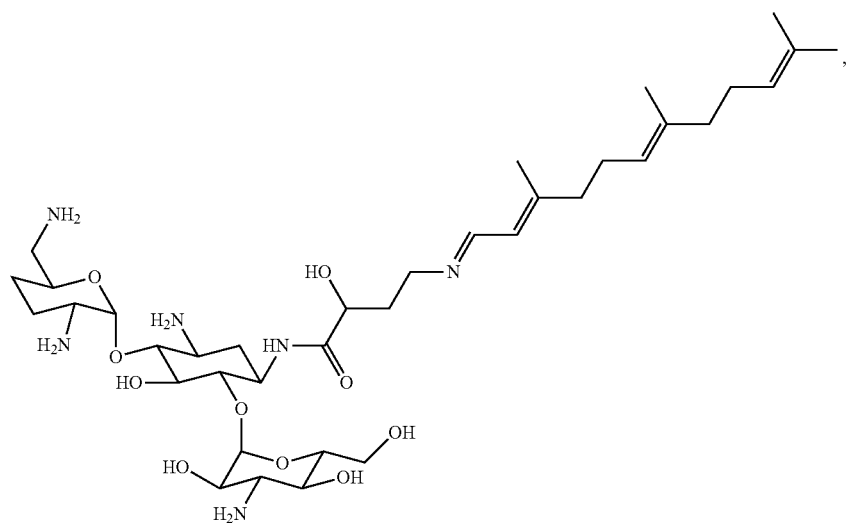
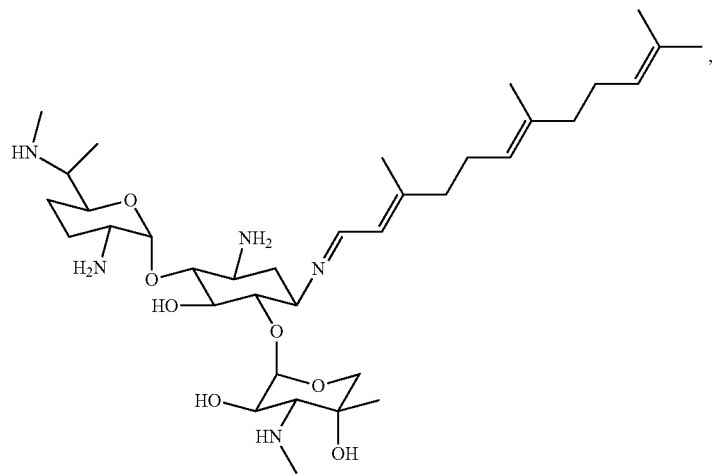

-continued
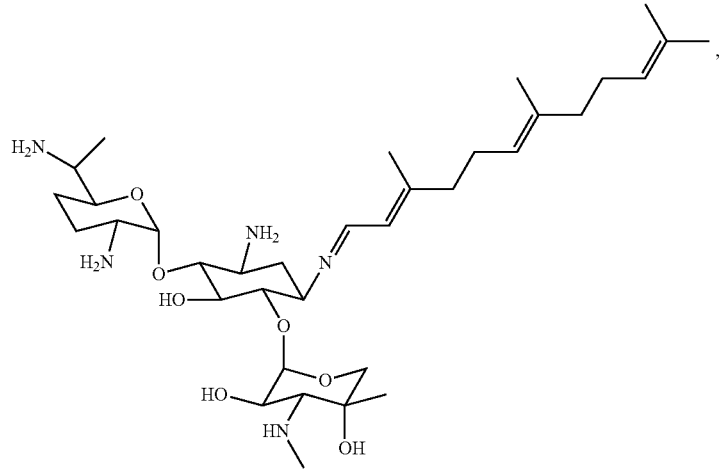
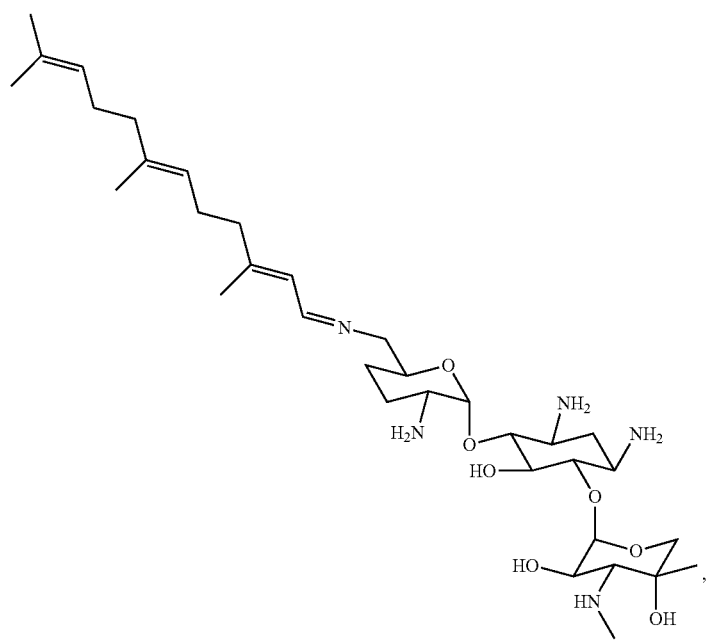
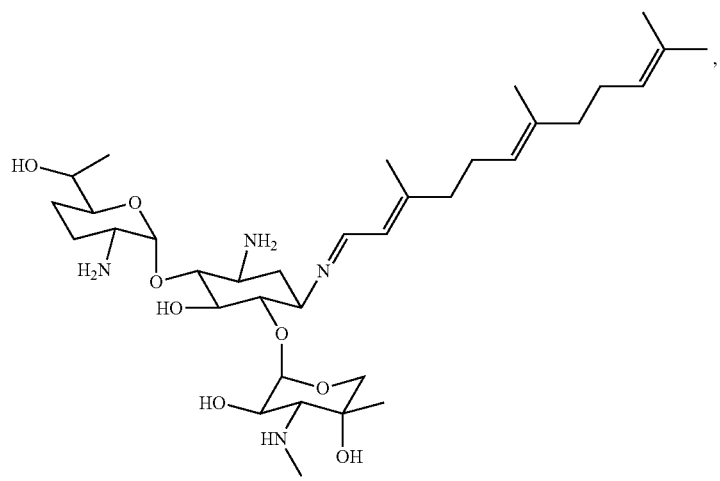

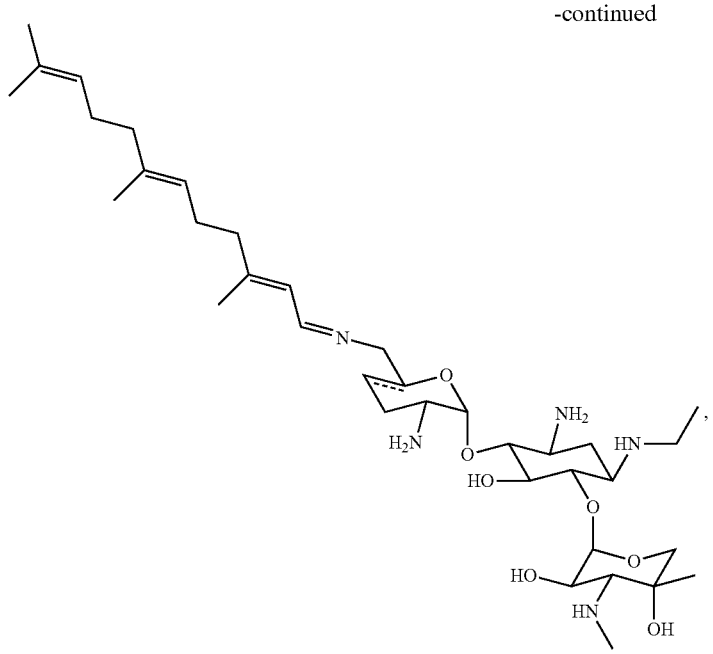
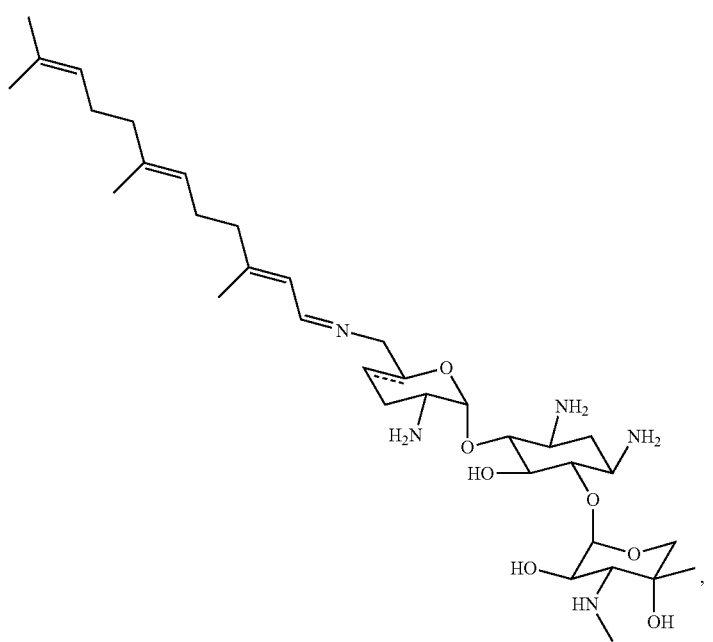

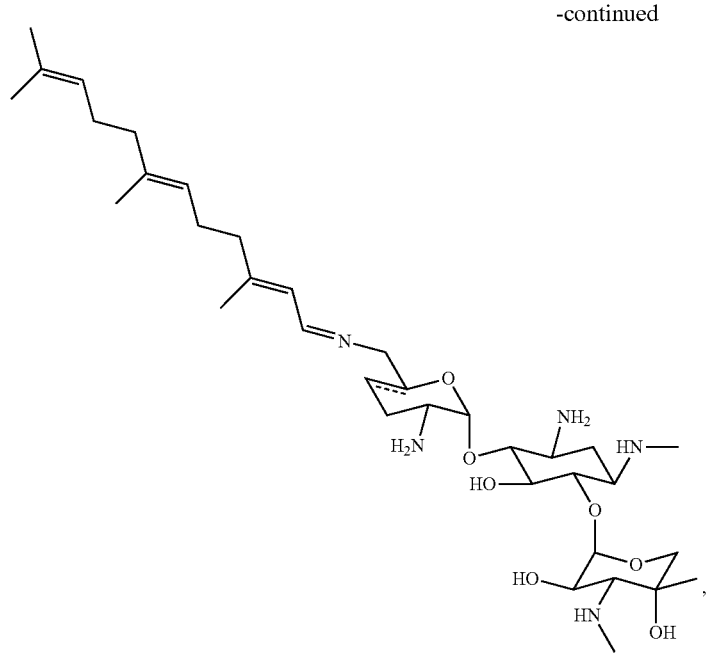
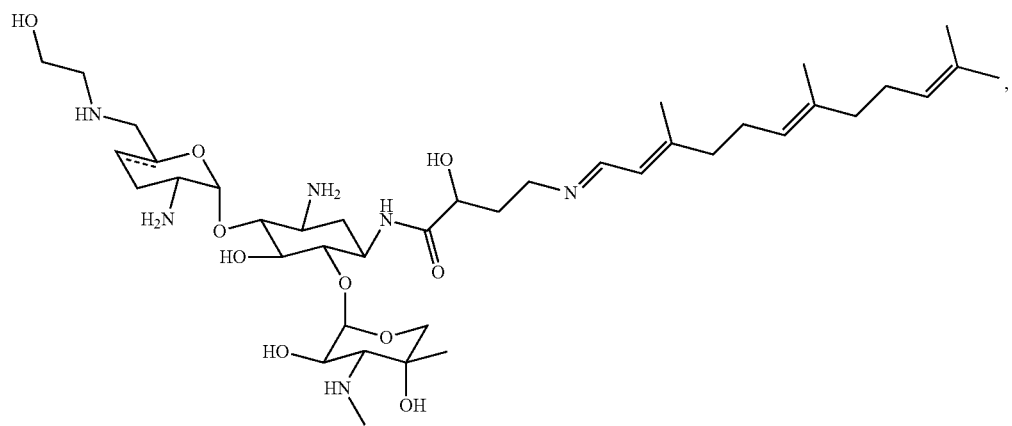
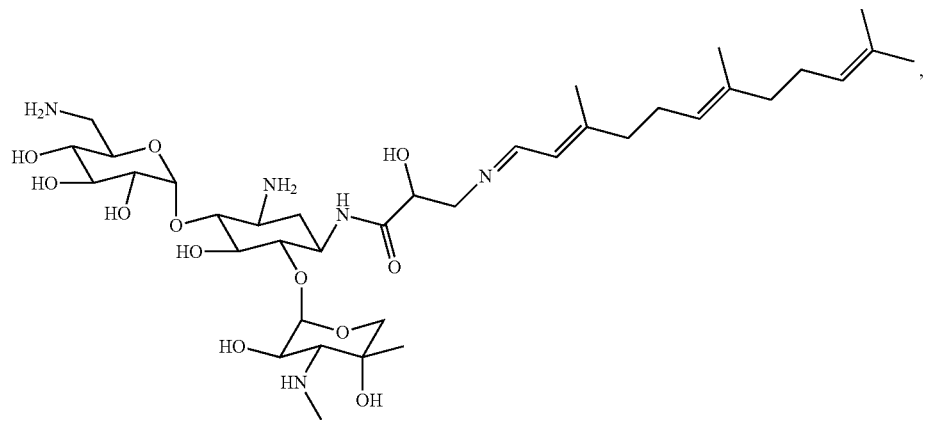

-continued
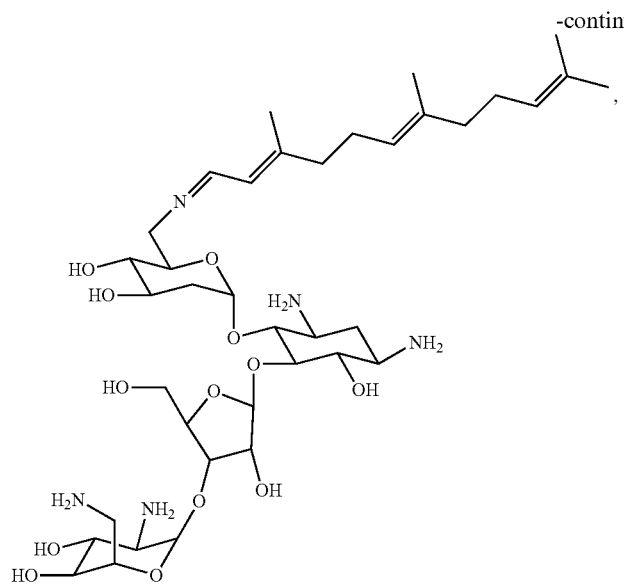
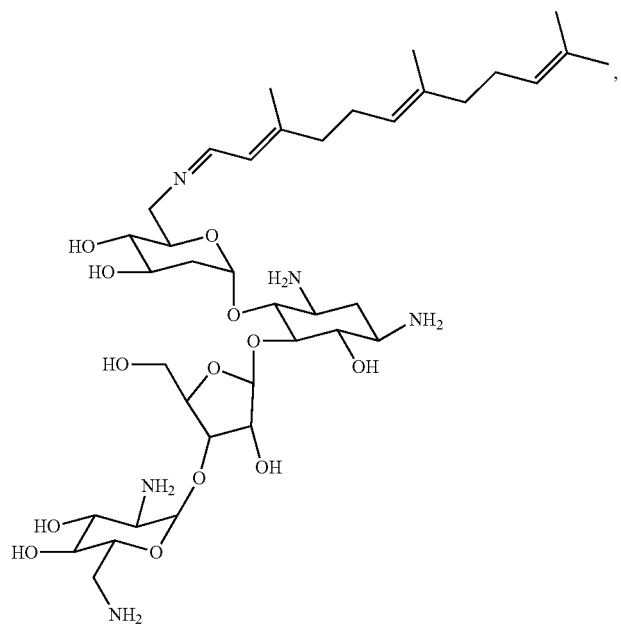
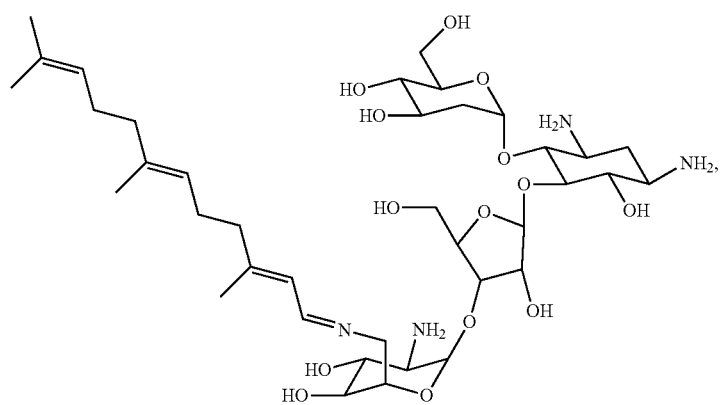

-continued
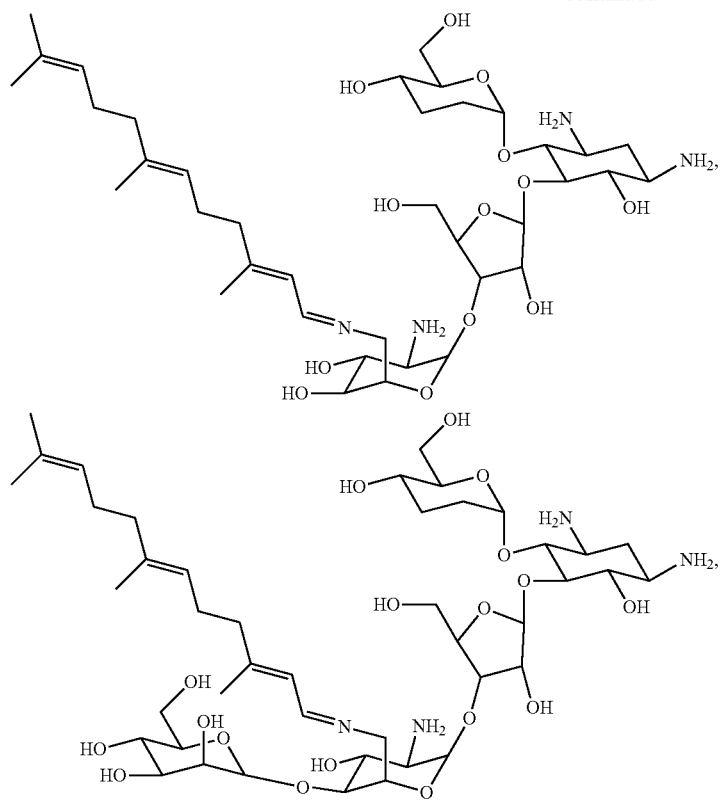
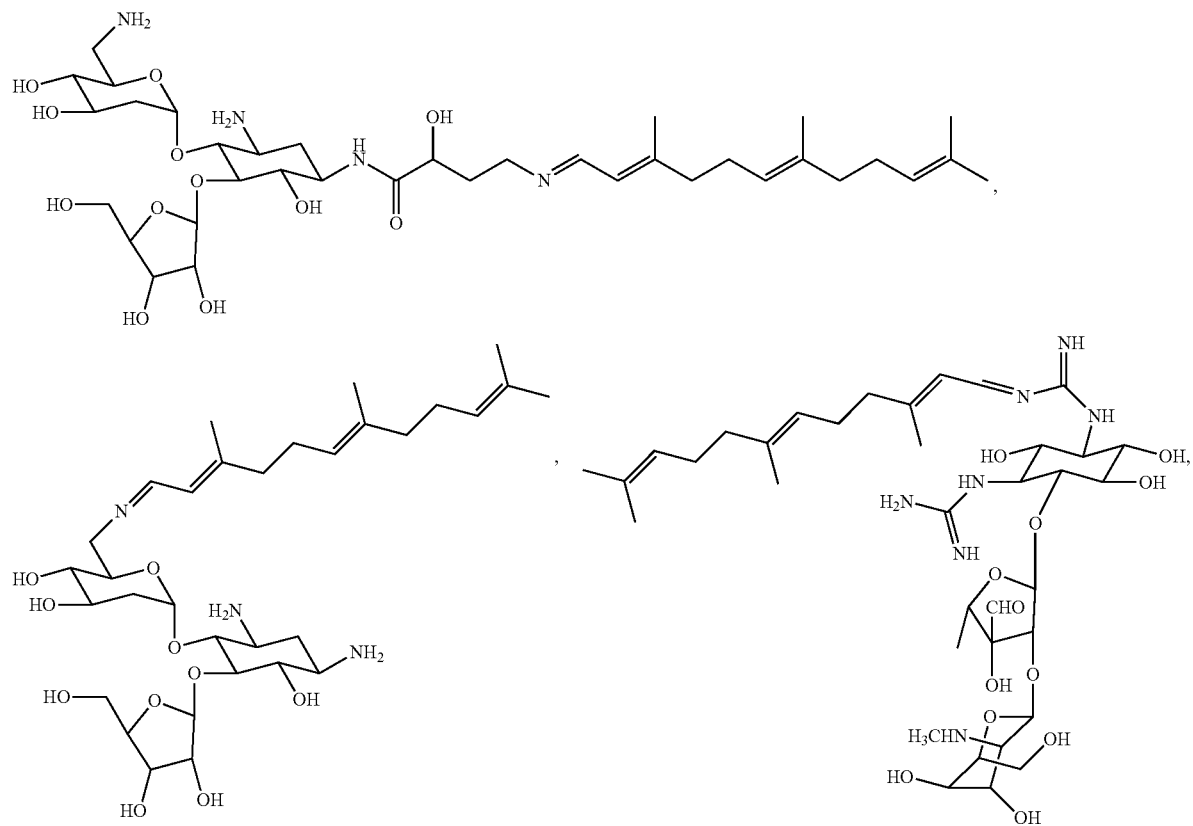

-continued
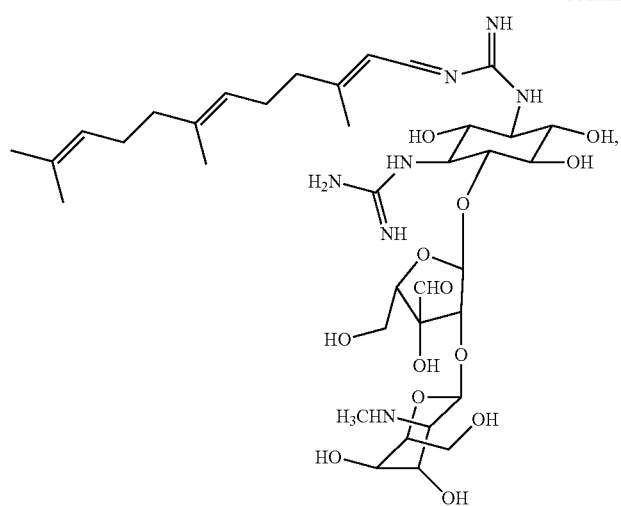
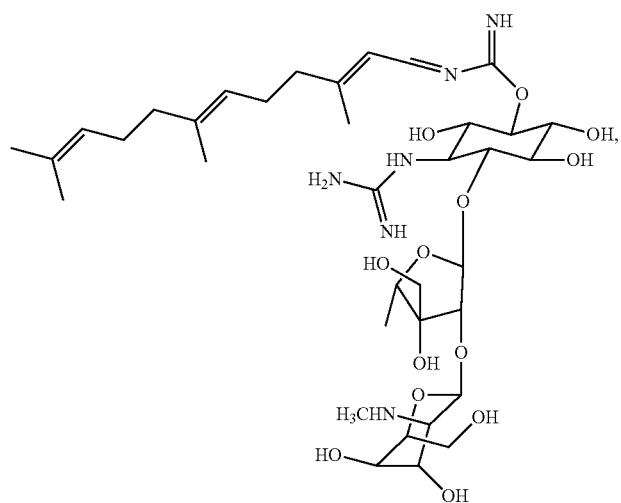
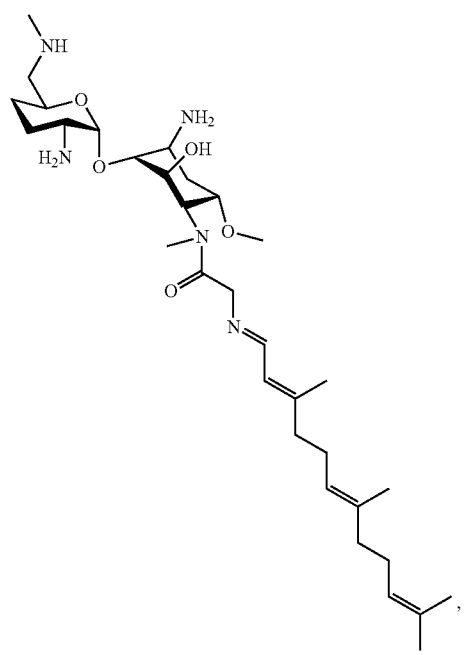
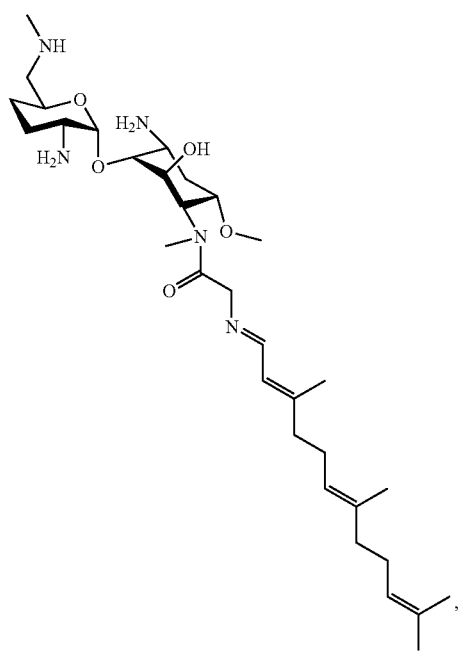

-continued
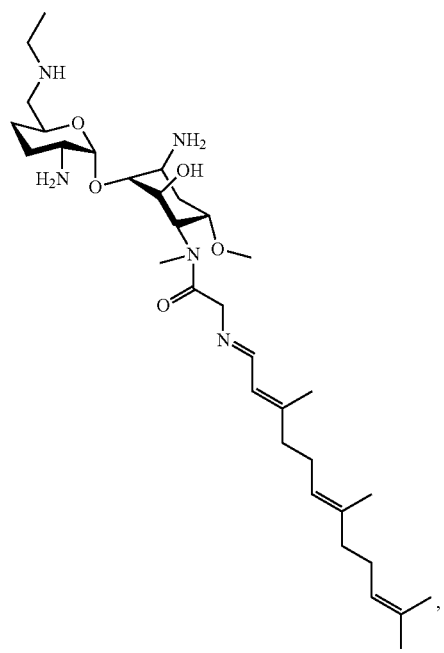
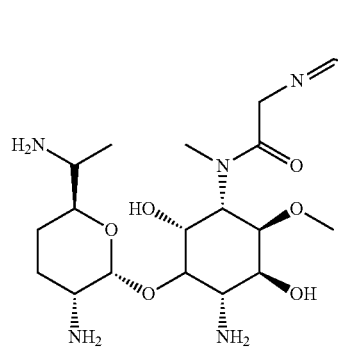
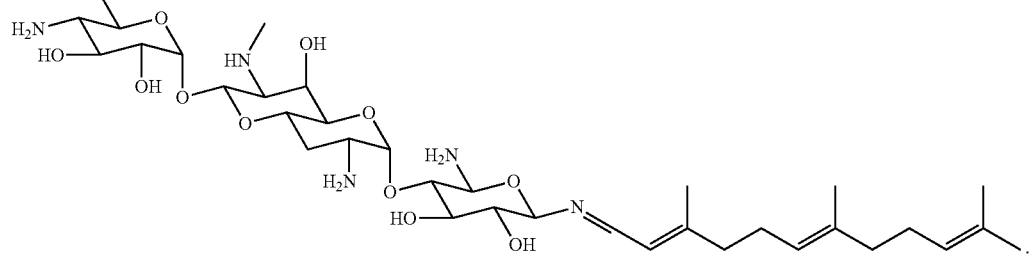
* * * * *